(12) United States Patent
Togino

(10) Patent No.: US 10,634,898 B2
(45) Date of Patent: Apr. 28, 2020

(54) STEROSCOPIC IMAGING OPTICAL SYSTEM, STEROSCOPIC IMAGING APARATUS, AND ENDOSCOPE

(71) Applicant: OLYMPUS CORPORATION, Tokyo (JP)

(72) Inventor: Takayoshi Togino, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 780 days.

(21) Appl. No.: 15/173,665

(22) Filed: Jun. 5, 2016

(65) Prior Publication Data

US 2016/0282602 A1 Sep. 29, 2016

Related U.S. Application Data

(63) Continuation of application No. PCT/JP2014/076966, filed on Oct. 8, 2014.

(30) Foreign Application Priority Data

Dec. 5, 2013 (JP) .................................. 2013-251844

(51) Int. Cl.
*H04N 13/204* (2018.01)
*A61B 1/00* (2006.01)
(Continued)

(52) U.S. Cl.
CPC ...... *G02B 23/2415* (2013.01); *A61B 1/00009* (2013.01); *A61B 1/00096* (2013.01);
(Continued)

(58) Field of Classification Search
CPC ................ G02B 23/2415; G02B 23/06; G02B 23/2484; H04N 13/204; A61B 1/00; A61B 1/04
(Continued)

(56) References Cited

U.S. PATENT DOCUMENTS 2,268,338 A * 12/1941 Kober .................... G03B 35/00
352/57
4,178,090 A 12/1979 Marks et al.
(Continued)

FOREIGN PATENT DOCUMENTS

JP   H 08-056891 A   3/1996
JP      8-220449       8/1996
(Continued)

OTHER PUBLICATIONS

European Search Report dated Jul. 7, 2017, in counterpart European Patent Application No. 14 86 6919.5.
(Continued)

*Primary Examiner* — Timothy J Neal
*Assistant Examiner* — Jae Woo
(74) *Attorney, Agent, or Firm* — Hunton Andrews Kurth LLP

(57) ABSTRACT

The stereoscopic imaging optical system 1 includes, in order from an object side thereof to an image plane side thereof, a front group Gf including a first front group Gf1 with a center axis C1 thereof as center and a second front group Gf2 with a center axis C2 thereof arranged parallel with the center axis of the first front group as center, a front deflection group Gfd located on an image plane side of at least one of the first front group Gf1 and the second front group, and a rear group Gb that is located on the image plane side of the front group Gf and the front deflection group Gfd and has a single center axis.

19 Claims, 35 Drawing Sheets

(51) Int. Cl.
*A61B 1/05* (2006.01)
*A61B 1/04* (2006.01)
*G02B 23/24* (2006.01)
*G03B 35/10* (2006.01)
*G02B 13/18* (2006.01)
*G02B 23/06* (2006.01)
*G02B 27/00* (2006.01)
*G02B 13/22* (2006.01)
*G02B 27/42* (2006.01)

(52) U.S. Cl.
CPC ...... *A61B 1/00101* (2013.01); *A61B 1/00188* (2013.01); *A61B 1/00193* (2013.01); *A61B 1/04* (2013.01); *A61B 1/05* (2013.01); *G02B 13/18* (2013.01); *G02B 23/06* (2013.01); *G02B 23/2484* (2013.01); *G02B 27/0025* (2013.01); *G03B 35/10* (2013.01); *H04N 13/204* (2018.05); *G02B 13/22* (2013.01); *G02B 23/243* (2013.01); *G02B 27/4205* (2013.01)

(58) Field of Classification Search
USPC ........................................................ 600/166
See application file for complete search history.

(56) References Cited

U.S. PATENT DOCUMENTS

| | | | | |
|---|---|---|---|---|
| 4,555,168 A * | 11/1985 | Meier | ............... | G03B 37/00 353/7 |
| 5,459,605 A * | 10/1995 | Kempf | ............... | A61B 1/00165 359/462 |
| 5,743,846 A * | 4/1998 | Takahashi | .......... | A61B 1/00193 600/111 |
| 5,971,915 A * | 10/1999 | Yamamoto | ......... | A61B 1/00193 600/111 |
| 5,976,071 A | 11/1999 | Sekiya | | |
| 6,414,791 B1 * | 7/2002 | Sugawara | ............ | G02B 27/26 359/386 |
| 6,606,113 B2 * | 8/2003 | Nakamura | ......... | A61B 1/00193 348/45 |
| 6,628,457 B2 * | 9/2003 | Ito | .................. | A61B 90/25 359/368 |
| 6,922,285 B2 * | 7/2005 | Kobayashi | ............ | G03B 35/00 348/55 |
| 7,280,285 B2 * | 10/2007 | Nagahara | ............... | G02B 13/16 359/651 |
| 8,767,320 B2 * | 7/2014 | Fujii | .................. | G02B 23/2438 359/660 |
| 2002/0118450 A1 * | 8/2002 | Ito | ........................ | G02B 7/20 359/385 |
| 2002/0161278 A1 * | 10/2002 | Nakamura | ......... | A61B 1/00096 600/111 |
| 2003/0125608 A1 * | 7/2003 | Igarashi | ............. | A61B 1/00096 600/166 |
| 2004/0125469 A1 * | 7/2004 | Miyano | ................... | G02B 9/34 359/783 |
| 2005/0185050 A1 * | 8/2005 | Ohashi | ................ | H04N 13/218 348/50 |
| 2010/0208046 A1 * | 8/2010 | Takahashi | .......... | A61B 1/00193 348/65 |
| 2011/0242287 A1 * | 10/2011 | Cieslinski | .......... | G02B 27/2264 348/49 |
| 2013/0022344 A1 * | 1/2013 | Bae | ...................... | G02B 27/123 396/324 |
| 2013/0127997 A1 * | 5/2013 | Inomoto | ............... | G02B 13/16 348/46 |
| 2013/0170029 A1 * | 7/2013 | Morita | .................. | G02B 27/22 359/464 |
| 2014/0364693 A1 * | 12/2014 | Shechterman | ........ | A61B 1/055 600/111 |
| 2016/0320606 A1 * | 11/2016 | Togino | .................. | G03B 35/10 |

FOREIGN PATENT DOCUMENTS

| | | |
|---|---|---|
| JP | 2001-075046 | 3/2001 |
| JP | 2003-005096 | 1/2003 |
| JP | 2005-241791 | 9/2005 |
| JP | 2011-090166 A | 5/2011 |
| JP | 2012-220848 | 11/2012 |
| WO | WO 2011/049195 | 4/2011 |
| WO | WO 2013/114725 | 8/2013 |

OTHER PUBLICATIONS

International Search Report from International Application No. PCT/JP2014/076966 dated Jan. 13, 2015 (English-language translation).

* cited by examiner

Example 1

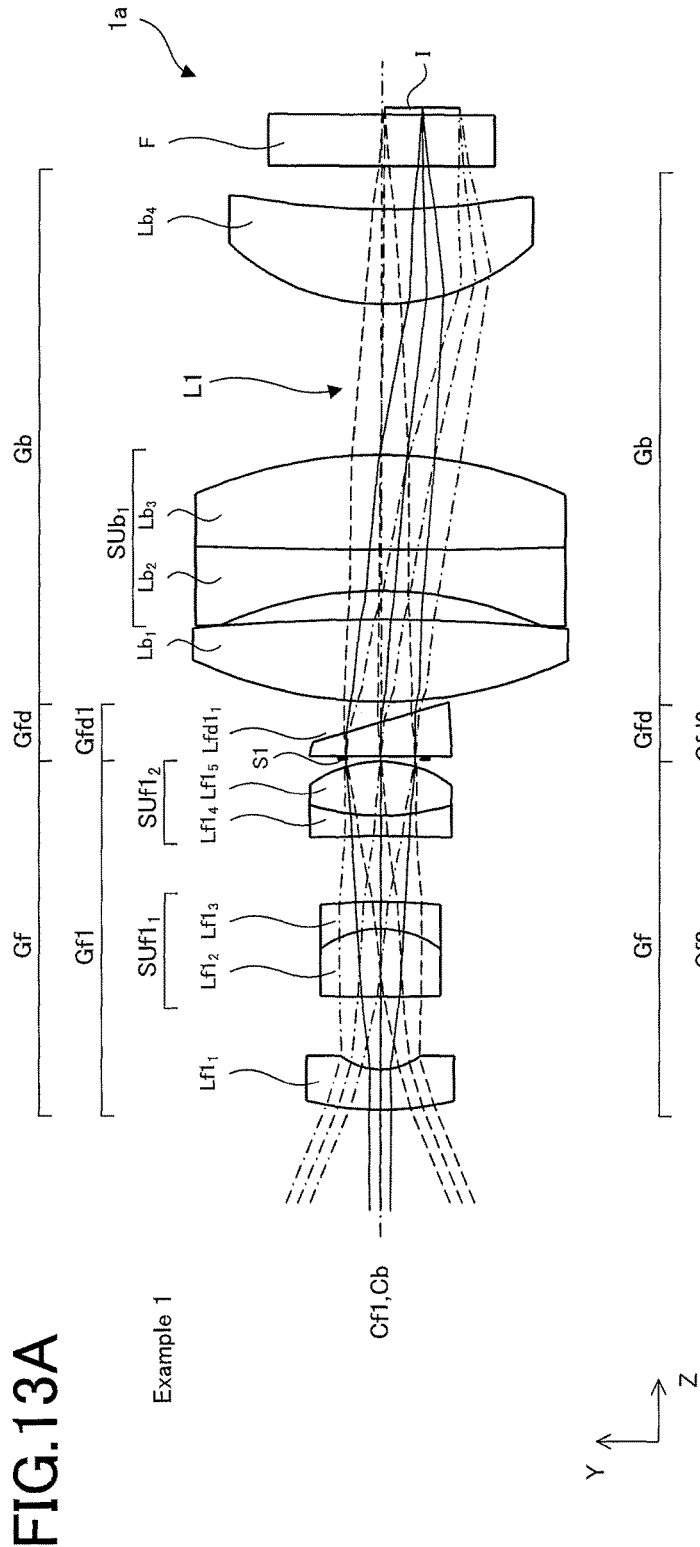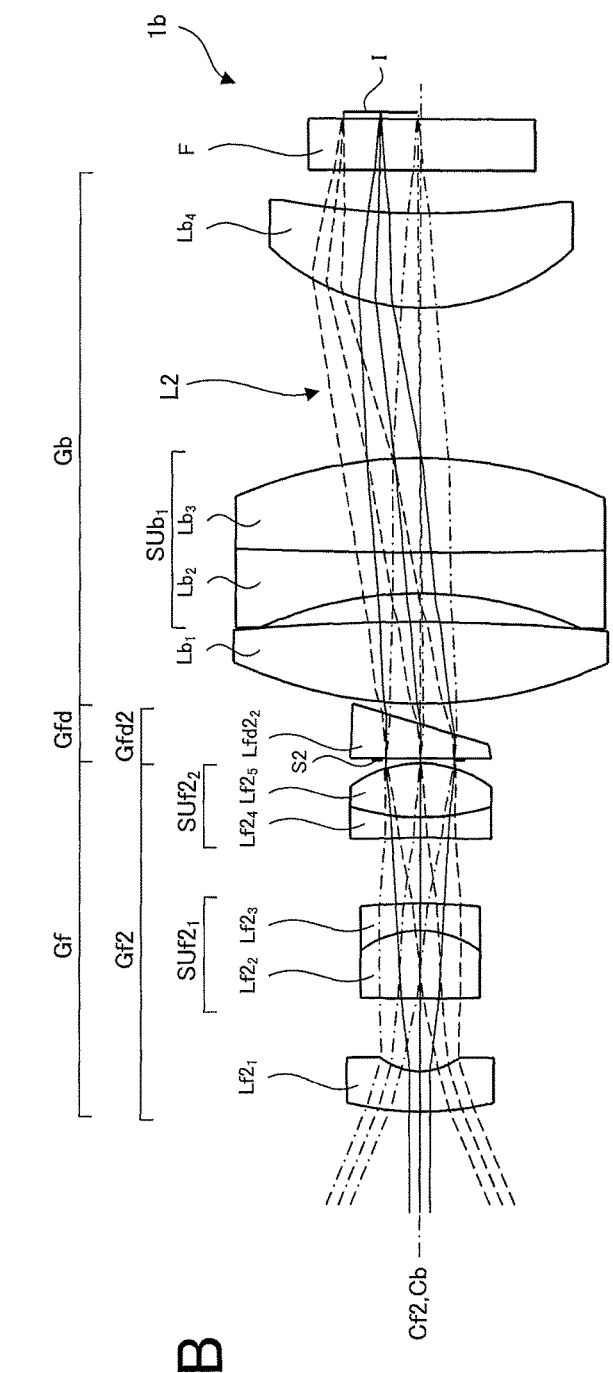
FIG.13A Example 1
FIG.13B ns

Example 2

Example 3

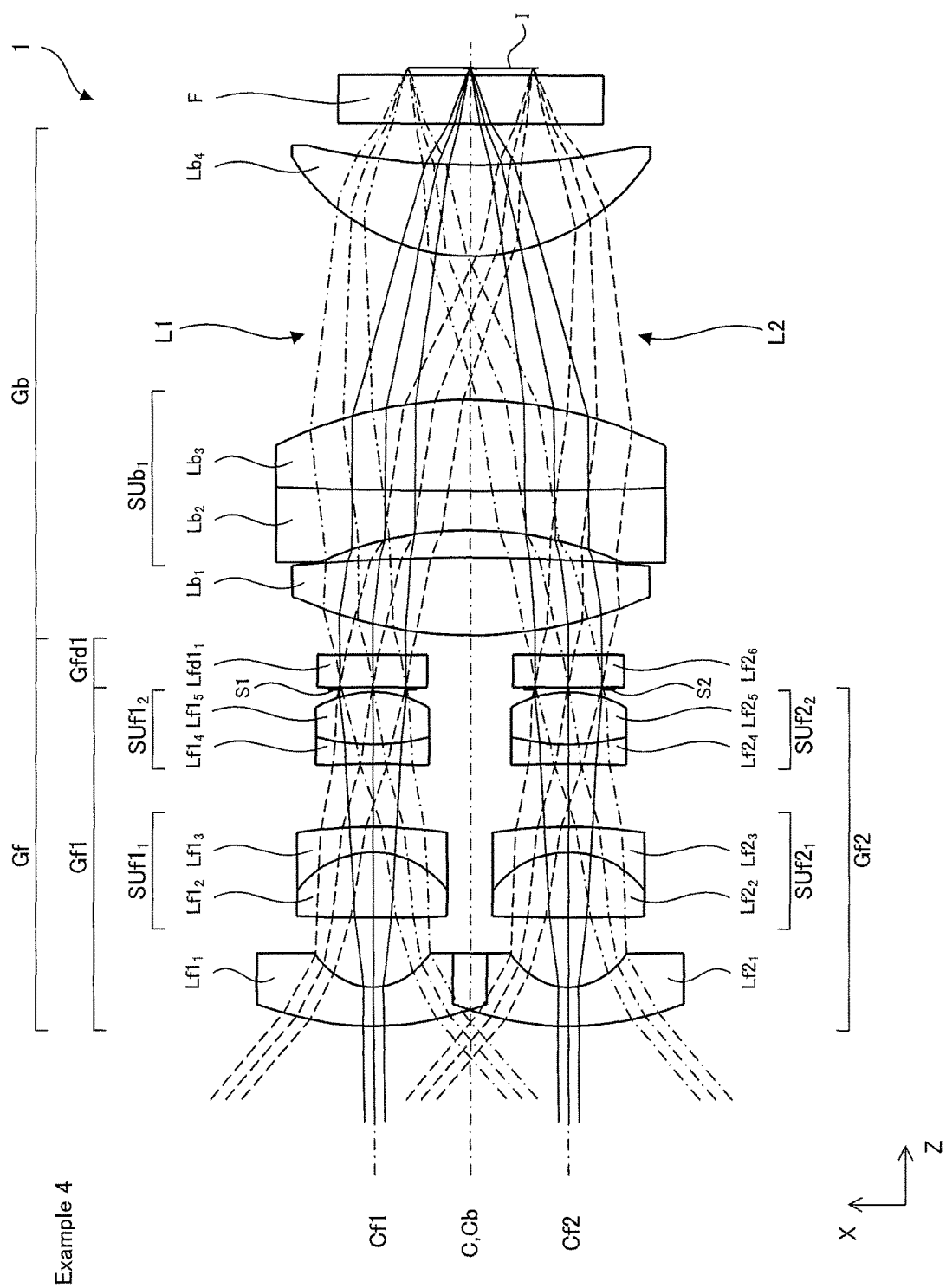
FIG.22 Example 4

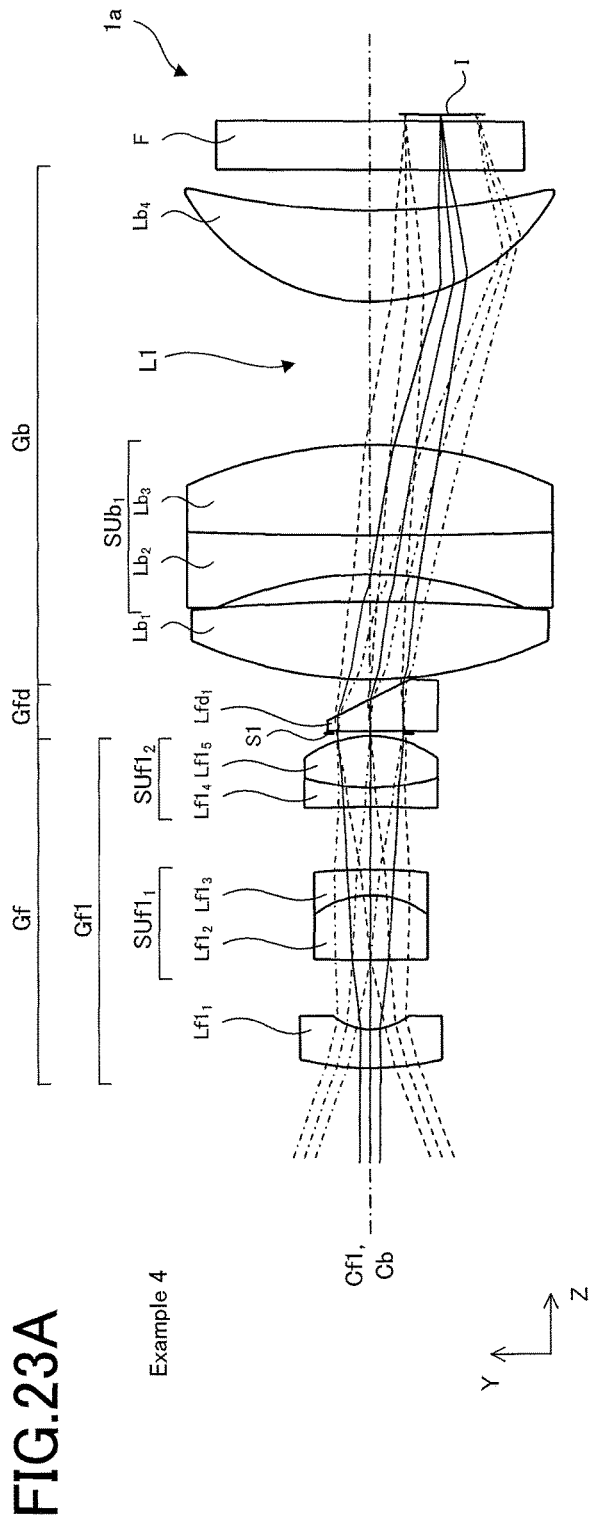
FIG.23A Example 4
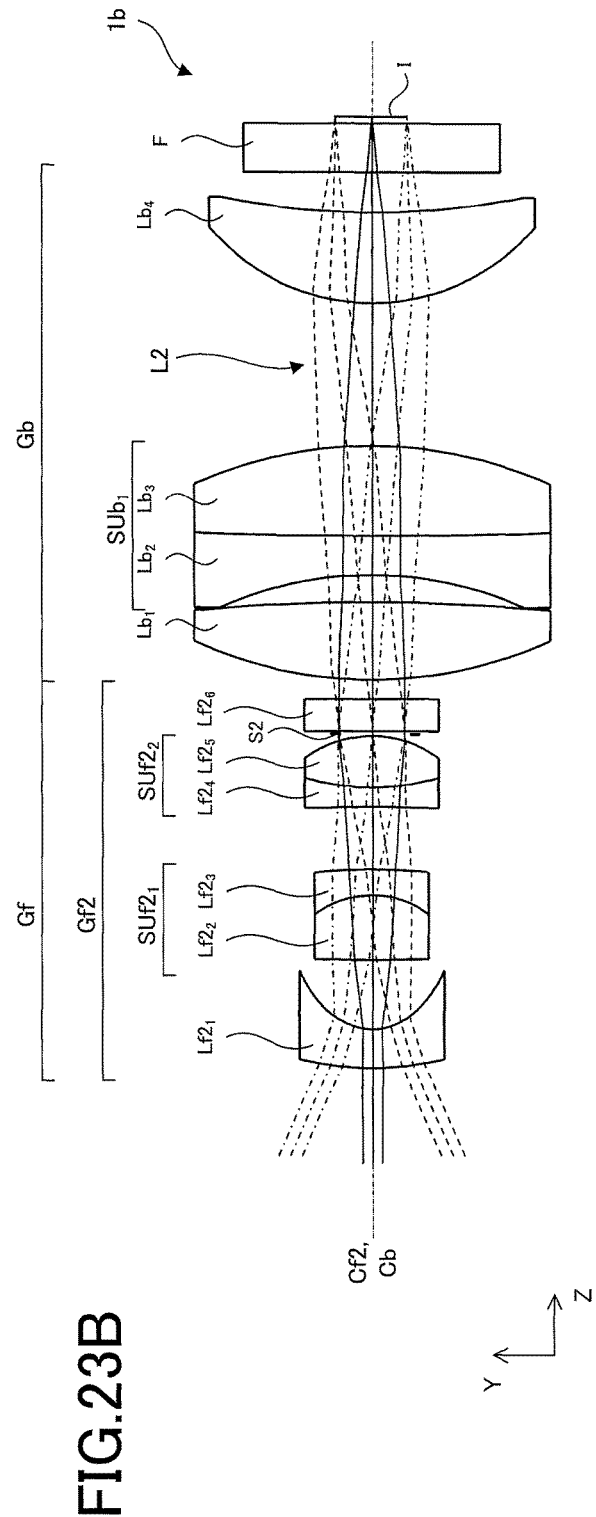
FIG.23B

Example 4 (The right optical path)

Example 6

Example 6

Example 7

Example 7

STEROSCOPIC IMAGING OPTICAL SYSTEM, STEROSCOPIC IMAGING APARATUS, AND ENDOSCOPE

CROSS-REFERENCE TO RELATED APPLICATIONS

This application is a continuation application of International Application No. PCT/JP2014/076966 filed on Oct. 8, 2014, which claims the benefit of Japanese Patent Application No. 2013-251844 filed on Dec. 5, 2013. The contents of both the PCT application and the Japan Application are incorporated herein by reference.

BACKGROUND OF THE INVENTION AND RELATED ART STATEMENT

The present invention relates to a stereoscopic imaging optical system, a stereoscopic imaging apparatus, and an endoscope, each capable of stereoscopic viewing.

For stereoscopic viewing of two images having different parallaxes, such techniques as disclosed in JP(A) 2003-5096 and International Publication WO 2011/049195 have so far been applied to an optical system for forming them within the same plane.

According to JP(A) 2003-5096, an optical system having two optical axes is provided on the object side while an optical system having one optical axis is provided on the image side. According to International Publication WO 2011/049195, an optical system having two optical axes is provided from an object to an image, and the left and right optical axes are passed by prisms through imaging optical systems located above and below such that a separation between image centers is made shorter by the prism on the imaging plane side to locate imaging planes above and below.

SUMMARY OF INVENTION

According to one embodiment of the invention, the abovementioned object is accomplished by the provision of a stereoscopic imaging apparatus including, in order from an object side thereof to an image plane side thereof, a front group including a first front group with a center axis thereof as center and a second front group with a center axis thereof arranged parallel with the center axis of the first front group as center, a front deflection group located on an image plane side of at least one of the first front group and the second front group, and a rear group that is located on the image plane side of the front group and the front deflection group and has a single center axis, wherein:

a first light beam exiting out of an object passes through at least the first front group and the rear group for incidence on an image plane, a second light beam exiting out of an object passes through at least the second front group and the rear group for incidence on an image plane, at least one of the first light beam and the second light beam passes through the front deflection group, and upon projection of the first light beam and the second light beam onto a section that is orthogonal to a plane including the center axis of the first front group and the center axis of the second front group and includes the center axis of the rear group, the front deflection group deflects the light beams in mutually different directions.

BRIEF DESCRIPTION OF DRAWINGS

FIGS. 13A and 13B are sectional views of the stereoscopic imaging optical system according to one embodiment of the invention as viewed from a direction orthogonal to FIG. 12.

FIG. 22 is a sectional view of the stereoscopic imaging optical system according to Example 4 as taken along its center axis.

FIGS. 23A and 23B are sectional views of the stereoscopic imaging optical system according to one embodiment of the invention as viewed from a direction orthogonal to FIG. 22.

DESCRIPTION OF EMBODIMENTS

The stereoscopic imaging optical system 1 described herein is now explained.

Suppose now that stereoscopic viewing is implemented at an object point distance of about a few mm to about 100 mm. In order for the viewer to obtain natural images without feeling a sense of discomfort, it is usually preferable to make sure a parallax amount enough for binocular viewing work. For instance, when a viewer whose interpupillary distance is 6 cm looks stereoscopically at an object from a distance of 50 mm, there will be a vergence angle of about 7°. With a stereoscopic imaging optical system designed for the viewer whose interpupillary distance is 6 cm to implement magnified viewing at a distance of 20 mm, therefore, it is necessary to bring an optical axis separation close to about 2.4 mm to obtain a vergence angle of about 7°. However, simple arrangement of two imaging optical systems will result in a failure of stereoscopic viewing, or vertical arrangement of left and right imaging areas by means of a prism will end up with an increase in the size of the optical system because of the need for using multiple prisms.

For this reason, the present invention provides a stereoscopic imaging optical system that is capable of obtaining stereoscopic images at a wide horizontal angle of view albeit having smaller size and higher resolution.

Figure 1:
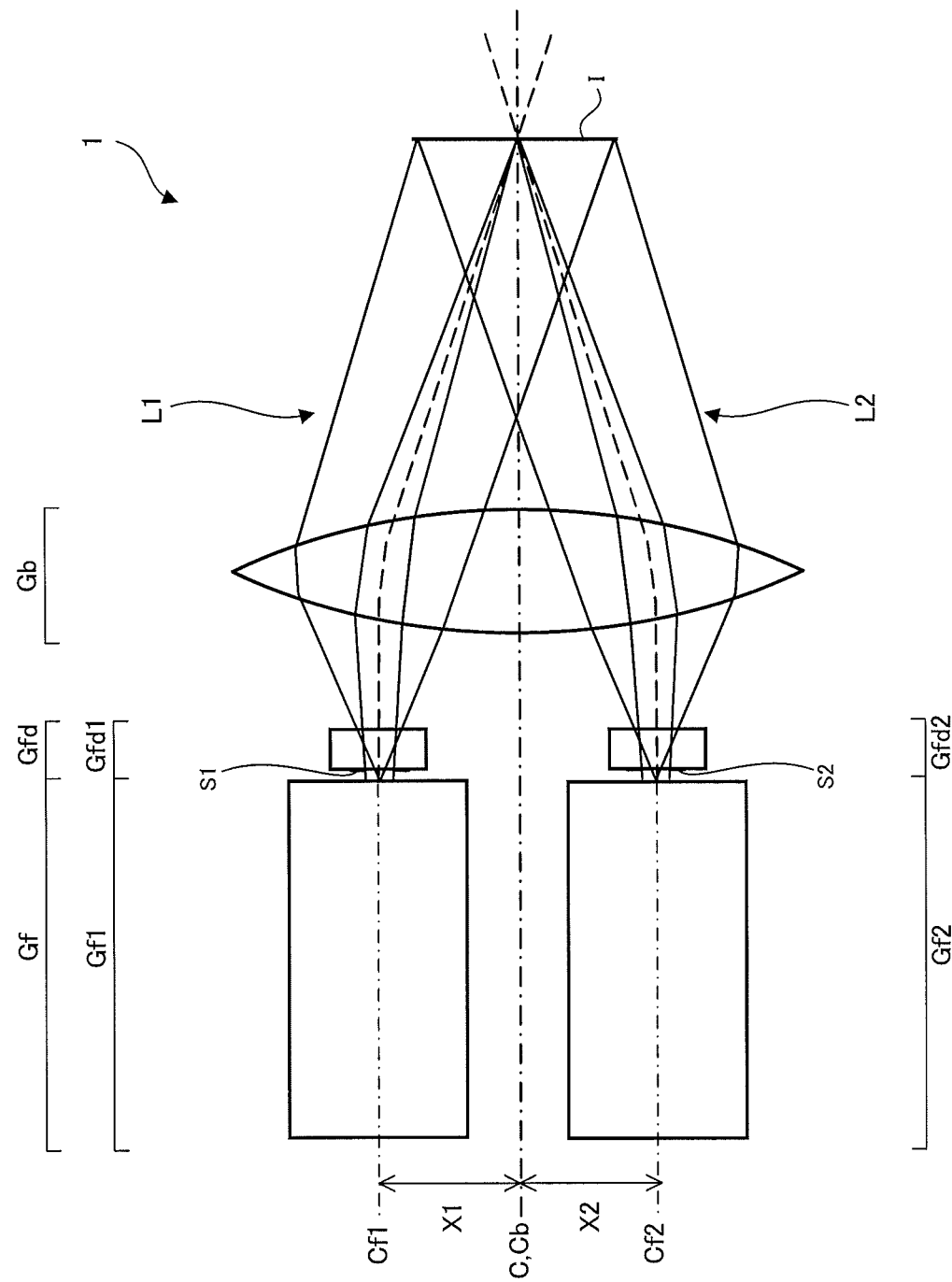
FIG. 1 is a sectional view of the stereoscopic imaging optical system according to one embodiment of the invention as viewed from one direction along its center axis.
Figure 2A:
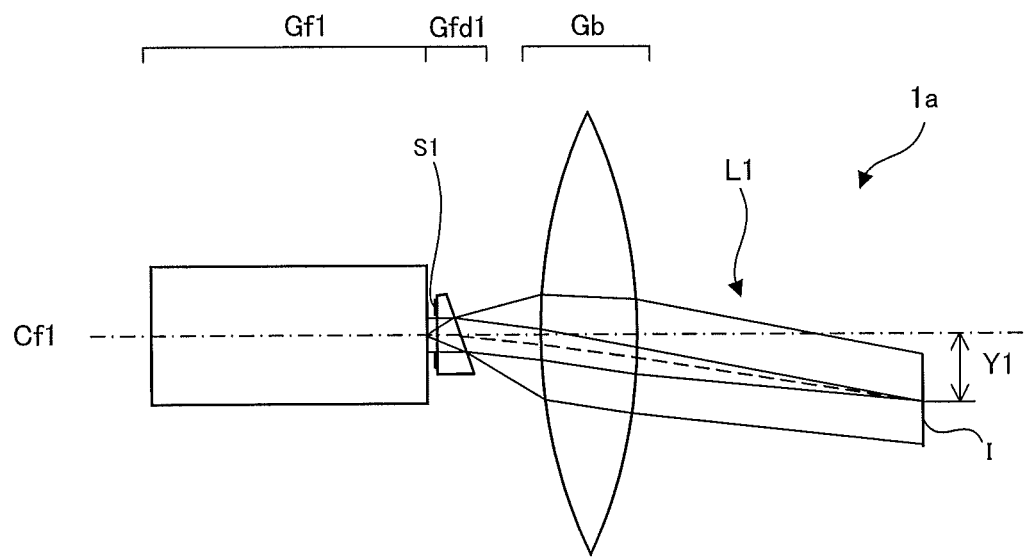
FIGS. 2A and 2B are sectional views of the stereoscopic imaging optical system according to one embodiment of the invention as viewed from a direction orthogonal to FIG. 1.
Figure 2B:
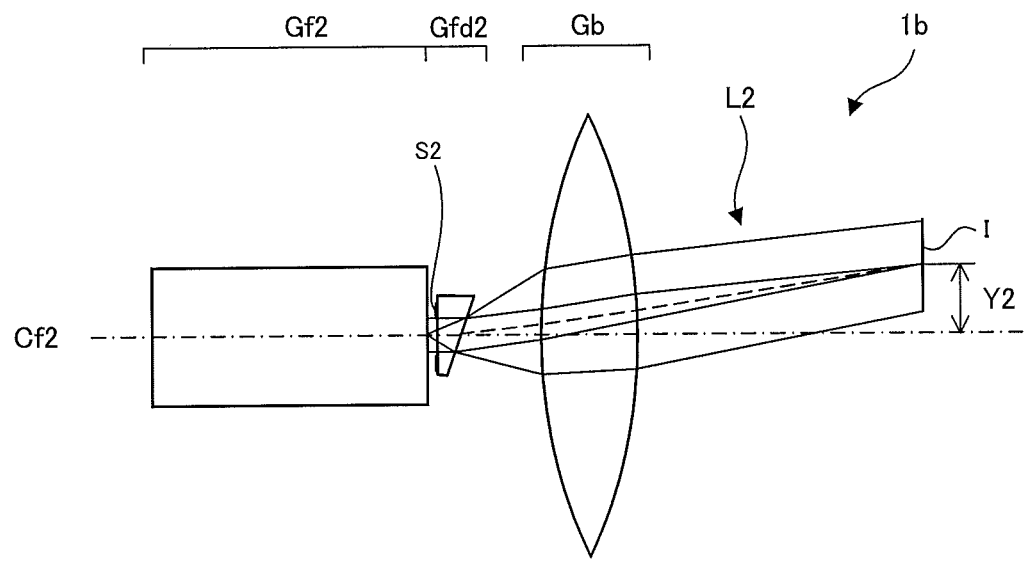
Figure 3:
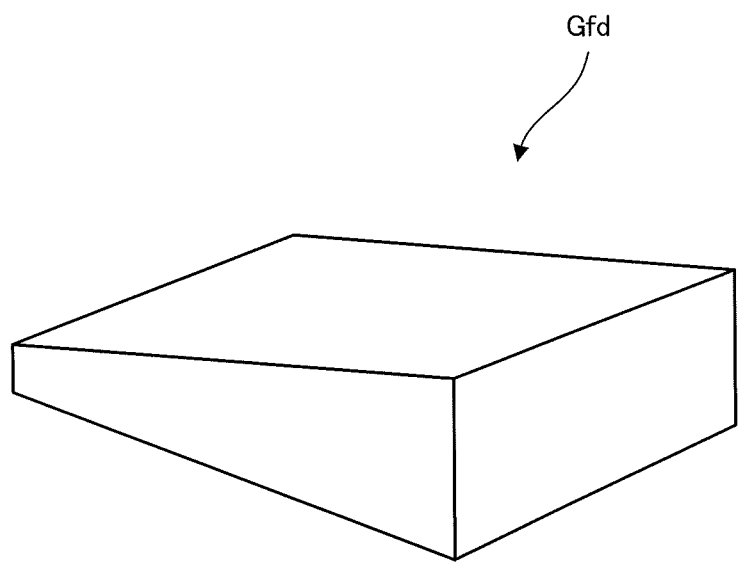
FIG. 3 is illustrative in conception of the front deflection group in the stereoscopic imaging optical system according to one embodiment of the invention.
Figure 4:
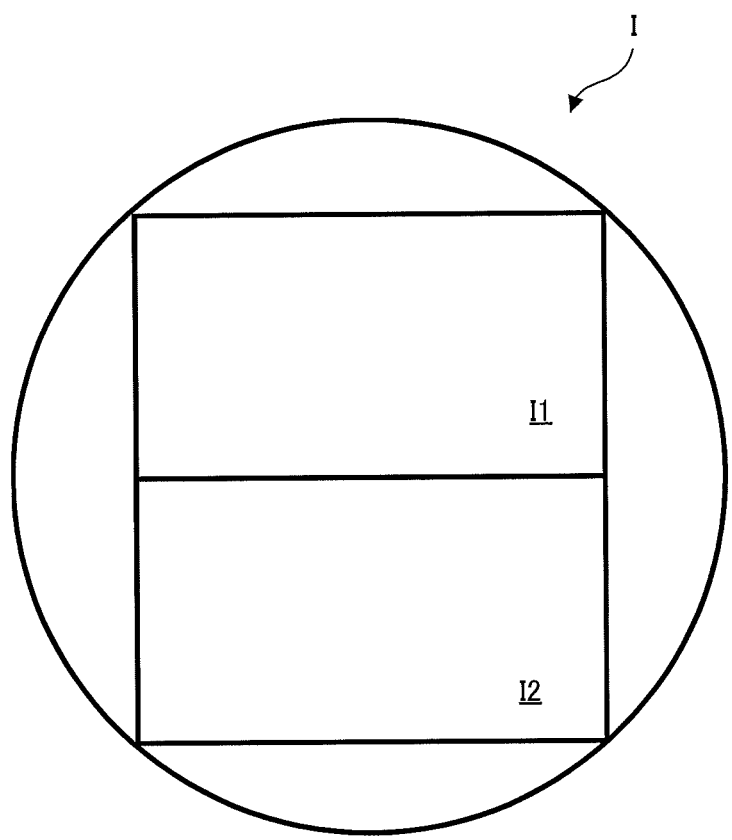
FIG. 4 is illustrative in conception of the image plane of the stereoscopic imaging optical system according to one embodiment of the invention.

FIG. 1 is a sectional view of the stereoscopic imaging optical system according to one embodiment of the invention as viewed from one direction along its center axis. FIGS. 2A and 2B are sectional views of the stereoscopic imaging optical system according to one embodiment of the invention as viewed from a direction orthogonal to FIG. 1. Specifically, FIG. 2A is indicative of an optical path taken by a first light beam and FIG. 2B is indicative of an optical path taken by second light beam. FIG. 3 is illustrative in conception of the front deflection group in the stereoscopic imaging optical system according to one embodiment of the invention. FIG. 4 is illustrative in conception of the image plane of the stereoscopic imaging optical system according to one embodiment of the invention.

Preferably in the embodiment described herein, the stereoscopic imaging optical system 1 includes, in order from an object side thereof to an image plane side thereof, a front group Gf including a first front group Gf1 with a center axis Cf1 thereof as center and a second front group Gf2 with a center axis thereof arranged parallel with the center axis Cf1 of the first front group as center, a front deflection group Gfd located on an image plane I side of at least one of the first front group Gf1 and the second front group Gf2, and a rear group Gb that is located on the image plane I side of the front group Gf and the front deflection group Gfd and has a single center axis Cb, wherein a first light beam L1 exiting out of an object passes through at least the first front group Gf1 and the rear group Gb for incidence on the image plane I, a second light beam L2 exiting out of an object passes through at least the second front group Gf2 and the rear group Gb for incidence on the image plane I, and upon projection of the first light beam L1 and the second light beam L2 onto a section that is orthogonal to a plane including the center axis Cf1 of the first front group and the center axis Cf2 of the second front group and includes the center axis Cb of the rear group, the front deflection group Gfd deflects the light beams in mutually different directions. Note here that the "defection" means the one caused by refraction.

In the stereoscopic imaging optical system 1 described herein, the left and right images having a wide horizontal angle of view are deflected in the vertical direction such that they are efficiently formed in a small imaging area. To this end, the front deflection group Gfd deflects at least one of the two light beams L1 and L2 passing through the two front groups Gf in a different direction to enter it in the single rear group Gb for image formation.

Referring to one reason the front group Gf includes the first front group Gf1 with the center axis Cf1 of the first front group as center and the second front group Gf2 with the center axis Cf2 of the second front group arranged parallel with the center axis Cf1 of the first front group as center, when the front group Gf has a single center axis, the entrance pupil must be divided into two to obtain stereoscopic images, and with an increasing angle of view, a great deal of rotationally asymmetric image distortion will occur rendering stereoscopic viewing impossible because the entrance pupil is decentered. Another reason is that the entrance pupil to be divided is located at the front group Gf having a single center axis, resulting in an increase in the outer diameter of the front group Gf.

Referring to the reason the rear group Gb has a single center axis Cb, the imaging areas must be located adjacent to each other. If the rear group Gb is designed as having two center axes, the outer diameter of the optical system inclusive of a lens frame will be larger than the imaging areas. Even when the two center axes of the rear group are positioned adjacent to each other, the left and right images will space away from each other, resulting in an increase in the imaging areas including both eyes.

In the embodiment described herein, the front deflection group Gfd is interposed between the front group Gf and the rear group Gb, and located such that upon projection of the first light beam L1 and the second light beam L2 onto a section that is orthogonal to a plane including the center axis Cf1 of the first front group and the center axis Cf2 of the second front group and includes the center axis Cb of the rear group, they are deflected in mutually different directions. As shown typically in FIG. 3, the front deflection group Gfd should include an optical element in a wedge prism form.

Upon projection of the first light beam L1 exiting out of the first front group Gf1 and the second light beam L2 exiting out of the second front group Gf2 onto a section that is orthogonal to a plane including the center axis Cf1 of the first front group and the center axis Cf2 of the second front group and includes the center axis Cb of the rear group, they are diffracted by the front deflection group Gfd in mutually different directions and then imaged on the image plane I via the rear group Gb.

It is thus possible to image the first light beam L1 and the second light beam L2 in any position on the image plane I and, hence, to make efficient use of the imaging areas. It is accordingly possible to provide a stereoscopic imaging optical system that is capable of obtaining stereoscopic images having a wide horizontal angle of view albeit having smaller size and higher resolution.

It is here to be noted that the front deflection group Gfd may include at least one of the first front deflection group Gfd1 and the second front deflection group Gfd2.

Preferably in the stereoscopic imaging optical system 1 described herein, the front deflection group Gfd includes the first front deflection group Gfd1 located on the image plane I side of the first front group Gf1 and the second front deflection group Gfd2 located on the image plane I side of the second front group Gf2; the first light beam L1 exiting out of an object passes through at least the first front group Gf1, first front deflection group Gfd1 and rear group Gb and the second light beam L2 exiting out of an object passes through at least the second front group Gf2, second front deflection group Gfd2 and rear group Gb; and upon projection of the first light beam L1 and second light beam L2 onto a section that is orthogonal to a plane including the center axis Cf1 of the first front group and the center axis Cf2 of the second front group and includes the center axis Cb of the rear group, they are mutually deflected in directions spaced away from the center axis Cb of the rear group Gb.

Such construction makes it possible just only to reduce burdens of the rear group Gb on correction of aberrations but also to adjust the deflection of the respective light beams L1 and L2 individually. Note here that the first front deflection group Gfd1 may be integral with the second front deflection group Gfd2.

Preferably in the stereoscopic imaging optical system 1 described herein, the front deflection group Gfd deflects the first light beam L1 and second light beam L2 in directions symmetrical with respect to the center axis Cb of the rear group upon projection of them onto a section that is orthogonal to a plane including the center axis Cf1 of the first front group and the center axis Cf2 of the second front group and includes the center axis Cb of the rear group.

As shown in FIG. 4, such construction enables imaging areas I1 and I2 for the first light beam L1 and second light beam L2 incident horizontally parallel on the front group Gf to be vertically arranged in an efficient way for the image plane I. Note here that the vertically arranged imaging areas I1 and I2 may be spaced away from each other in such a way as to prevent a light beam leaking out of one imaging area from mixing with another imaging area.

Preferably in the stereoscopic imaging optical system 1 described herein, the first front group Gf1 and second front group Gf2 include a first stop S1 and a second stop S2, respectively, through which a part of the first light beam L1 and second light beam L2 passes, and the front deflection group Gfd is located adjacent to at least one of the first stop S1 and second stop S2.

The first front deflection group Gfd1 and second front deflection group Gfd2 are located adjacent to the first stop S1 and second stop S2, respectively, so that the first front deflection group Gfd1 and second front deflection group Gfd2 can be of smaller size. In addition, there is less interference of the first light beam L1 with the second light beam L2, resulting in capability of obtaining images having a wide angle of view.

Preferably, the stereoscopic imaging optical, system 1 described herein satisfies the following condition (1):

$$0 \leq d/f < 5 \tag{1}$$

where d is a distance from the front deflection group Gfd to the stop S, and f is a focal length of the whole optical system.

Figure 5A:
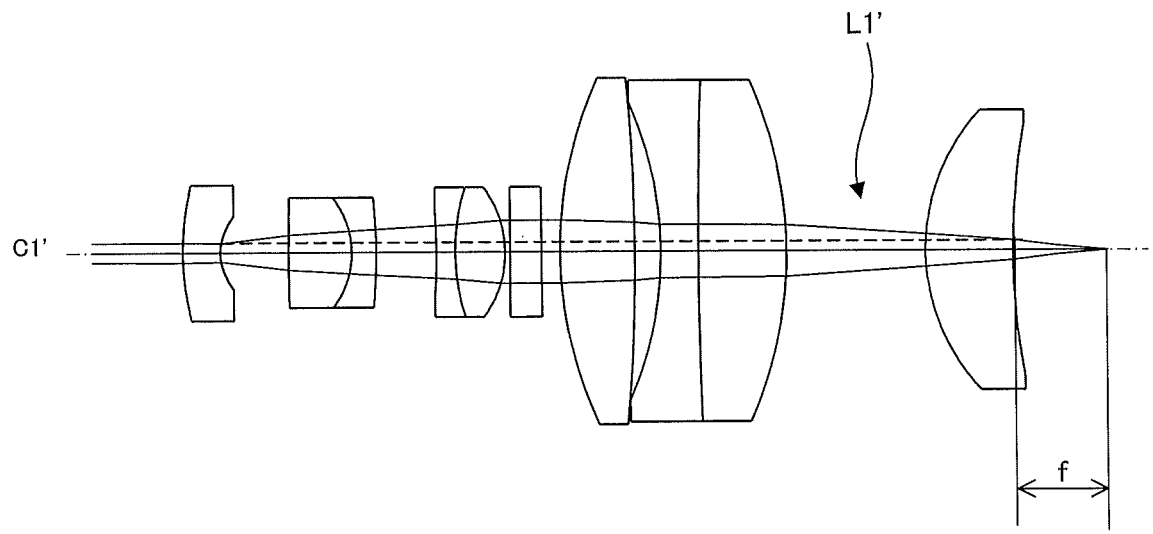
FIGS. 5A and 5B are illustrative in conception of the focal length of the stereoscopic imaging optical system according to one embodiment of the invention.
Figure 5B:
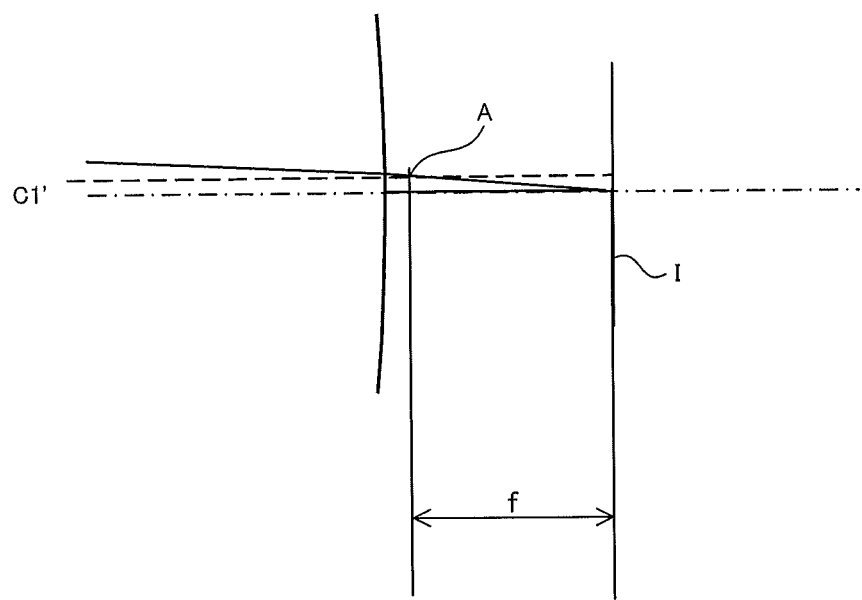
Figure 6:
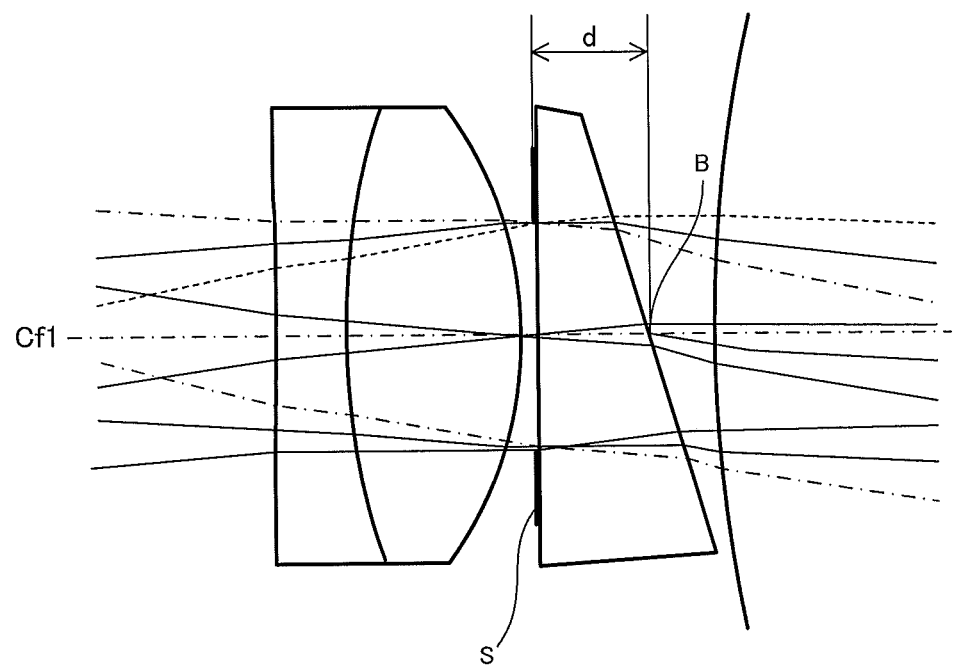
FIG. 6 is indicative of the distance of the stereoscopic imaging optical system according to one embodiment of the invention from the deflection group to the stop.

FIGS. 5A and 5B are illustrative in conception of the focal length of the stereoscopic imaging optical system according to one embodiment of the invention, and FIG. 6 is indicative of the distance of the stereoscopic imaging optical system according to one embodiment of the invention from the deflection group to the stop.

In the embodiment described herein, the focal length of the whole stereoscopic imaging optical system 1 is defined by f as depicted in FIGS. 5A and 5B. In the case where the stereoscopic imaging optical system 1 takes the form of a decentered optical system, parallel light beams are incident from an infinity on the stereoscopic imaging optical system 1 after removal of decentration, and an axial marginal light ray L1' incident on the stereoscopic imaging optical system 1 exits out of the optical system 1 after passing through the optical system 1, arriving at a position A where it bends virtually. The focal length f of this optical system 1 is here provided by the distance from the position A to the image plane I.

In the embodiment described herein, the distance of the stereoscopic imaging optical system 1 from the front deflection group Gfd to the stop S is defined by d as depicted in FIG. 6. Assume here that the reference position of the front deflection group Gfd to define the distance d is typically provided by a point of intersection B of the center axis Cf1 of the first front group with the most image side surface of the front deflection group Gfd.

Exceeding the upper limit to condition (1) renders it impossible to obtain stereoscopic viewing images having a wide angle of view.

It is here to be noted that the stereoscopic imaging optical system 1 described herein should more preferably satisfy the following condition (1'):

$$0 \leq d/f \leq 3 \quad (1')$$

Satisfaction of Condition (1') makes it possible to obtain stereoscopic-view images having a wide angle of view.

In the embodiment described herein, the separation between the center axis Cf1 of the first front group and the center axis Cf2 of the second front group, in other words, the exit pupil separation is preferably wider than the separation between the center of the first light beam L1 on the image plane I and the center of the second light beam L2 on the image plane I.

To put it another way, it is preferable that the sum X1+X2 of a separation X1 between the center axis Cf1 of the first front group and the center axis C of the whole optical system and a separation X2 between the center axis Cf2 of the second front group and the center axis C of the whole optical system, as shown in FIG. 1, is preferably larger than the sum Y1+Y2 of a separation Y1 between the center of the first light beam L1 on the image plane I and the center axis C of the whole optical system and a separation Y2 between the center of the second light beam L2 on the image plane I and the center axis C of the whole optical system, as shown in FIG. 2.

Such construction permits the whole optical system to be of smaller size.

Figure 7:
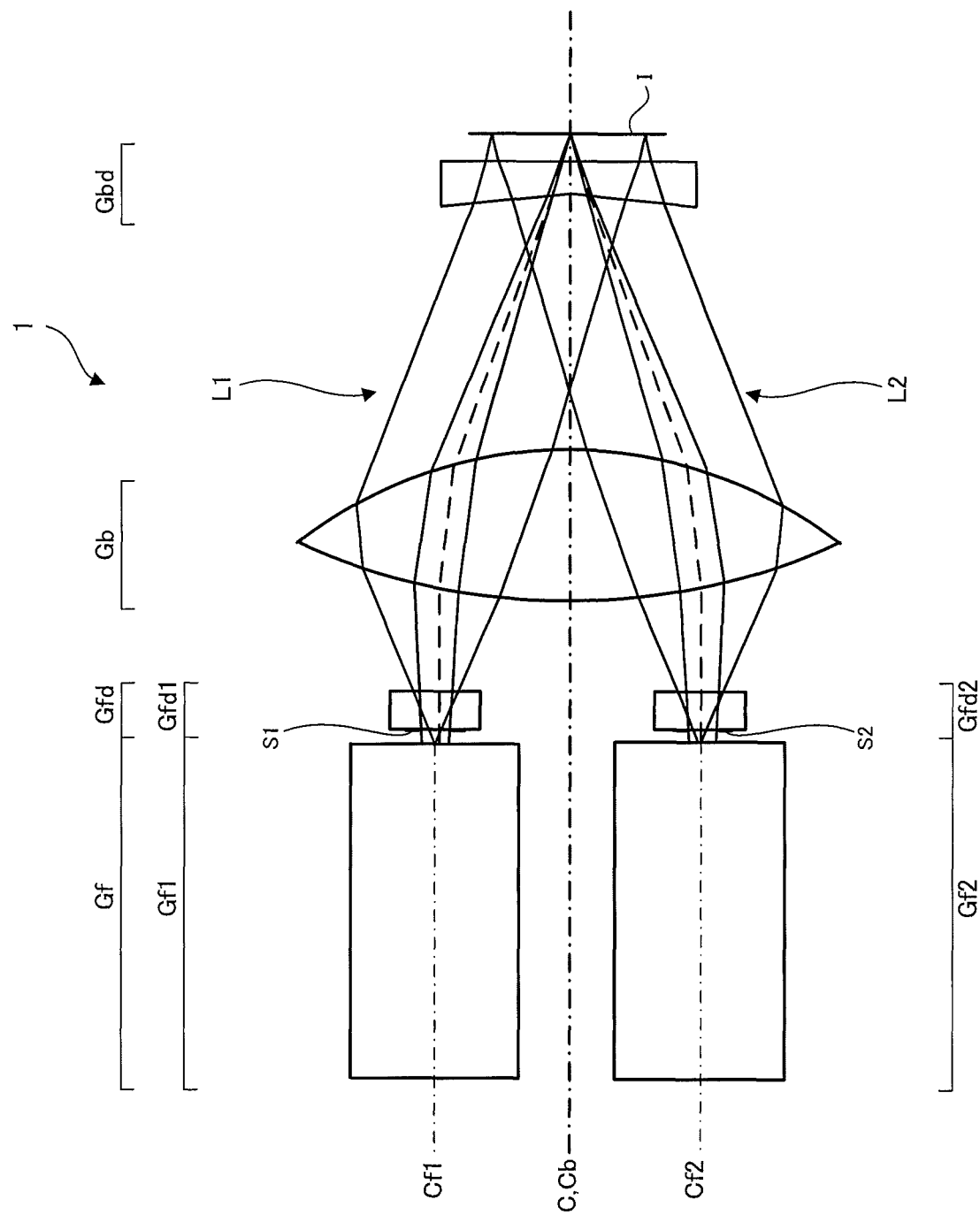
FIG. 7 is a sectional view of the stereoscopic imaging optical system according to one embodiment of the invention as viewed from one direction along its center axis.

FIG. 7 is a sectional view of the stereoscopic imaging optical system according to one embodiment of the invention as viewed from one direction along its center axis.

In the embodiment described herein, there is preferably a rear deflection group Gbd interposed between the rear group Gb and the image plane I for deflection of the first light beam L1 and second light beam L2. This rear deflection Gbd deflects the first light beam L1 and second light beam L2 after passing through the rear group Gb symmetrically with respect to the center axis Cb of the rear group such that the angles of incidence of the first light beam L1 and second light beam L2 on the image plane I come close to the perpendicular.

As the light beams L1 and L2 are deflected such that their angles of incidence on the image plane I come close to the perpendicular, it is compatible with high-resolution, high-sensitivity imaging devices having incident angle characteristics.

In the embodiment described herein, the rear deflection group Gbd preferably includes a first rear deflection group Gbd1 for deflection of the first light beam L1 and a second rear deflection group Gbd2 for deflection of the second light beam L2.

Figure 8:
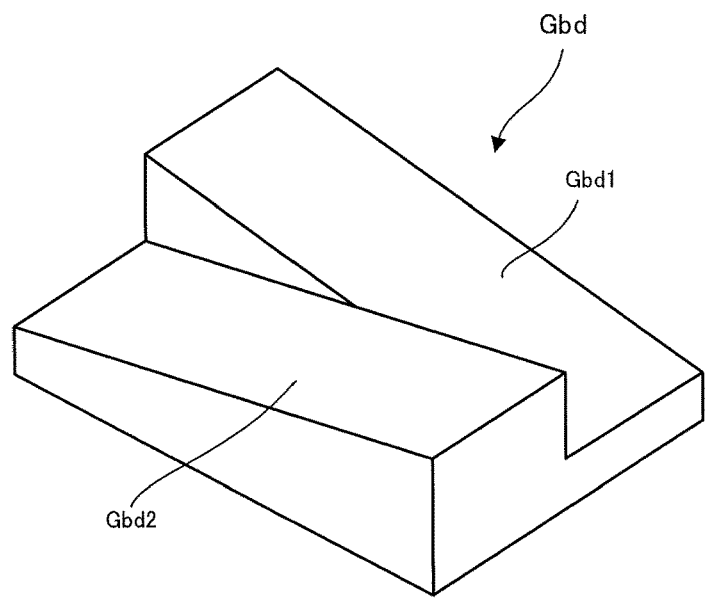
FIG. 8 is illustrative of an example of the rear deflection group in the stereoscopic imaging optical system according to one embodiment of the invention.
Figure 9A:
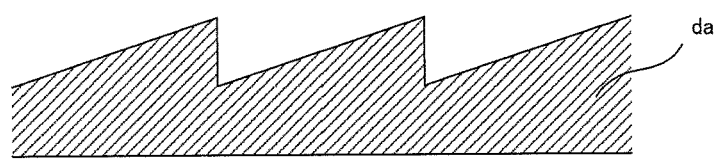
FIGS. 9A-9D are illustrative of an example of the diffractive optical element in the stereoscopic imaging optical system according to one embodiment of the invention.
Figure 9B:
Figure 9C:
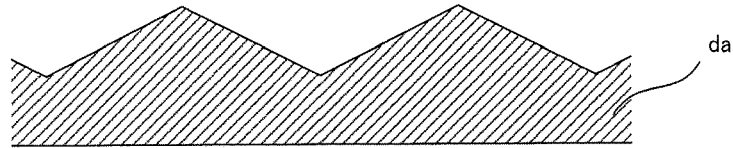
Figure 9D:
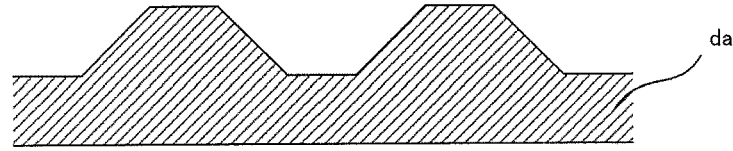

FIG. 8 is illustrative of an example of the rear deflection group in the stereoscopic imaging optical system according to one embodiment of the invention.

With the rear deflection group Gbd including the first rear deflection group Gbd1 and second rear deflection group Gbd2 as depicted in FIG. 8, it is possible to adjust the deflection of the respective light beams separately. Note here that the first rear deflection group Gbd1 may be separate from the second rear deflection group Gbd2 or, alternatively, they may be formed as an integral group as depicted in FIG. 8.

In the embodiment described herein, the rear deflection group Gbd preferably includes an optical element in a wedge prism form.

It is then possible to construct the wedge prism form optical element in the rear deflection group Gbd of a planar surface, resulting in facility in the production of the rear deflection group Gbd.

In the embodiment described herein, the rear deflection group Gbd preferably includes a diffractive optical element.

FIGS. 9A-9D are illustrative of an example of the diffractive optical element in the stereoscopic imaging optical system according to one embodiment of the invention.

As can be seen from FIGS. 9A-9D, the diffractive optical element da may have any desired shape. Thus, the incorporation of the diffractive optical element da into the rear deflection group Gbd holds the occurrence of field tilt and coma back, and renders the optical system more compact.

In the embodiment described herein, the rear deflection group Gbd preferably includes an optical element having a curved surface.

By the incorporation of the optical element having a curved surface into the rear deflection group Gbd, it is possible to set the angle of light rays incident on the image plane in a more flexible way. This also enables a telecentric arrangement wherein after exiting out of the rear group, chief rays for each image height travel in parallel while, at the same time, introduces improvements in field curvature. Note here that the "curved surface" may be a spherical surface, a toric surface, an anamorphic surface, or a free-form surface.

In the stereoscopic imaging optical system 1 described herein, the front deflection group Gfd preferably includes a deflection member capable of achromatization.

By use of the deflection member capable of achromatization, it is possible to improve on resolving power while holding the occurrence of chromatic aberrations back.

In the stereoscopic imaging optical system 1 described herein, the deflection member preferably includes two optical elements db1 and db2 taking the form of a wedge prism and having varying Abbe constants.

Figure 10:
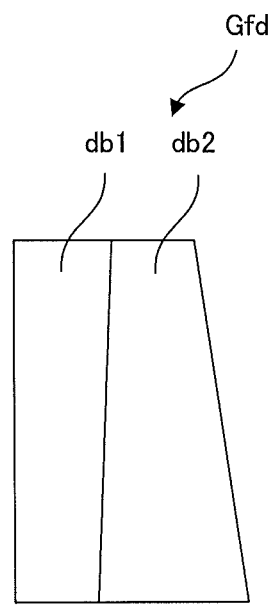
FIG. 10 is illustrative of two optical elements, each in a wedge prism form, in the stereoscopic imaging optical system according to one embodiment of the invention.

FIG. 10 is illustrative of two optical elements, each in a wedge prism form, in the stereoscopic imaging optical system 1 according to one embodiment of the invention.

As depicted in FIG. 10, the two optical elements db1 and db2 each in a wedge prism form are preferably cemented together for use. By use of the two optical elements db1 and db2 taking the form of a wedge prism and having different Abbe constants, it is possible to improve on resolving power while holding the occurrence of chromatic aberrations back.

In the stereoscopic imaging optical system 1 described herein, the deflection member preferably includes a single optical element db in a wedge prism form and a diffractive optical element da.

Figure 11:
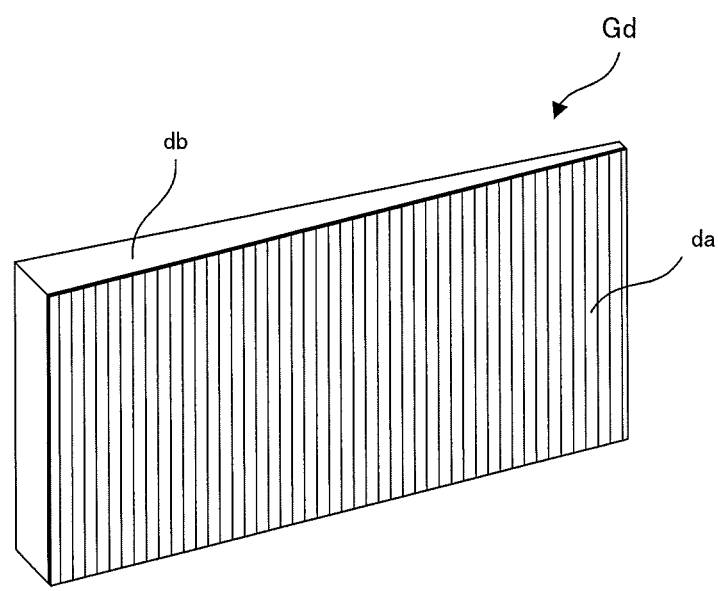
FIG. 11 is illustrative of a wedge prism and a diffractive optical element in the stereoscopic imaging optical system according to one embodiment of the invention.

FIG. 11 is illustrative of the wedge prism and diffractive optical element in the stereoscopic imaging optical system according to one embodiment of the invention.

As shown in FIG. 11, the single wedge prism-form optical element db and diffractive optical element da are preferably cemented together for use. Note here that the diffractive optical element da may have any desired shape, as depicted in FIGS. 9A-9D.

By use of the single wedge prism-form optical element db and diffractive optical element da, it is possible to improve on resolving power while holding the occurrence of chromatic aberrations back, and to shorten the overall length of the stereoscopic imaging optical system as well.

It is here to be understood that when the deflection member is made up of such a wedge prism-form optical element, it is preferable that there is a parallel light beam between the front group Gf and the rear group Gb. The parallel light beam here means that there is an object position at an infinity distance with an axial marginal light ray parallel with the center axis. With a parallel light beam between the front group Gf and the rear group Gb, it is possible to reduce coma produced at the wedge prism-form optical element.

Further, at least one lens in the rear group Gb may be designed in such a way as to move in the rear group's center axis Cb direction. Thus, as at least one lens in the rear group Gb is designed in such a way as to move in the rear group's center axis Cb direction, it permits focusing function to be compatible with a high-pixel imaging device.

Still further, the front deflection group Gfd, and the rear deflection group Gbd may be formed of a deflection member having a free-form surface. By use of the free-form surface, burdens of the rear group Gb on correction of aberrations are eased, enabling imaging operation with an increasing resolving power.

The surface shape of the free-form surface FFS used in the embodiment described herein is defined by the following formula (a). Note here that the Z-axis of that defining formula is the axis of the free-form surface FFS, and that a coefficient term with no data described is zero.

$$Z = (r^2/R)/\left[1 + \sqrt{1 - (1+k)(r/R)^2}\right] + \sum_{j=1}^{66} C_j X^m Y^n \quad (a)$$

Here the first term of Formula (a) is the spherical term, and the second term is the free-form surface term.

In the spherical term,
R is the radius of curvature of the apex,
k is the conic constant, and
r is $\sqrt{X^2+Y^2}$.

The free-form surface term is:

$$\sum_{j=1}^{66} C_j X^m Y^n = C_1 + C_2 X + C_3 Y + C_4 X^2 + C_5 XY + C_6 Y^2 + C_7 X^3 +$$
$$C_8 X^2 Y + C_9 XY^2 + C_{10} Y^3 + C_{11} X^4 + C_{12} X^3 Y + C_{13} X^2 Y^2 +$$
$$C_{14} XY^3 + C_{15} Y^4 + C_{16} X^5 + C_{17} X^4 Y + C_{18} X^3 Y^2 + C_{19} X^2 Y^3 +$$
$$C_{20} XY^4 + C_{21} Y^5 + C_{22} X^6 + C_{23} X^5 Y + C_{24} X^4 Y^2 + C_{25} X^3 Y^3 +$$
$$C_{26} X^2 Y^4 + C_{27} XY^5 + C_{28} Y^6 + C_{29} X^7 + C_{30} X^6 Y + C_{31} X^5 Y^2 +$$
$$C_{32} X^4 Y^3 + C_{33} X^3 Y^4 + C_{34} X^2 Y^5 + C_{35} XY^6 + C_{36} Y^7 \ldots$$

where $C_j$ (j is an integer of 1 or greater) is a coefficient.

It is here to be noted that the defining formula (a) is provided for the purpose of illustration alone. The free-form surface according to the invention has a feature of using a rotationally asymmetric surface thereby making correction for rotationally asymmetric aberrations occurring from decentration while, at the same time, improving assembling capabilities. As a matter of course, the same effect is achievable for any other defining formula too.

Examples 1 to 7 of the optical system 1 according to the embodiment described herein are now explained. Note here that numeral data about Examples 1-4, 6 and 7 will be given later, but numeral data about Example 5 will be left out.

A coordinate system is defined for each surface. A direction from the origin 0 of the coordinate system, by which that surface is defined, toward the image plane along each center axis is defined as a Z-axis positive direction, and a direction from the center axis Cf2 of the second front group toward the center axis Cf1 of the first front group on the same surface is defined as an X-axis positive direction. Further, a Y-axis positive direction is defined by the right-hand coordinate system.

Figure 12:
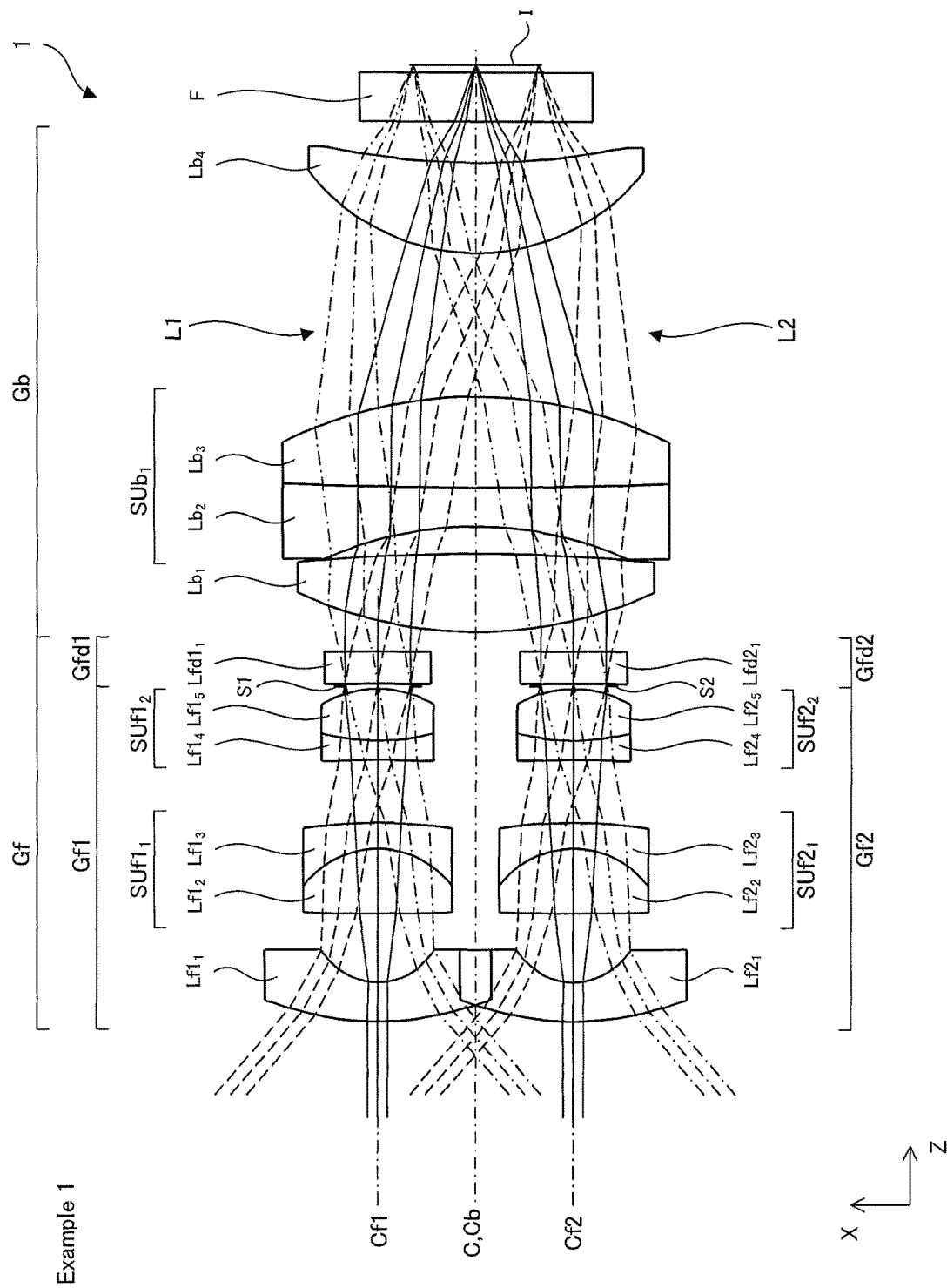
FIG. 12 is a sectional view of the stereoscopic imaging optical system according to Example 1 as taken along its center axis C.
Figure 14:
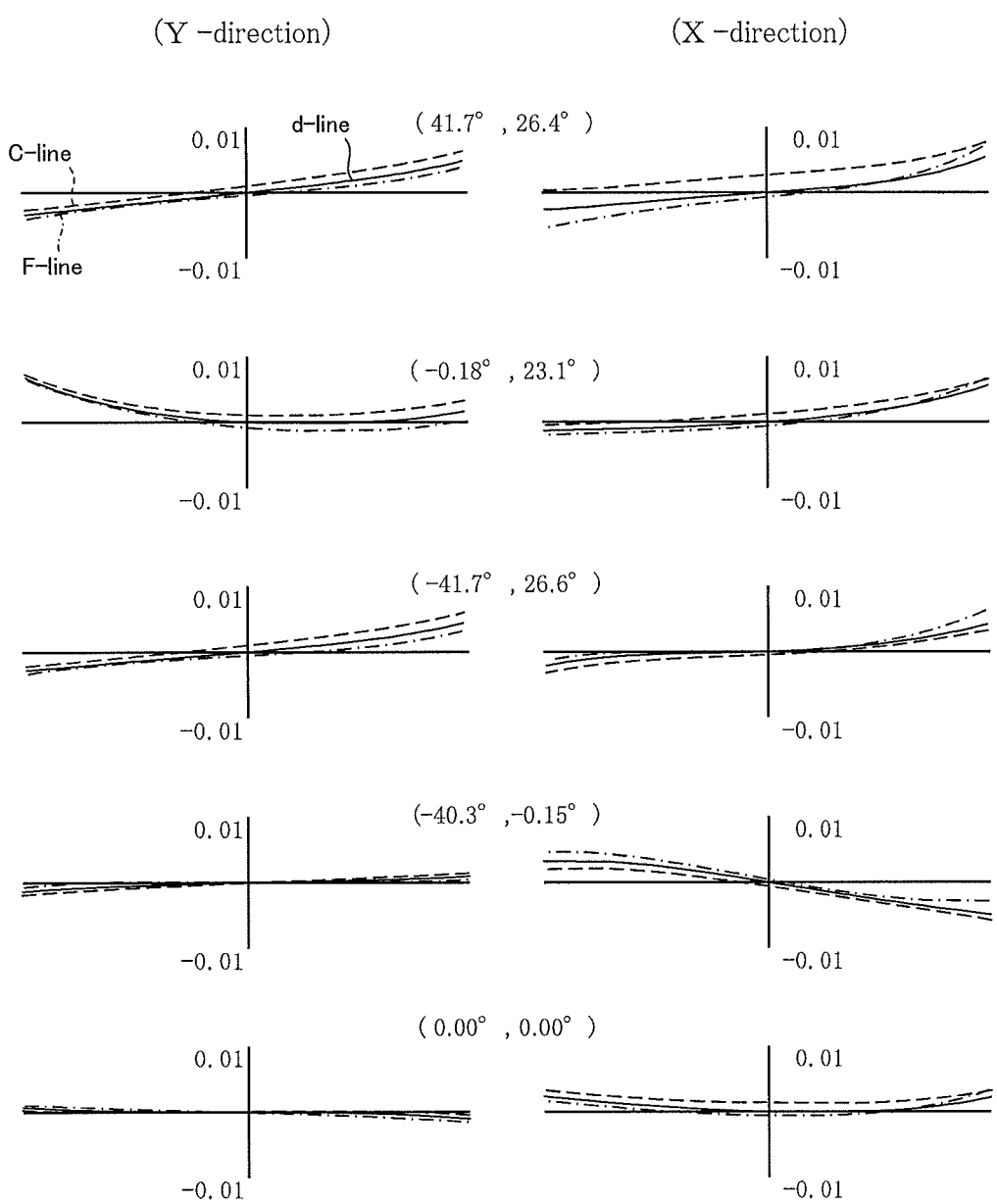
FIG. 14 is a transverse aberration diagram for the stereoscopic imaging optical system according to Example 1.
Figure 15:
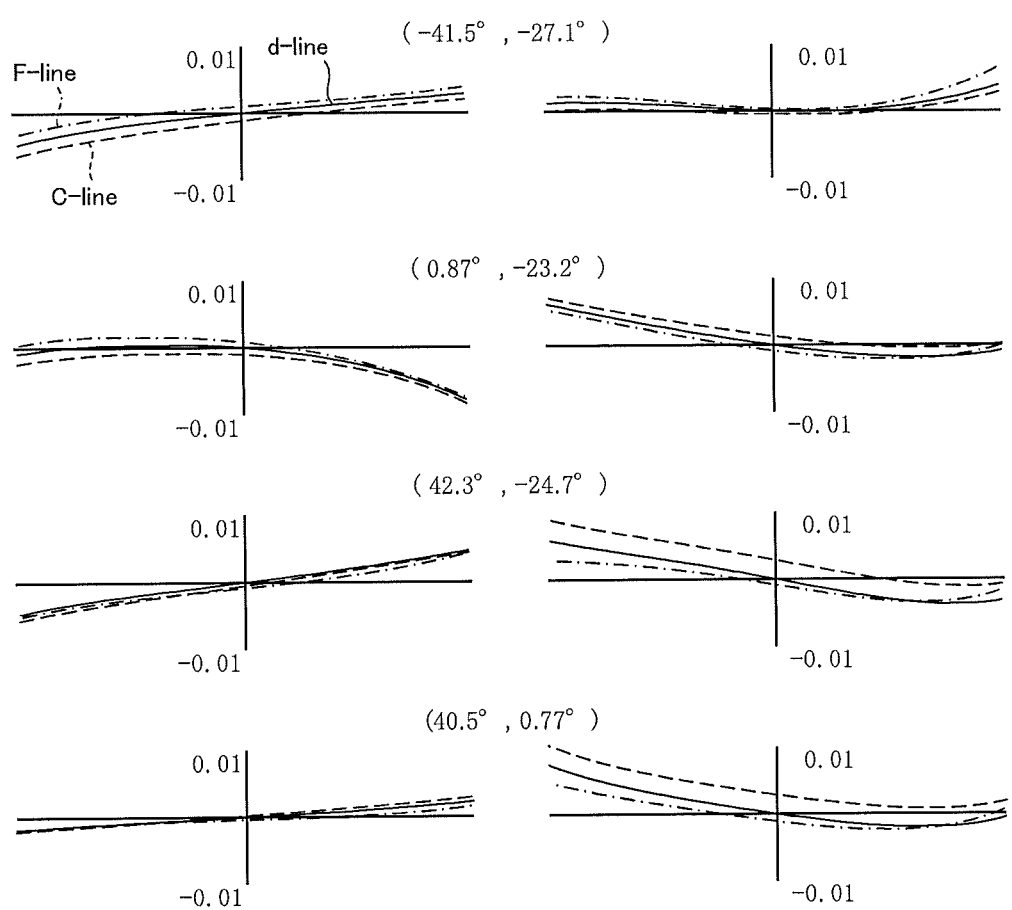
FIG. 15 is a transverse aberration diagram for the stereoscopic imaging optical system according to Example 1.

FIG. 12 is a sectional view of the stereoscopic imaging optical system 1 according to Example 1 as taken along its center axis C, and FIGS. 13A and 13B are sectional views of the stereoscopic imaging optical system according to one embodiment of the invention as viewed from a direction orthogonal to FIG. 12. FIGS. 14 and 15 are transverse aberration diagrams for the stereoscopic imaging optical system 1 according to Example 1.

In the transverse aberration diagrams, the centrally indicated angle is indicative of the (angle of view in the perpendicular direction), and transverse aberrations at that angle in the Y (meridional) direction and X (sagittal) direction are shown. Note here that the minus angle of view means a clockwise angle with respect to the X-axis positive direction. The same goes for the transverse aberration diagrams for Examples 1-4, 6 and 7 with omission of transverse aberration diagrams for Example 5.

As depicted in FIGS. 12 and 13, the stereoscopic imaging optical system 1 according to Example 1 includes, in order from its object side to its image side, a front group Gf including a first front group Gf1 with its center axis Cf1 as an optical axis and a second front group Gf2 with its center axis Cf2 arranged parallel with the center axis Cf1 of the first front group as an optical axis, a front deflection group Gfd including a first front deflection group Gfd1 which the center axis Cf1 of the first front group intersects and a second front deflection group Gfd2 which the center axis Cf2 of the second front group intersects, and a rear group Gb including a single center axis Cb.

Parallel arrangement of the first and second front groups Gf1 and Gf2 makes stereoscopic viewing possible.

Preferably, the first front group Gf1 includes a negative meniscus lens $Lf1_1$ convex on the object side, a cemented lens $SUf1_1$ consisting of a double-convex positive lens $Lf1_2$ and a negative meniscus lens $Lf1_3$ convex on the image plane side, a cemented lens $SUf1_2$ consisting of a double-concave negative lens $Lf1_4$ and a double-convex positive lens $Lf1_5$, and a first stop S1.

The first front deflection group $Gfd_1$ includes an optical element $Lfd1_1$ in a wedge prism form, and is located adjacent to the first stop S1.

Preferably, the second front group, Gf2 includes a negative meniscus lens $Lf2_1$ convex on the object side, a cemented lens $SUf2_1$ consisting of a double-convex positive lens $Lf2_2$ and a negative meniscus lens $Lf2_3$ convex on the image plane side, a cemented lens $SUf2_2$ consisting of a double-concave negative lens $Lf2_4$ and a double-convex positive lens $Lf2_5$, and a second stop S2.

The second front deflection group Gfd2 includes an optical element $Lfd2_1$ in a wedge prism form, and is located adjacent to the second stop S2.

The rear group Gb includes a double-convex positive lens $Lb_1$, a cemented lens $SUb_1$ consisting of a double-concave negative lens Lb, and a double-convex positive lens $Lb_3$, and a positive meniscus lens Lb, convex on the object side.

There is further a filter F located just in front of the image plane I.

A first light beam L1 incident from the first object plane on the first front group $Gf_1$ passes through the negative meniscus lens $Lf1_1$, cemented lens $SUf1_1$, cemented lens $SUf1_2$ and first stop S1, and then exits out of the first front group Gf1, after which it enters the rear group Gb via the first front deflection group Gfd1.

A second light beam L2 incident from the second object plane on the second front group Gf$_2$ passes through the negative meniscus lens Lf2$_1$, cemented lens SUf2$_1$, cemented lens SUf2$_2$ and second stop S2, and then exits out of the second front group Gf2, after which it enters the rear group Gb via the second front deflection group Gfd2.

The first and second light beams L1 and L2 incident on the rear group Gb each pass through the double-convex positive lens Lb$_1$, cemented lens SUb$_1$, positive meniscus lens Lb$_4$ and filter F, after which they enter the image plane I.

Upon projection of the first and second light beams L1 and L2 onto a section that is orthogonal to a plane including the center axes Cf1 and Cf2 of the first and second front groups and includes the center axis Cb, the front deflection group Gfd in the stereoscopic imaging optical system 1 according to Example 1 deflects them in symmetrical directions while spacing away from the center axis Cb of the rear group.

Figure 16:
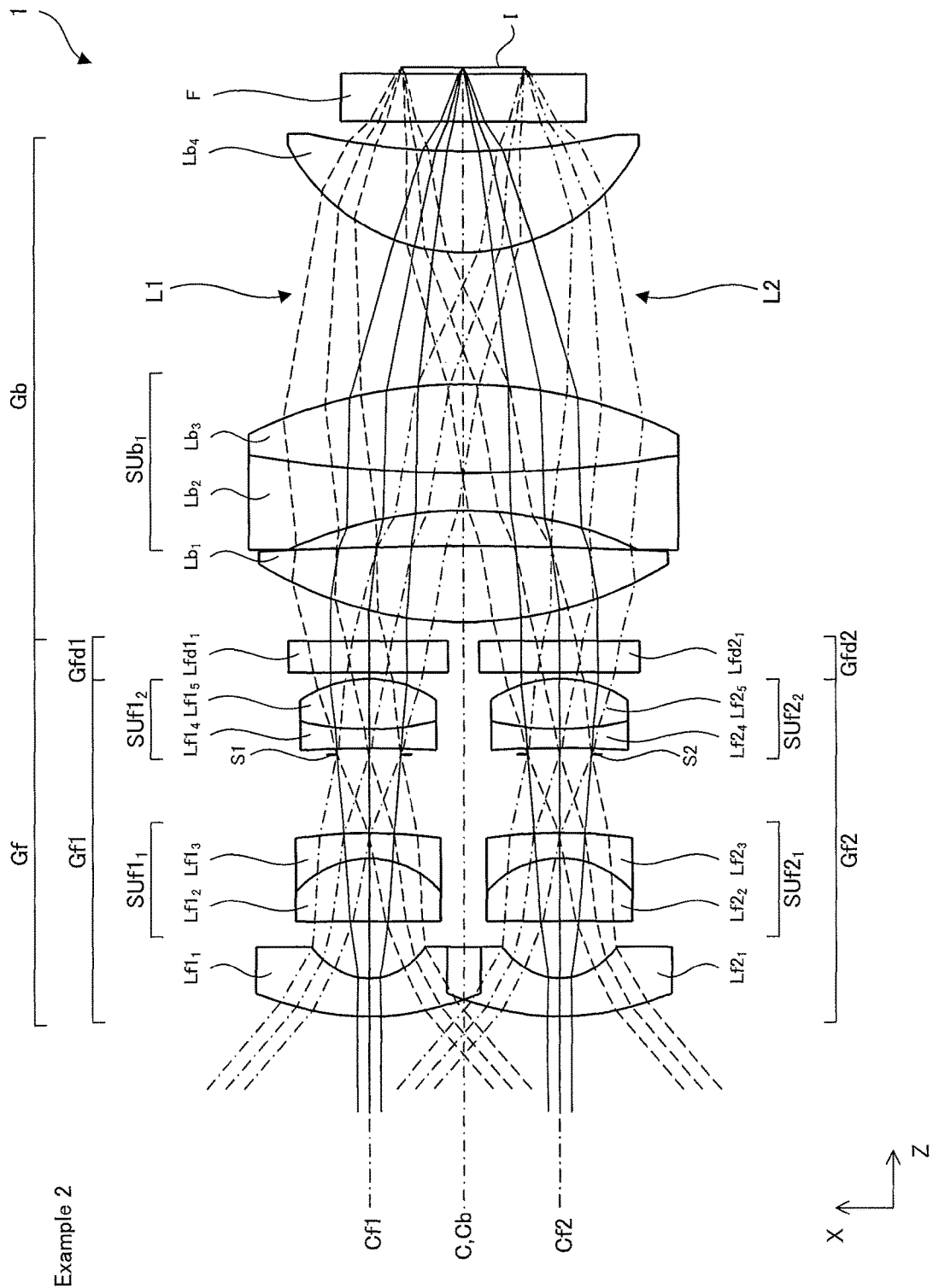
FIG. 16 is a sectional view of the stereoscopic imaging optical system according to Example 2 as taken along its center axis.
Figure 17:
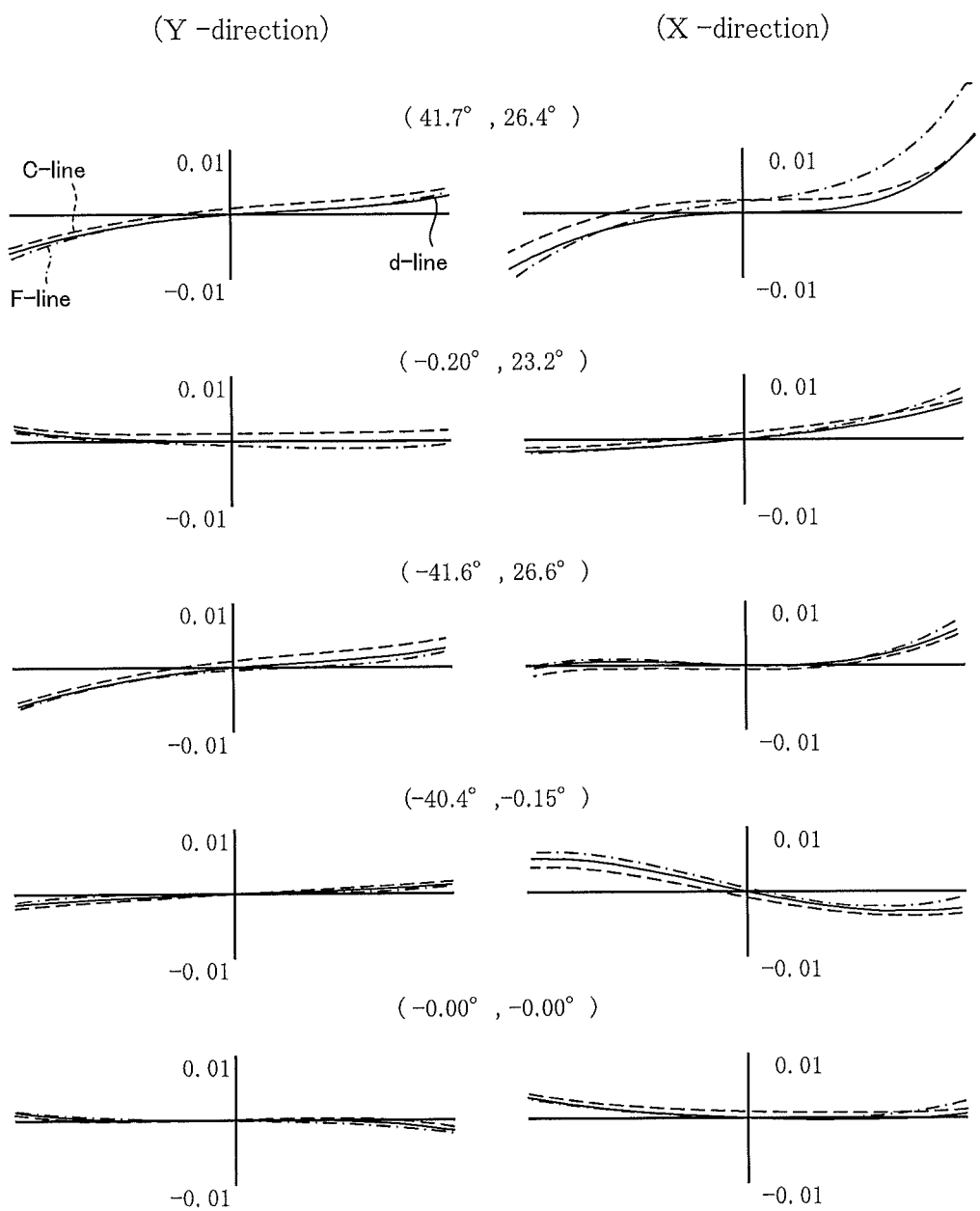
FIG. 17 is a transverse aberration diagram for the stereoscopic imaging optical system according to Example 2.
Figure 18:
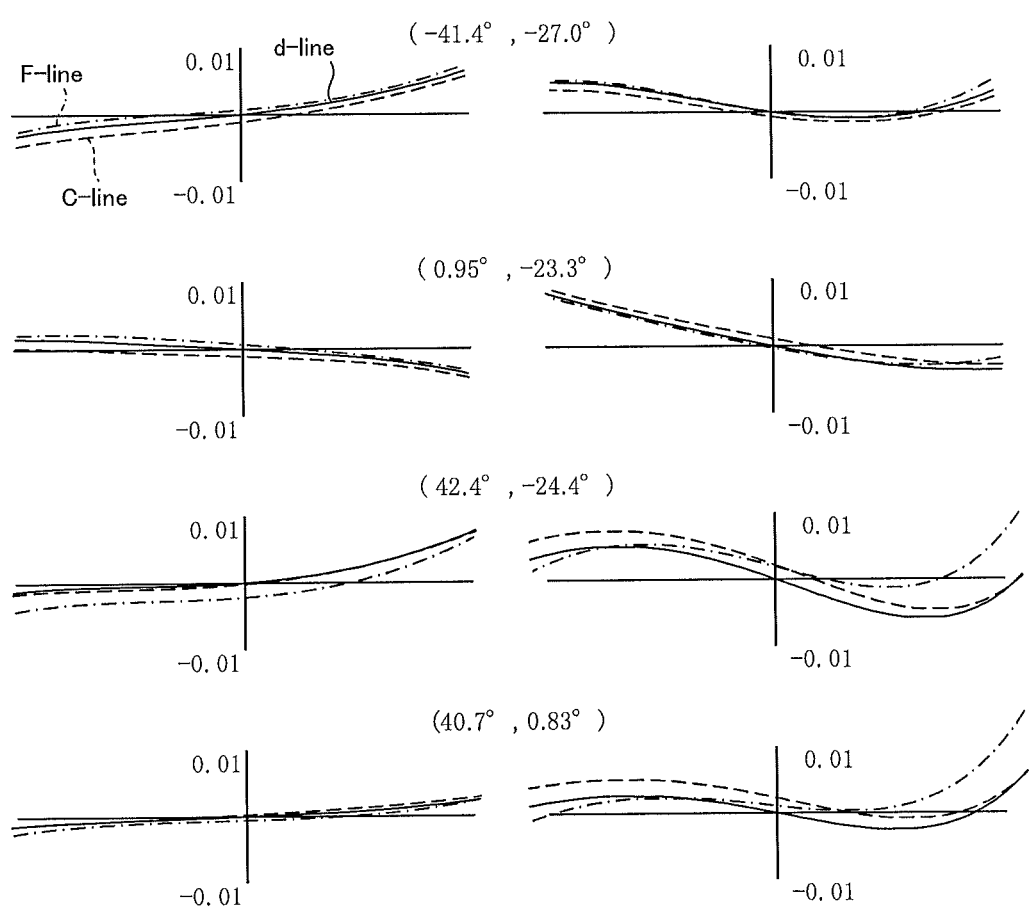
FIG. 18 is a transverse aberration diagram for the stereoscopic imaging optical system according to Example 2.

FIG. 16 is a sectional view of the stereoscopic imaging optical system 1 according to Example 2 as taken along its center axis C, and FIGS. 17 and 18 are transverse aberrational diagrams for the stereoscopic imaging optical system 1 according to Example 2.

As depicted in FIG. 16, the stereoscopic imaging optical system 1 according to Example 2 includes, in order from its object side to its image side, a front group Gf including a first front group Gf1 with its center axis Cf1 as an optical axis and a second front group Gf2 with its center axis Cf2 arranged parallel with the center axis Cf1 of the first front group as an optical axis, a front deflection group Gfd including a first front deflection group Gfd1 which the center axis Cf1 of the first front group intersects and a second front deflection group Gfd2 which the center axis Cf2 of the second front group intersects, and a rear group Gb including a single center axis Cb.

Parallel arrangement of the first and second front groups Gf1 and Gf2 makes stereoscopic viewing possible.

Preferably, the first front group Gf1 includes a negative meniscus lens Lf1$_1$ convex on the object side, a cemented lens SUf1$_1$ consisting of a double-convex positive lens Lf1$_2$ and a negative meniscus lens Lf1$_3$ convex on the image plane side, a cemented lens SUf1$_2$ consisting of a double-concave negative lens Lf1$_4$ and a double-convex positive lens Lf1$_5$, and a first stop S1.

The first front deflection group Gfd1 includes an optical element Lfd1$_1$ in a wedge prism form, and is located adjacent to the first stop S1.

Preferably, the second front group Gf2 includes a negative meniscus lens Lf2$_1$ convex on the object side, a cemented lens SUf2$_1$ consisting of a double-convex positive lens Lf2$_2$ and a negative meniscus lens Lf2$_3$ convex on the image plane side, a cemented lens SUf2$_2$ consisting of a double-concave negative lens Lf2$_4$ and a double-convex positive lens Lf2$_5$, and a second stop S2.

The second front deflection group Gfd2 includes an optical element Lfd2$_1$ in a wedge prism form, and is located adjacent to the second stop S2.

The rear group Gb includes a double-convex positive lens Lb$_1$, a cemented lens SUb$_1$ consisting of a double-concave negative lens Lb$_2$ and a double-convex positive lens Lb$_3$, and a positive meniscus lens Lb$_4$ convex on the object side.

There is further a filter F located just in front of the image plane I.

A first light beam L1 incident from the first object plane on the first front group Gf1 passes through the negative meniscus lens Lf1$_1$, cemented lens SUf1$_1$, cemented lens SUf1$_2$ and first stop S1, and then exits out of the first front group Gf1, after which it enters the rear group Gb via the first front deflection group Gfd1.

A second light beam L2 incident from the second object plane on the second front group Gf2 passes through the negative meniscus lens Lf2$_1$, cemented lens SUf2$_1$, cemented lens SUf2$_2$ and second stop S2, and then exits out of the second front group Gf2, after which it enters the rear group Gb via the second front deflection group Gfd2.

The first and second light beams L1 and L2 incident on the rear group Gb each pass through the double-convex positive lens Lb$_1$, cemented lens SUb$_1$, positive meniscus lens Lb$_4$ and filter F, after which they enter the image plane I.

Upon projection of the first and second light beams L1 and L2 onto a section that is orthogonal to a plane including the center axes Cf1 and Cf2 of the first and second front groups and includes the center axis Cb of the rear group, the front deflection group Gfd in the stereoscopic imaging optical system 1 according to Example 2 deflects them in symmetrical directions while spacing away from the center axis Cb of the rear group.

Figure 19:
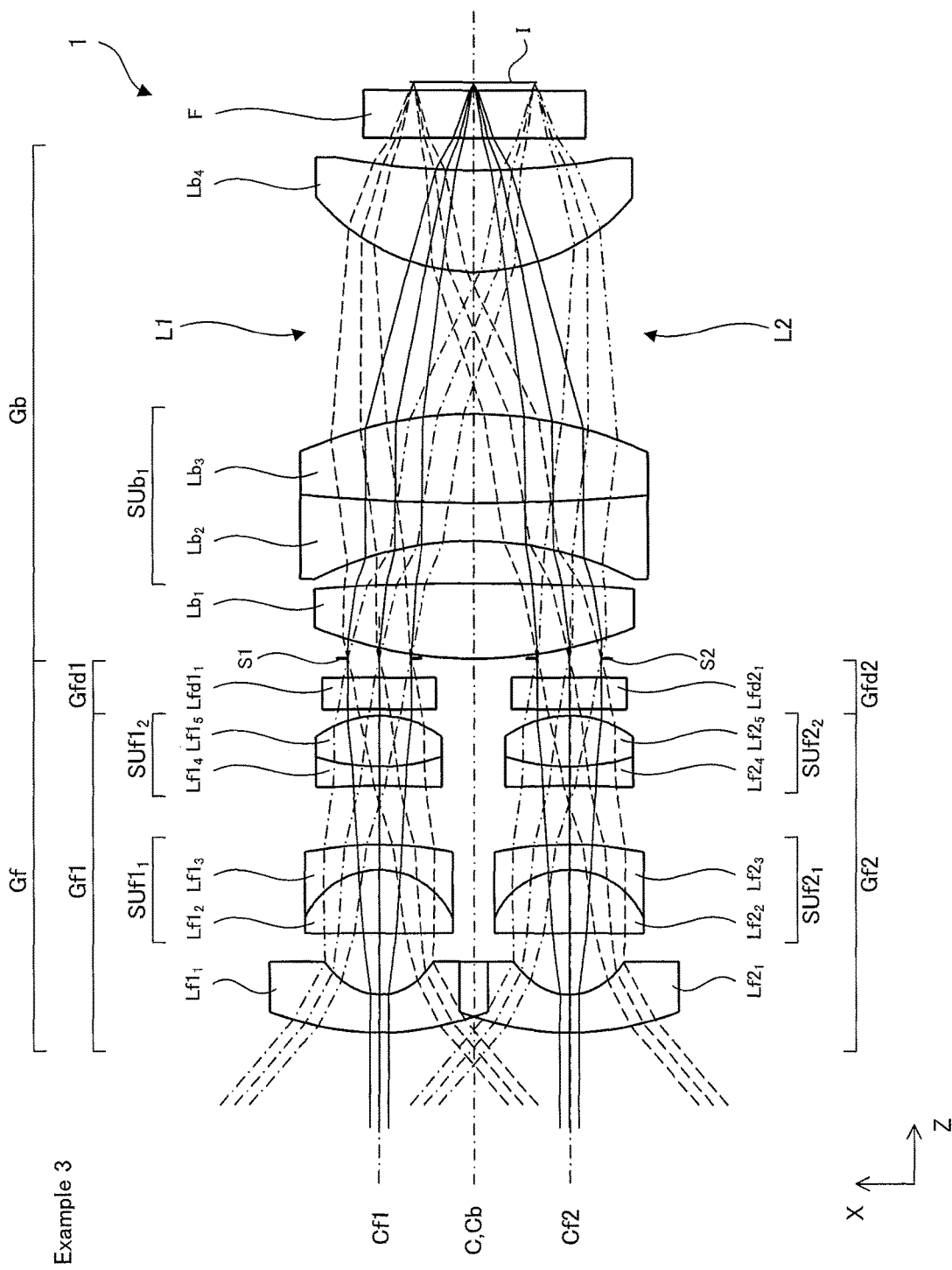
FIG. 19 is a sectional view of the stereoscopic imaging optical system according to Example 3 as taken along its center axis.
Figure 20:
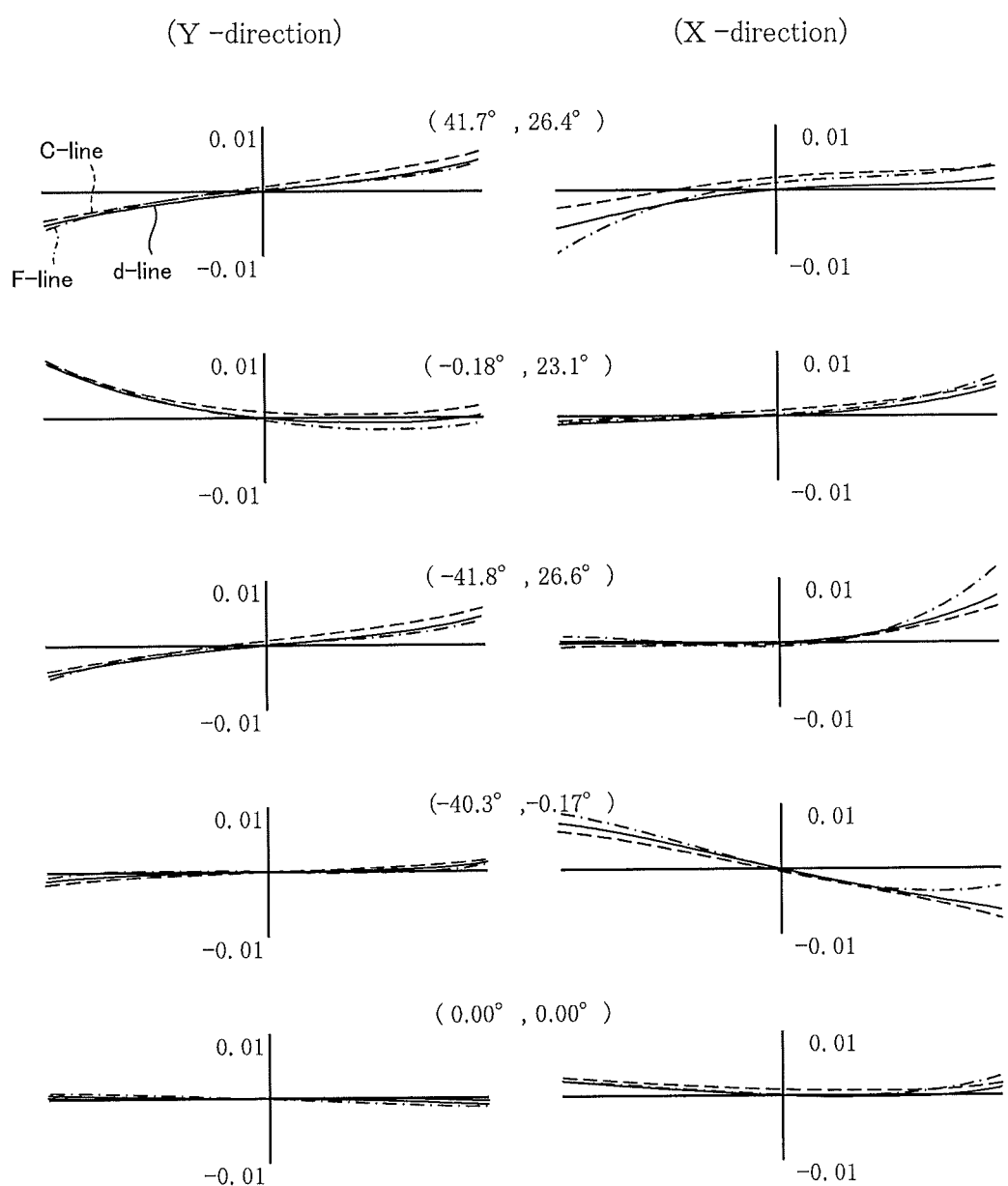
FIG. 20 is a transverse aberration diagram for the stereoscopic imaging optical system according to Example 3.
Figure 21:
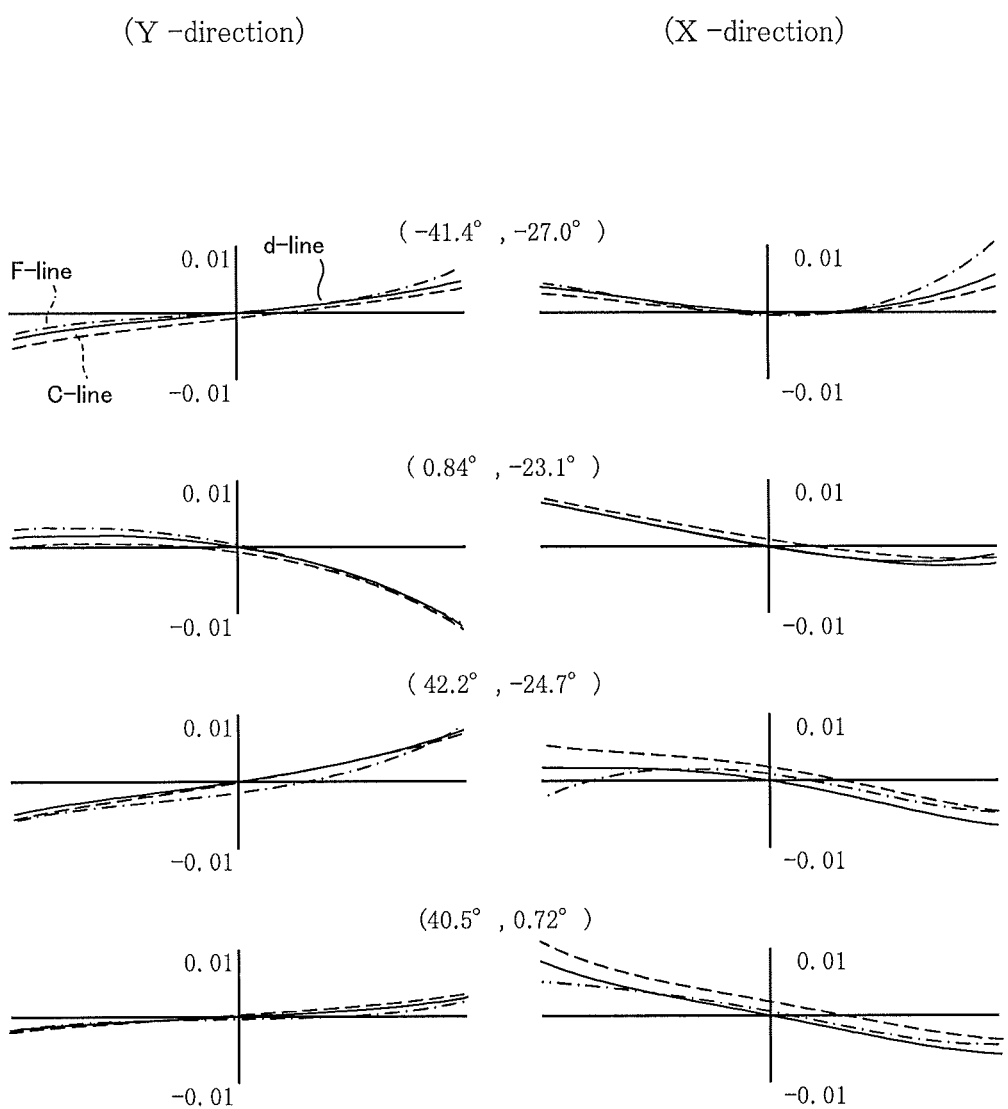
FIG. 21 is a transverse aberration diagram for the stereoscopic imaging optical system according to Example 3.

FIG. 19 is a sectional view of the stereoscopic imaging optical system 1 according to Example 3 as taken along its center axis C, and FIGS. 20 and 21 are transverse aberrational diagrams for the stereoscopic imaging optical system 1 according to Example 3.

As depicted in FIG. 19, the stereoscopic imaging optical system 1 according to Example 3 includes, in order from its object side to its image side, a front group Gf including a first front group Gf1 with its center axis Cf1 as an optical axis and a second front group Gf2 with its center axis Cf2 arranged parallel with the center axis Cf1 of the first front group as an optical axis, a front deflection group Gfd including a first front deflection group Gfd1 which the center axis Cf1 of the first front group intersects and a second front deflection group Gfd2 which the center axis Cf2 of the second front group intersects, and a rear group Gb including a single center axis Cb.

Parallel arrangement of the first and second front groups Gf1 and Gf2 makes stereoscopic viewing possible.

Preferably, the first front group Gf1 includes a negative meniscus lens Lf1$_1$ convex on the object side, a cemented lens SUf1$_1$ consisting of a positive meniscus lens Lf1$_2$ convex on the image plane side and a negative meniscus lens Lf1$_3$ convex on the image plane side, a cemented lens SUf1$_2$ consisting of a double-concave negative lens Lf1$_4$ and a double-convex positive lens Lf1$_5$, and a first stop S1.

The first front deflection group Gfd1 includes an optical element Lfd1$_1$ in a wedge prism form, and is located adjacent to the first stop S1.

Preferably, the second front group Gf2 includes a negative meniscus lens Lf2$_1$ convex on the object side, a cemented lens SUf2$_1$ consisting of a positive meniscus lens Lf2$_2$ convex on the image plane side and a negative meniscus lens Lf2$_3$ convex on the image plane side, a cemented lens SUf2$_2$ consisting of a double-concave negative lens Lf2$_4$ and a double-convex positive lens Lf2$_5$, and a second stop S2.

The second front deflection group Gfd2 includes an optical element Lfd2$_1$ in a wedge prism form, and is located adjacent to the second stop S2.

The rear group Gb includes a double-convex positive lens Lb$_1$, a cemented lens SUb$_1$ consisting of a double-concave negative lens $Lb_2$ and a double-convex positive lens $Lb_3$, and a positive meniscus lens $Lb_4$ convex on the object side.

There is further a filter F located just in front of the image plane I.

A first light beam L1 incident from the first object plane on the first front group Gf1 passes through the negative meniscus lens $Lf1_1$, cemented lens $SUf1_1$, cemented lens $SUf1_2$ and first stop S1, and then exits out of the first front group Gf1, after which it enters the rear group Gb via the first front deflection group Gfd1.

A second light beam L2 incident from the second object plane on the second front group Gf2 passes through the negative meniscus lens $Lf2_1$, cemented lens $SUf2_1$, cemented lens $SUf2_2$ and second stop S2, and then exits out of the second front group Gf2, after which it enters the rear group Gb via the second front deflection group Gfd2.

The first and second light beams L1 and L2 incident on the rear group Gb each pass through the double-convex positive lens $Lb_1$, cemented lens $SUb_1$, positive meniscus lens $Lb_4$ and filter F, after which they enter the image plane I.

Upon projection of the first and second light beams L1 and L2 onto a section that is orthogonal to a plane including the center axes Cf1 and Cf2 of the first and second front groups and includes the center axis Cb of the rear group, the front deflection group Gfd in the stereoscopic imaging optical system 1 according to Example 3 deflects them in symmetrical directions while spacing away from the center axis Cb of the rear group.

Figure 24:
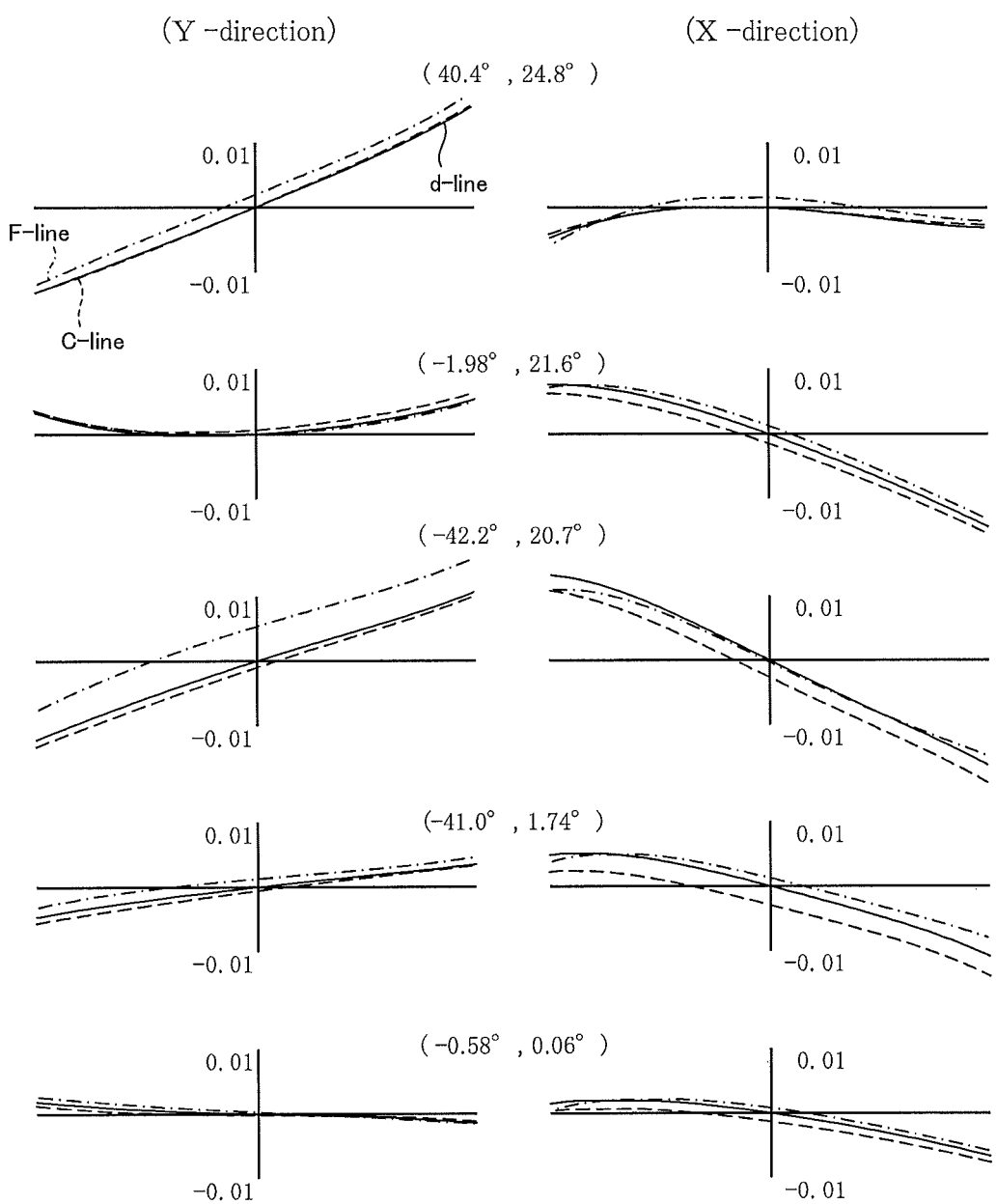
FIG. 24 is a transverse aberration diagram for the right optical path through the stereoscopic imaging optical system according to Example 4.
Figure 25:
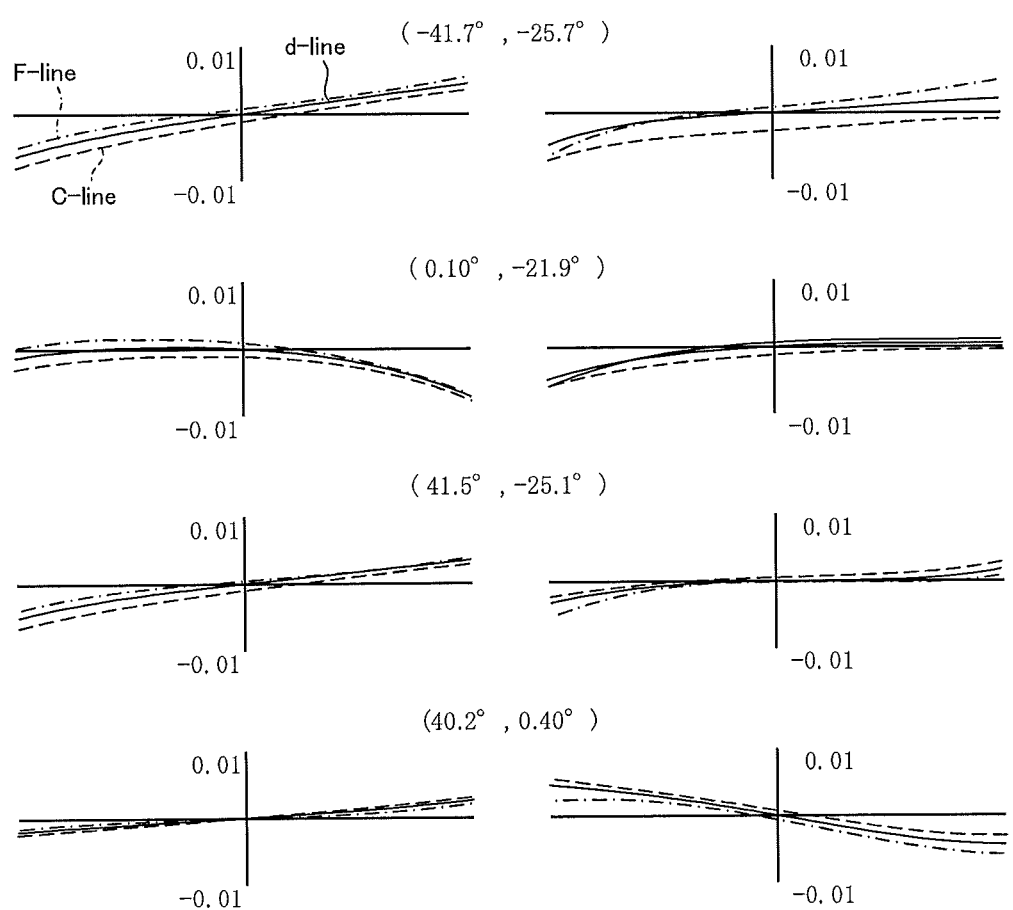
FIG. 25 is a transverse aberration diagram for the right optical path through the stereoscopic imaging optical system according to Example 4.
Figure 26:
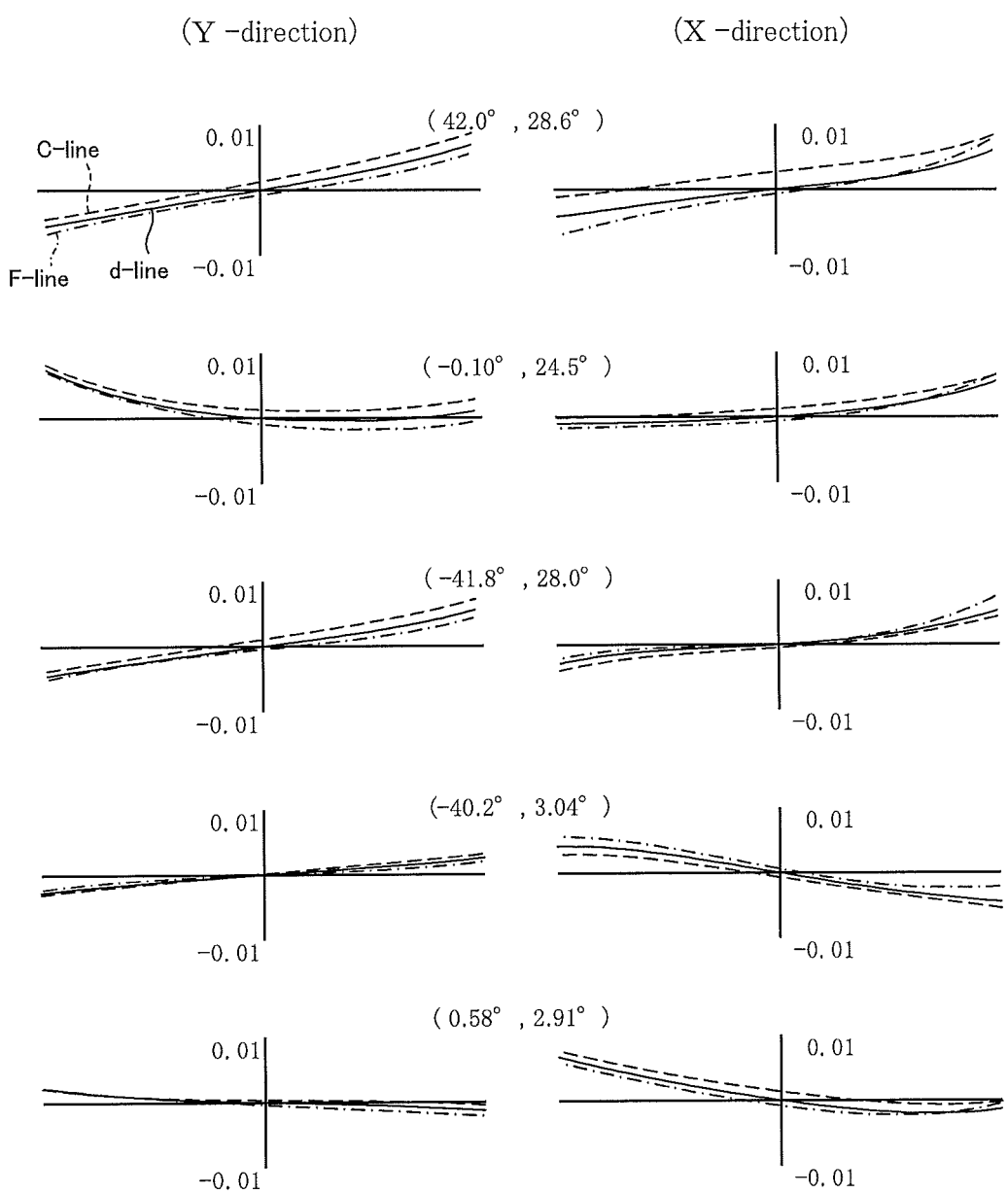
FIG. 26 is a transverse aberration diagram for the left optical path through the stereoscopic imaging optical system according to Example 4.

FIG. 22 is a sectional view of the stereoscopic imaging optical system 1 according to Example 4 as taken along its center axis C, and FIGS. 23A and 23B are sectional views of the stereoscopic imaging optical system according to one embodiment of the invention as viewed from a direction orthogonal to FIG. 22. FIGS. 24 and 25 are transverse aberrational diagrams for the right optical path through the stereoscopic imaging optical system 1 according to Example 4, and FIG. 26 is a transverse aberrational diagram for the left optical path through the stereoscopic imaging optical system 1 according to Example 4.

As depicted in FIGS. 22 and 23, the stereoscopic imaging optical system 1 according to Example 4 includes, in order from its object side to its image side, a front group Gf including a first front group Gf1 with its center axis Cf1 as an optical axis and a second front group Gf2 with its center axis Cf2 arranged parallel with the center axis Cf1 of the first front group as an optical axis, a front deflection group Gfd which the center axis Cf2 of the second front group intersects, and a rear group Gb having a single center axis Cb.

Parallel arrangement of the first and second front groups Gf1 and Gf2 makes stereoscopic viewing possible.

Preferably, the first front group Gf1 includes a negative meniscus lens $Lf1_1$ convex on the object side, a cemented lens $SUf1_1$ consisting of a double-convex positive lens $Lf1_2$ and a negative meniscus lens $Lf1_3$ convex on the image plane side, a cemented lens $SUf1_2$ consisting of a double-concave negative lens $Lf1_4$ and a double-convex positive lens $Lf1_5$, and a first stop S1.

The second front group Gf2 includes a negative meniscus lens $Lf2_1$ convex on the object side, a cemented lens $SUf2_1$ consisting of a double-convex positive lens $Lf2_2$ and a negative meniscus lens $Lf2_3$ convex on the image plane side, a cemented lens $SUf2_2$ consisting of a double-concave negative lens $Lf2_4$ and a double-convex positive lens $Lf2_5$, a flat plate $Lf2_6$, and a second stop S2.

The front deflection group Gfd includes an optical element $Lfd1_1$ in a wedge prism form, and is located adjacent to the first stop S1.

The rear group Gb includes a double-convex positive lens $Lb_1$, a cemented lens $SUb_1$ consisting of a double-concave negative lens $Lb_2$ and a double-convex positive lens $Lb_3$, and a positive meniscus lens $Lb_4$ convex on the object side.

There is further a filter F located just in front of the image plane I.

A first light beam L1 incident from the first object plane on the first front group Gf1 passes through the negative meniscus lens $Lf1_1$, cemented lens $SUf1_1$, cemented lens $SUf1_2$ and first stop S1, and then exits out of the first front group Gf1, after which it enters the rear group Gb via the front deflection group Gfd.

A second light beam L2 incident from the second object plane on the second front group Gf2 passes through the negative meniscus lens $Lf2_1$, cemented lens $SUf2_1$, cemented lens $SUf2_2$, second stop S2 and flat plate $Lf2_6$, and then exits out of the second front group Gf2, after which it enters the rear group Gb.

The first and second light beams L1 and L2 incident on the rear group Gb each pass through the double-convex positive lens $Lb_1$, cemented lens $SUb_1$, positive meniscus lens $Lb_4$ and filter F, after which they enter the image plane I.

Upon projection of the first and second light beams L1 and L2 onto a section that is orthogonal to a plane including the center axes Cf1 and Cf2 of the first and second front groups and includes the center axis Cb of the rear group, the front deflection group Gfd in the stereoscopic imaging optical system 1 according to Example 4 deflects the first light beam L1 passing through the front deflection group Gfd in such a way as to space away from the center axis Cb of the rear group, but does not deflect the second light beam L2 because of not passing through the front deflection group Gfd. Consequently, the first and second light beams L1 and L2 travel in mutually different directions.

Figure 27:
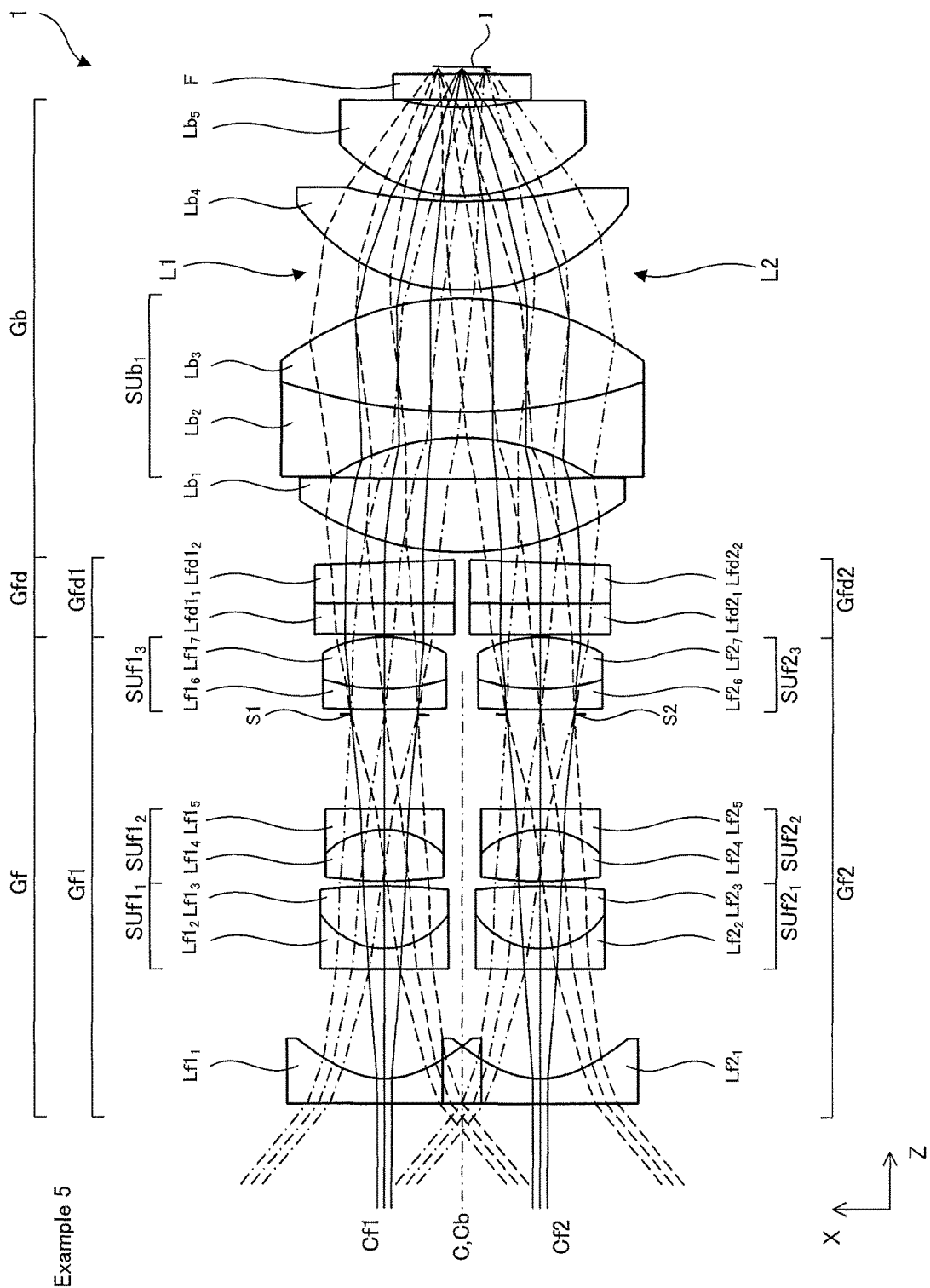
FIG. 27 is a sectional view of the stereoscopic imaging optical system according to Example 5 as taken along its center axis.
Figure 28A:
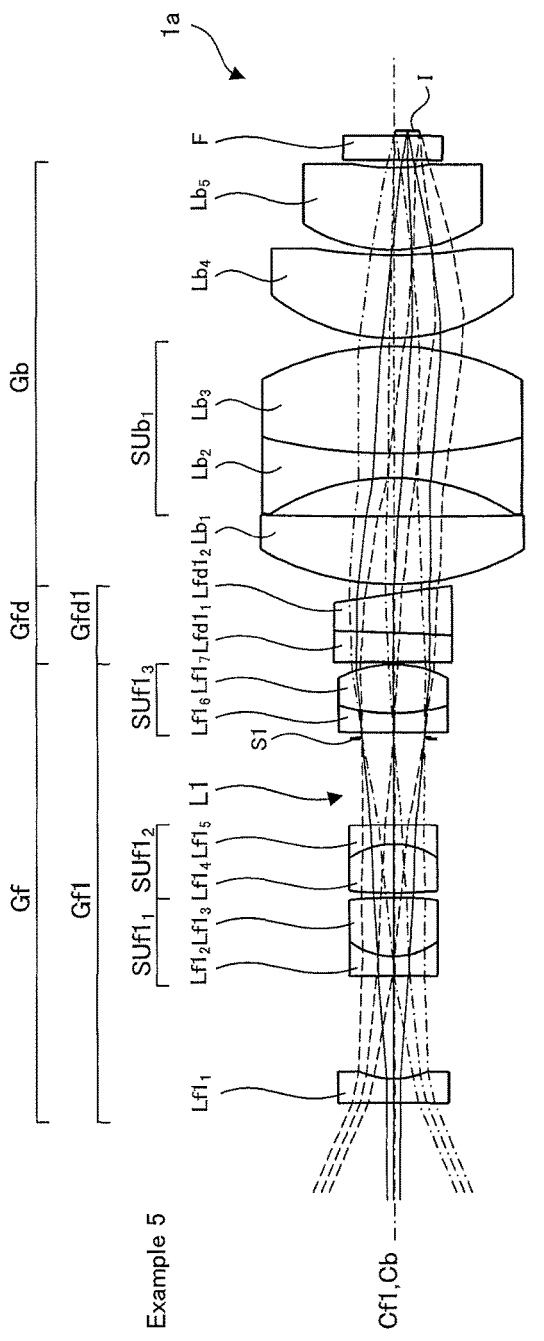
FIGS. 28A and 28B are sectional views of the stereoscopic imaging optical system according to one embodiment of the invention as viewed from a direction orthogonal to FIG. 27.
Figure 28B:
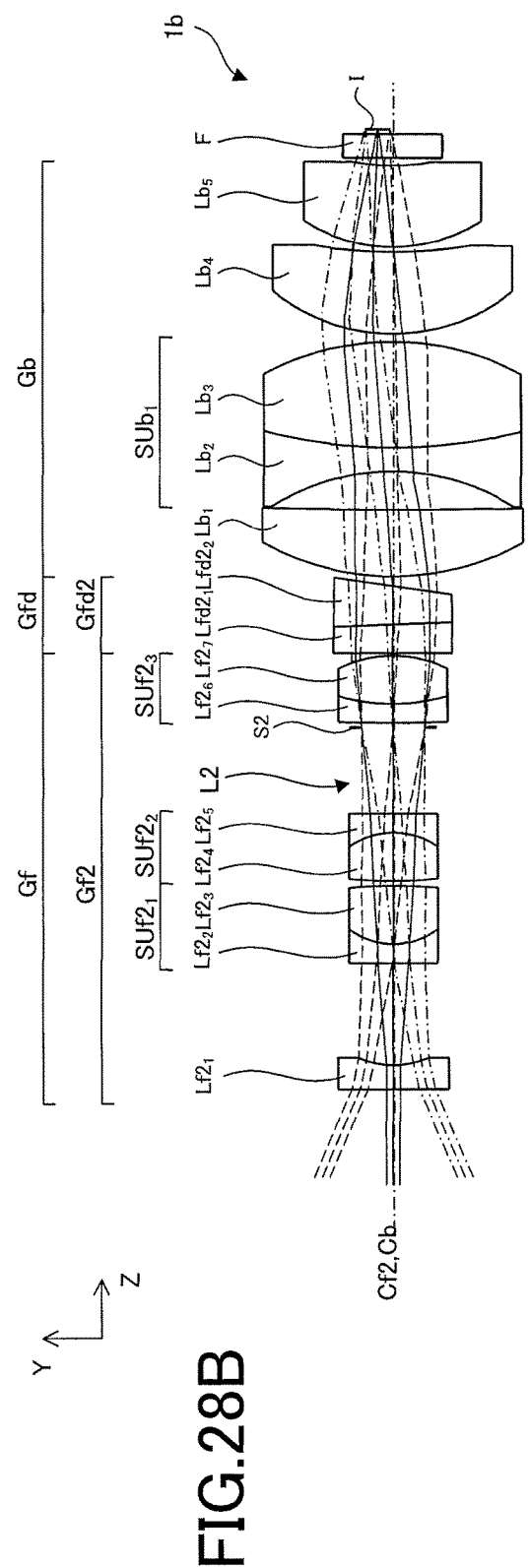

FIG. 27 is a sectional view of the stereoscopic imaging optical system 1 according to Example 5 as taken along its center axis C, and FIGS. 28A and 28B are sectional views of the stereoscopic imaging optical system according to one embodiment of the invention as viewed from a direction orthogonal to FIGS. 28A and 28B.

As depicted in FIGS. 27 and 28, the stereoscopic imaging optical system 1 according to Example 5 includes, in order from its object side to its image side, a front group Gf including a first front group Gf1 with its center axis Cf1 as an optical axis and a second front group Gf2 with its center axis Cf2 arranged parallel with the center axis Cf1 of the first front group as an optical axis, a front deflection group Gfd including a first front deflection group Gfd1 which the center axis Cf1 of the first front group intersects and a second front group Gfd2 which the center axis Cf2 of the second front group intersects, and a rear group Gb including a single center axis Cb.

Parallel arrangement of the first and second front groups Gf1 and Gf2 makes stereoscopic viewing possible.

Preferably, the first front group Gf1 includes a plano-concave lens $Lf1_1$ planar on the object side, a cemented lens $SUf1_1$ consisting of a plano-concave lens $Lf1_2$ planar on the object side and a double-convex positive lens $Lf1_3$, a cemented lens $SUf1_2$ consisting of a double-convex positive lens $Lf1_4$ and a plano-concave lens $Lf1_5$ planar on the image side, a first stop S1, and a cemented lens $SUf1_3$ consisting of a plano-concave lens $Lf1_6$ planar on the object side and a double-convex positive lens $Lf1_7$.

The first front deflection group Gfd1 includes optical elements $Lfd1_1$ and $Lfd1_2$, each in a wedge prism form. The optical elements $Lfd1_1$ and $Lfd1_2$ each in a wedge prism form, have different Abbe constants and are capable of achromatization. With the optical elements $Lfd1_1$ and $Lfd1_2$ each in a wedge prism form, it is possible to reduce burdens of the rear group Gb on aberrational correction because they are capable of deflection even in a plane including the two center axes Cf1 and Cf2 of the front group Gf.

Preferably, the second front group Gf2 includes a plano-concave lens $Lf2_1$ planar on the object side, a cemented lens $SUf2_1$ consisting of a plano-concave lens $Lf2_2$ planar on the object side and a double-convex lens $Lf2_3$, a cemented lens $SUf2_2$ consisting of a double-convex positive lens $Lf2_4$ and a plano-concave lens $Lf2_5$ planar on the image plane side, a second stop S2, and a cemented lens $SUf2_3$ consisting of a plano-concave lens $Lf2_6$ planar on the object side and a double-convex positive lens $Lf2_7$.

The second front deflection group Gfd2 includes optical elements $Lfd2_1$ and $Lfd2_2$, each in a wedge prism form. The optical elements $Lfd2_1$ and $Lfd2_2$, each in a wedge prism form, have different Abbe constants and are capable of achromatization. With the optical elements $Lfd2_1$ and $Lfd2_2$ each in a wedge prism form, it is possible to reduce burdens of the rear group Gb on aberrational correction because they are capable of deflection even in a plane including the two center axes Cf1 and Cf2 of the front group Gf.

The rear group Gb includes a positive meniscus lens Lb, convex on the object side, a cemented lens $SUb_1$ consisting of a double-concave negative lens $Lb_2$ and a double-convex positive lens $Lb_3$, a positive meniscus lens $Lb_4$ convex on the object side, and a positive meniscus lens $Lb_5$ convex on the object side.

There is further a filter F located just in front of the image plane I.

A first light beam L1 incident from the first object plane on the first front group Gf1 passes through the plano-concave lens $Lf1_1$, cemented lens $SUf1_1$, cemented lens $SUf1_2$, first stop S1 and cemented lens $SUf1_3$, and then exits out of the first front group Gf1, after which it enters the rear group Gb via the first front deflection group Gfd1.

A second light beam L2 incident from the second object plane on the second front group Gf2 passes through the plano-concave lens $Lf2_1$, cemented lens $SUf2_1$, cemented lens $SUf2_2$, second stop S2 and cemented lens $SUf2_3$, and then exits out of the second front group Gf2, after which it enters the rear group Gb via the second front deflection group Gfd2.

The first and second light beams L1 and L2 incident on the rear group Gb each pass through the positive meniscus lens $Lb_1$, cemented lens $SUb_1$, positive meniscus lens $Lb_4$, positive meniscus lens $Lb_5$ and filter F, after which they enter the image plane I.

Upon projection of the first and second light beams L1 and L2 onto a section that is orthogonal to a plane including the center axes Cf1 and Cf2 of the first and second front groups and includes the center axis Cb of the rear group, the front deflection group Gfd in the stereoscopic imaging optical system 1 according to Example 5 deflects them in symmetrical directions while spacing away from the center axis Cb of the rear group.

Figure 29:
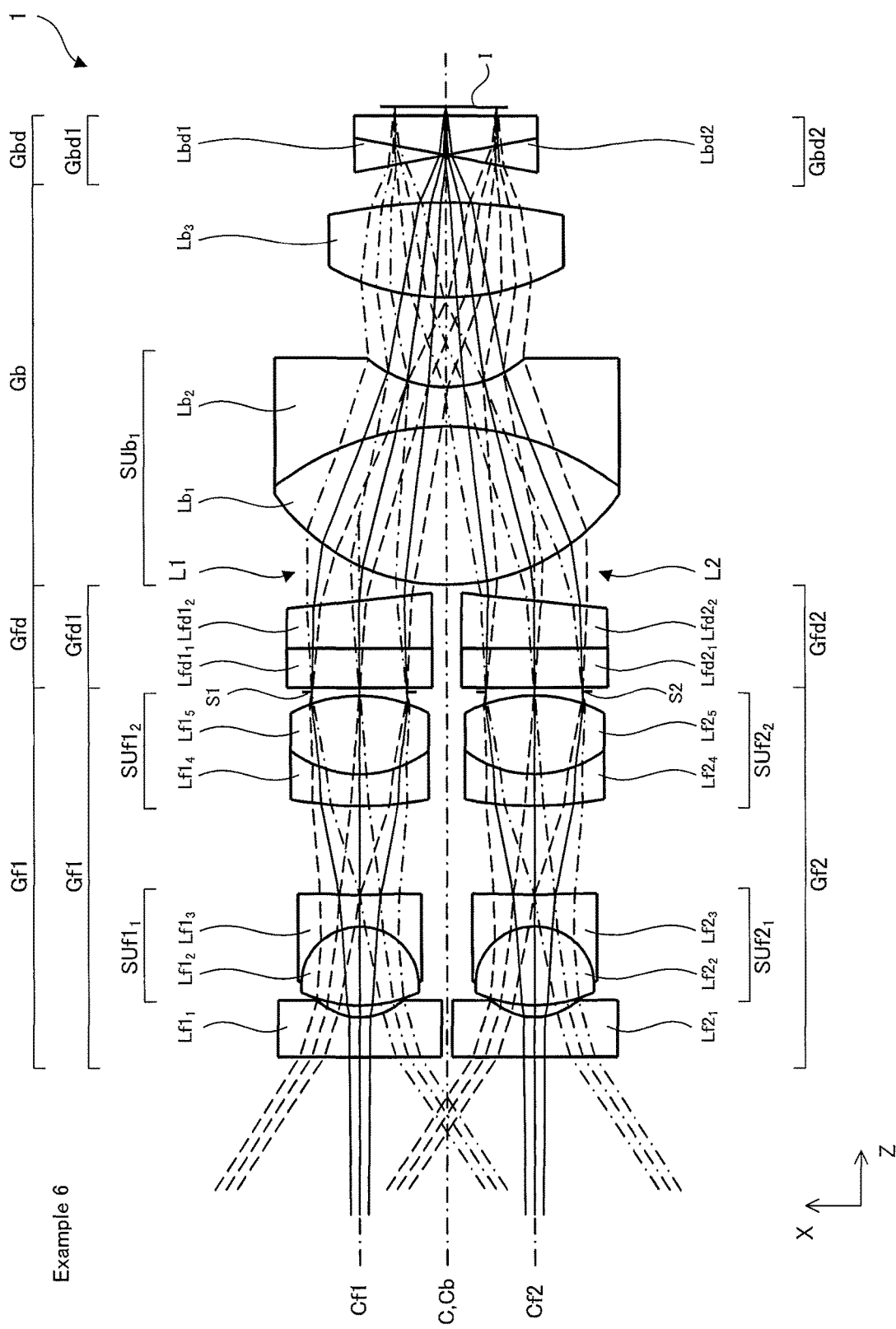
FIG. 29 is a sectional view of the stereoscopic imaging optical system according to Example 6 as taken along its center axis C.
Figure 30A:
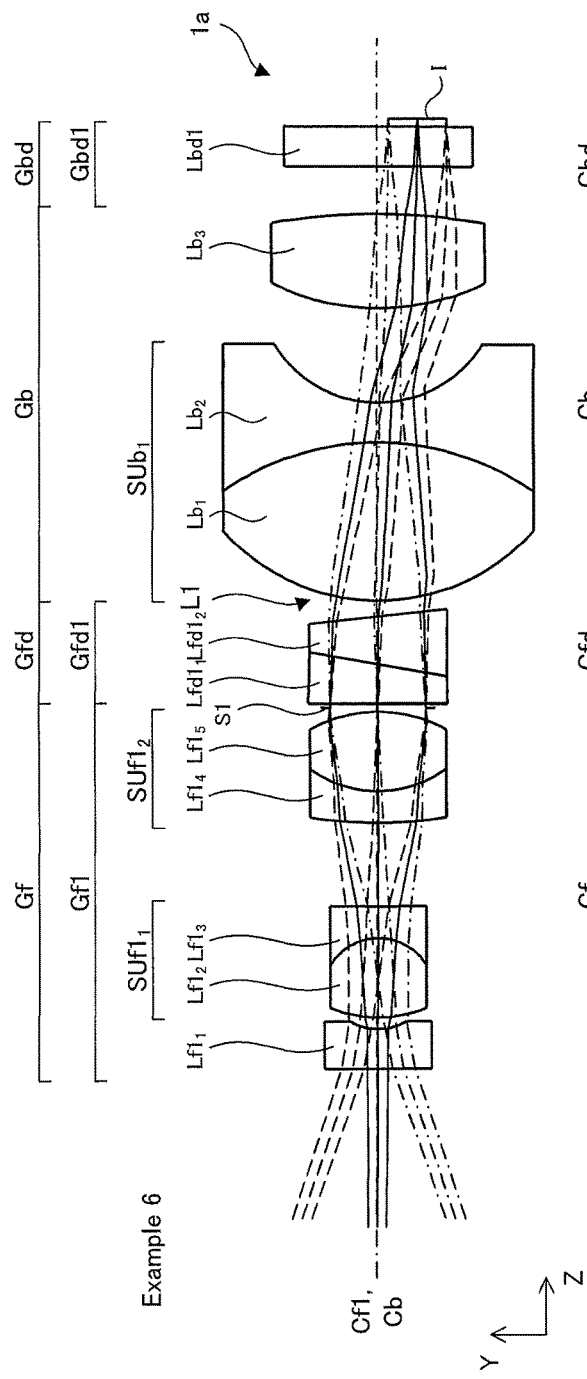
FIGS. 30A and 30B are sectional views of the stereoscopic imaging optical system according to one embodiment of the invention as viewed from a direction orthogonal to FIG. 27.
Figure 30B:
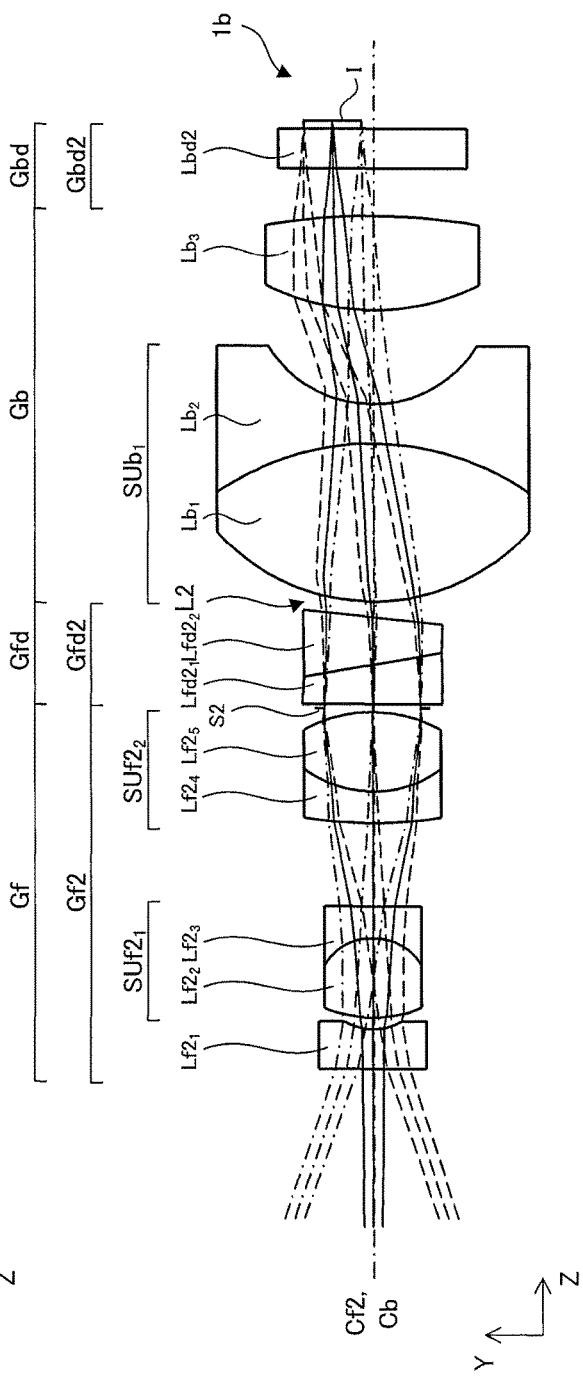
Figure 31:
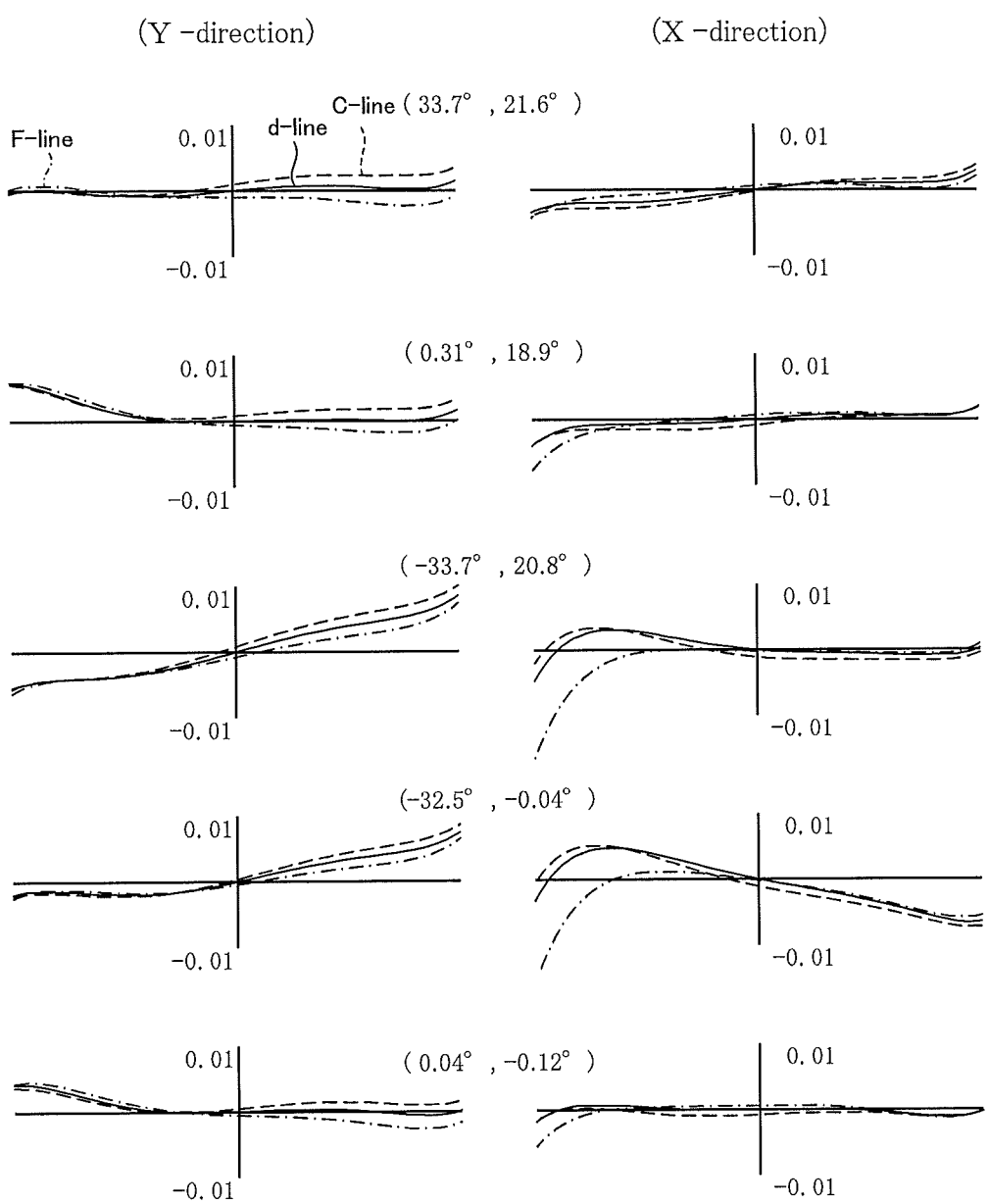
FIG. 31 is a transverse aberration diagram for the stereoscopic imaging optical system according to Example 6.
Figure 32:
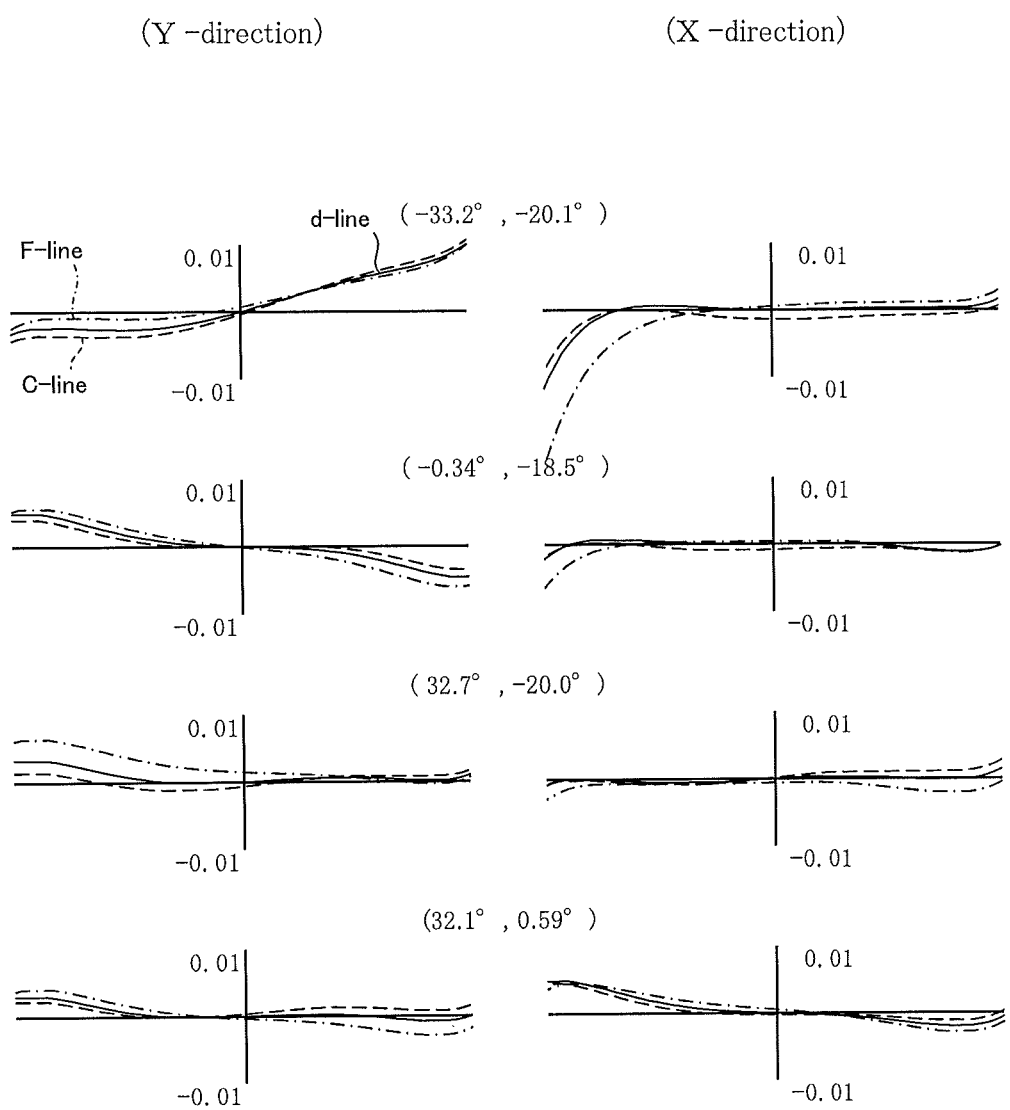
FIG. 32 is a transverse aberration diagram for the stereoscopic imaging optical system according to Example 6.

FIG. 29 is a sectional view of the stereoscopic imaging optical system 1 according to Example 6 as taken along its center axis C, and FIGS. 30A and 30B are a sectional view of a stereoscopic imaging optical system according to one embodiment of the invention as viewed from a direction orthogonal to FIG. 29. FIGS. 31 and 32 are transverse aberrational diagrams for the stereoscopic imaging optical system 1 according to Example 6.

As depicted in FIGS. 29 and 30, the stereoscopic imaging optical system 1 according to Example 6 includes, in order from its object side to its image side, a front group Gf including a first front group Gf1 with its center axis Cf1 as an optical axis and a second front group Gf2 with its center axis Cf2 arranged parallel with the center axis Cf1 of the first front group as an optical axis, a front deflection group Gfd including a first front deflection group Gfd1 which the center axis Cf1 of the first front group intersects and a second front deflection group Gfd2 which the center axis Cf2 of the second front group intersects, a rear group Gb having a single center axis, and a rear deflection group Gbd that is located between the rear group Gb and the image plane and includes the first and second deflection groups Gbd1 and Gbd2 that are located in different positions and in different directions orthogonal to the center axis Cb of the rear group in a section that is orthogonal to a plane including the center axes Cf1 and Cf2 of the first and second front groups and includes the center axis Cb of the rear group.

Parallel arrangement of the first and second front groups Gf1 and Gf2 makes stereoscopic viewing possible.

Preferably, the first front group Gf1 includes a plano-concave lens $Lf1_1$ planar on the object side, a cemented lens $SUf1_1$ consisting of a double-convex positive lens $Lf1_2$ and a double-concave negative lens $Lf1_3$, a cemented lens $SUf1_2$ consisting of a negative meniscus lens $Lf1_4$ convex on the object side and a double-convex positive lens $Lf1_5$, and a first stop S1.

The first front deflection group Gfd1 includes optical elements $Lfd1_1$ and $Lfd1_2$ each in a wedge prism form. The optical elements $Lfd1_1$ and $Lfd1_2$, each in a wedge prism form, have different Abbe constants and are capable of achromatization.

Preferably, the second front group Gf2 includes a plano-concave lens $Lf2_1$ planar on the object side, a cemented lens $SUf2_1$ consisting of a double-convex positive lens $Lf2_2$ and a double-concave negative lens $Lf2_3$, a cemented lens $SUf2_2$ consisting of a negative meniscus lens $Lf2_4$ convex on the object side and a double-convex positive lens $Lf2_5$, and a second stop S2.

The second front deflection group Gfd2 includes optical elements $Lfd2_1$ and $Lfd2_2$ each in a wedge prism form. The optical elements $Lfd2_1$ and $Lfd2_2$, each in a wedge prism form, have different Abbe constants and are capable of achromatization.

The rear group Gb includes a cemented lens $SUb_1$ consisting of a double-convex positive lens $Lb_1$ and a double-concave negative lens $Lb_2$, and a double-convex positive lens $Lb_3$.

The first rear deflection group Gbd1 includes an optical element Lbd1 in a wedge prism form.

The second rear deflection group Gbd2 includes an optical element Lbd2 in a wedge prism form.

The optical elements Lbd1 and Lbd2, each in a wedge prism form, may be formed as an integral element rather than separate elements.

A first light beam L1 incident from the first object plane (not shown) on the first front group Gf1 passes through the plano-concave lens $Lf1_1$, cemented lens $SUf1_1$, cemented lens $SUf1_2$ and first stop S1, and then emits out of the first front group Gf1, after which it enters the rear group Gb via the first front deflection group Gfd1.

A second light beam L2 incident from the second object plane (not shown) on the second front group Gf2 passes through the plano-concave lens $Lf2_1$, cemented lens $SUf2_1$, cemented lens $SUf2_2$ and second stop S2, and then emits out of the second front group Gf2, after which it enters the rear group Gb via the second front deflection group Gfd2.

The first and second light beams L1 and L2 incident on the rear group Gb each pass through the cemented lens $SUb_1$ and double-convex positive lens $Lb_3$, after which they enter the rear deflection group Gbd.

The first and second light beams L1 and L2 incident on the rear deflection group Gbd each pass through the wedge prism-form optical element Lbd1 in the first rear deflection group Gbd1 and the wedge prism-form optical element Lbd2 in the second rear deflection group Gbd2, after which they enter the image plane I.

Upon projection of the first and second light beams L1 and L2 onto a section that is orthogonal to a plane including the center axes Cf1 and Cf2 of the first and second front groups and includes the center axis Cb of the rear group, the front deflection group Gfd in the stereoscopic imaging optical system 1 according to Example 6 deflects them in symmetrical directions while spacing away from the center axis Cb of the rear group.

The rear deflection group Gbd in the stereoscopic imaging optical system 1 according to Example 6 deflects the first and second light beams L1 and L2 after passing through the rear group Gb symmetrically with respect to the center axis Cb of the rear group such that the angles of incidence of the first and second light beams L1 and L2 on the image plane I come close to the perpendicular.

Figure 33:
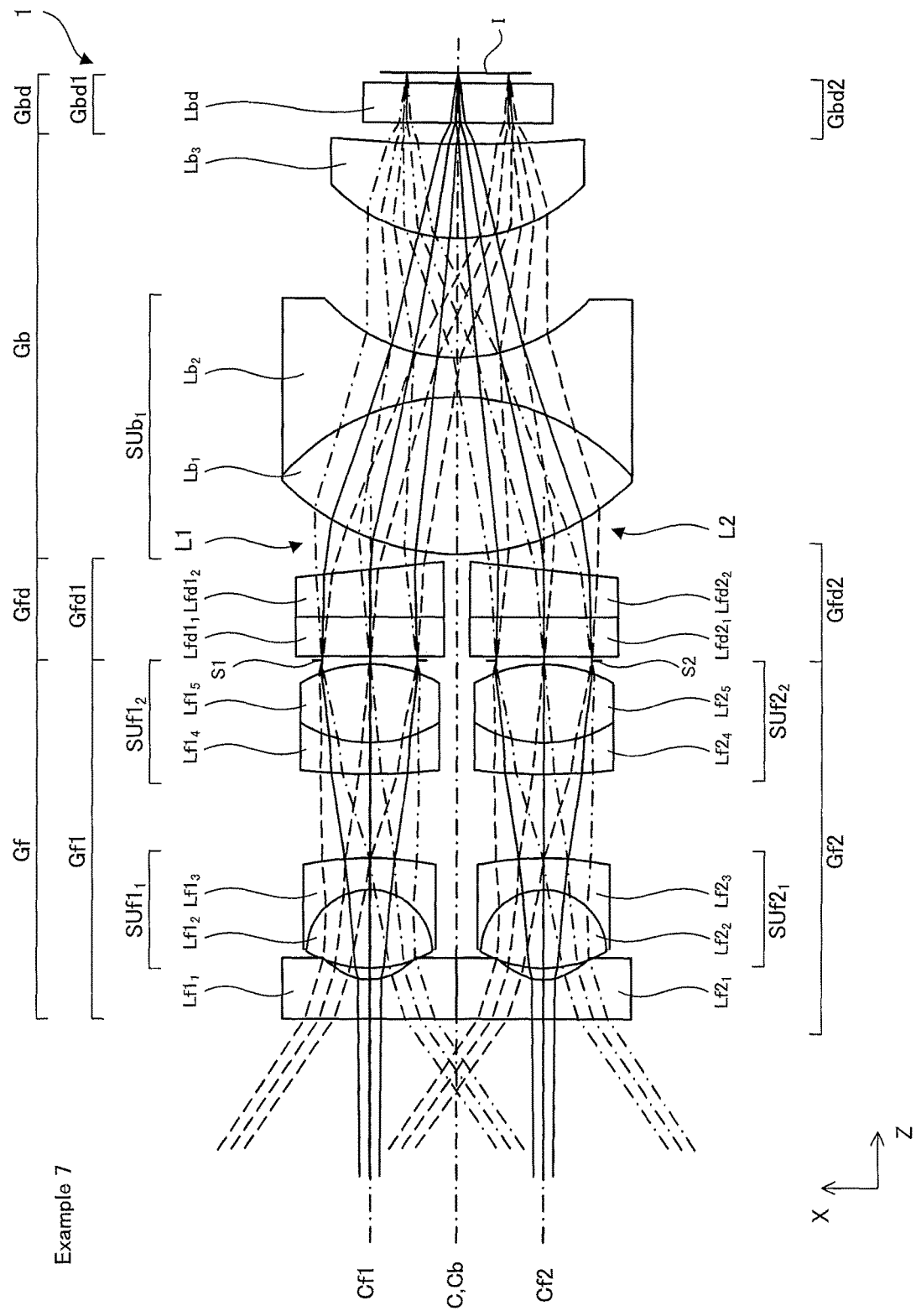
FIG. 33 is a sectional view of the stereoscopic imaging optical system according to Example 7 as taken along its center axis C.
Figure 35:
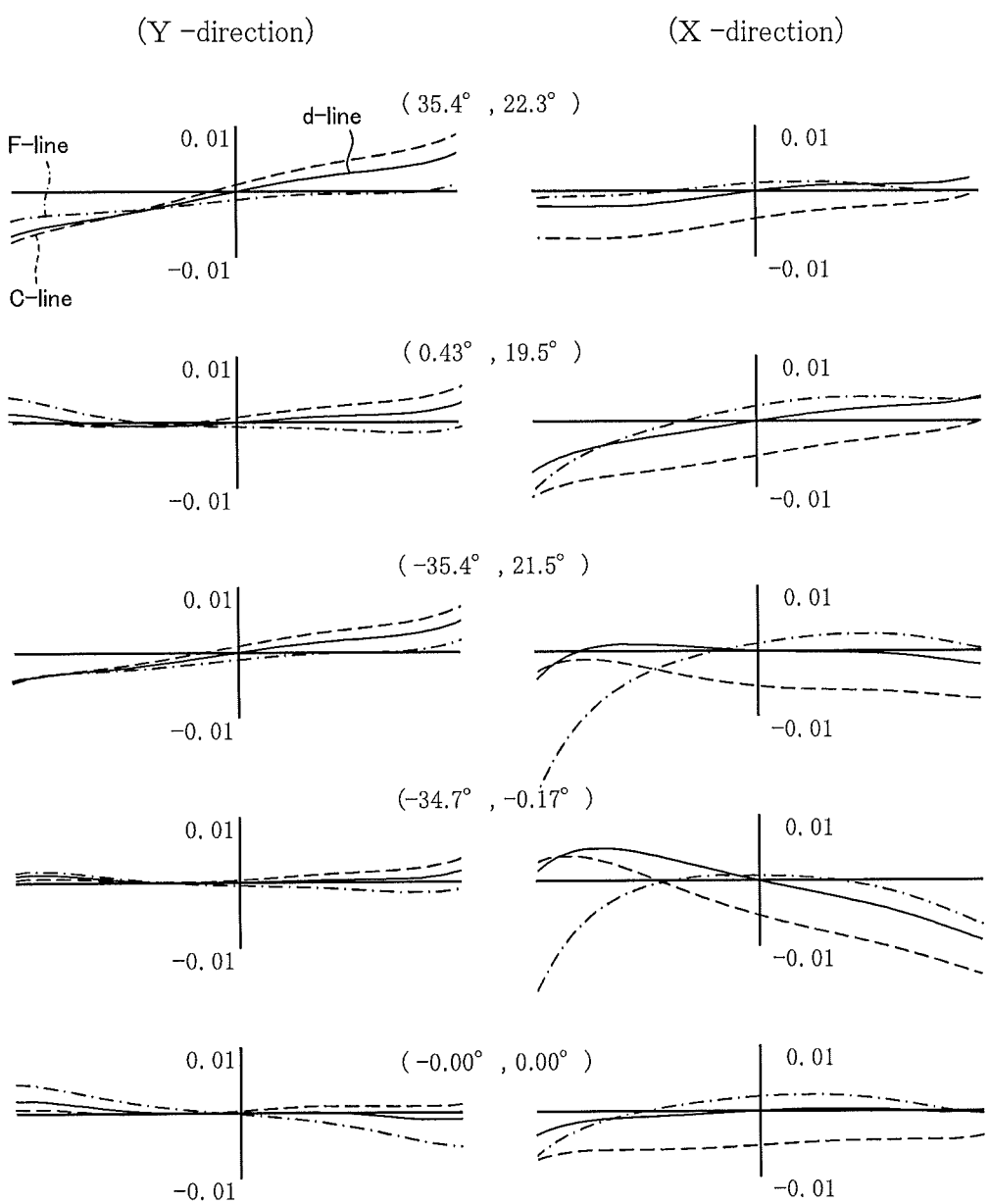
FIG. 35 is a transverse aberration diagram for the stereoscopic imaging optical system according to Example 7.
Figure 36:
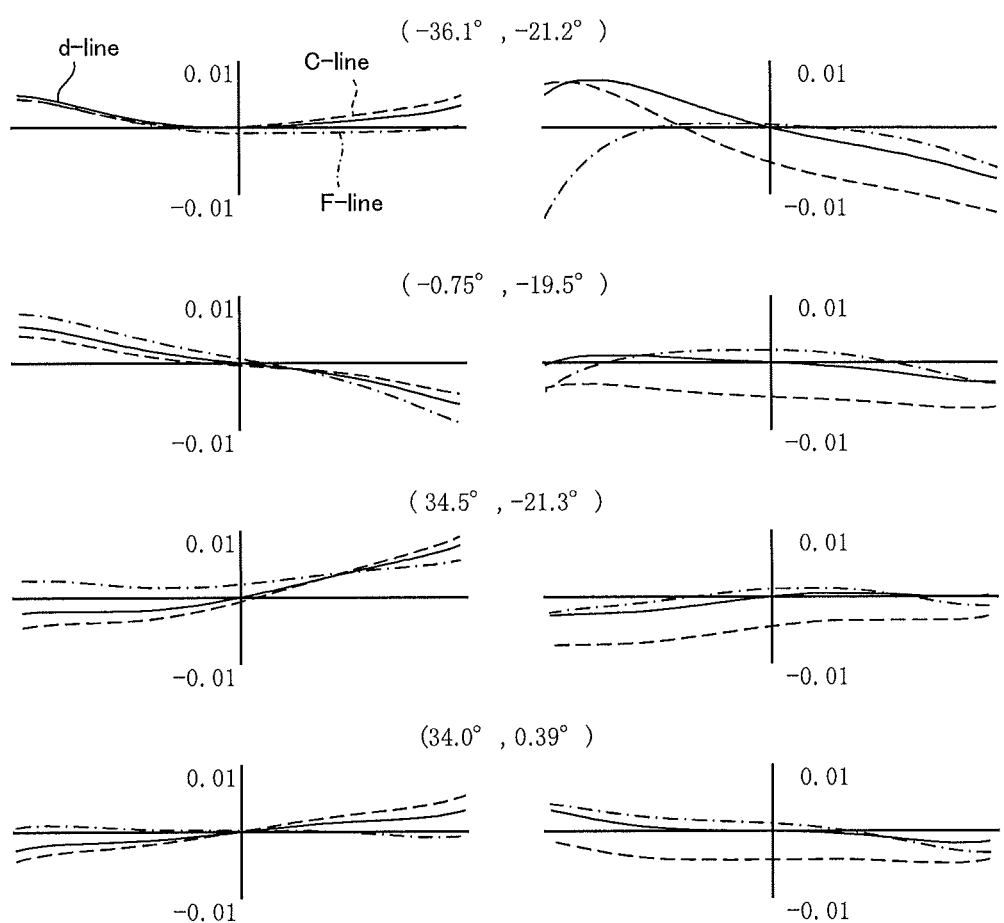
FIG. 36 is a transverse aberration diagram for the stereoscopic imaging optical system according to Example 7.

FIG. 33 is a sectional view of the stereoscopic imaging optical system 1 according to Example 7 as taken along its center axis C, and FIGS. 34A and 34B are sectional views of a stereoscopic imaging optical system according to one embodiment of the invention as viewed from a direction orthogonal to FIG. 33. FIGS. 35 and 36 are transverse aberrational diagrams for the stereoscopic imaging optical system 1 according to Example 7.

Figure 34:
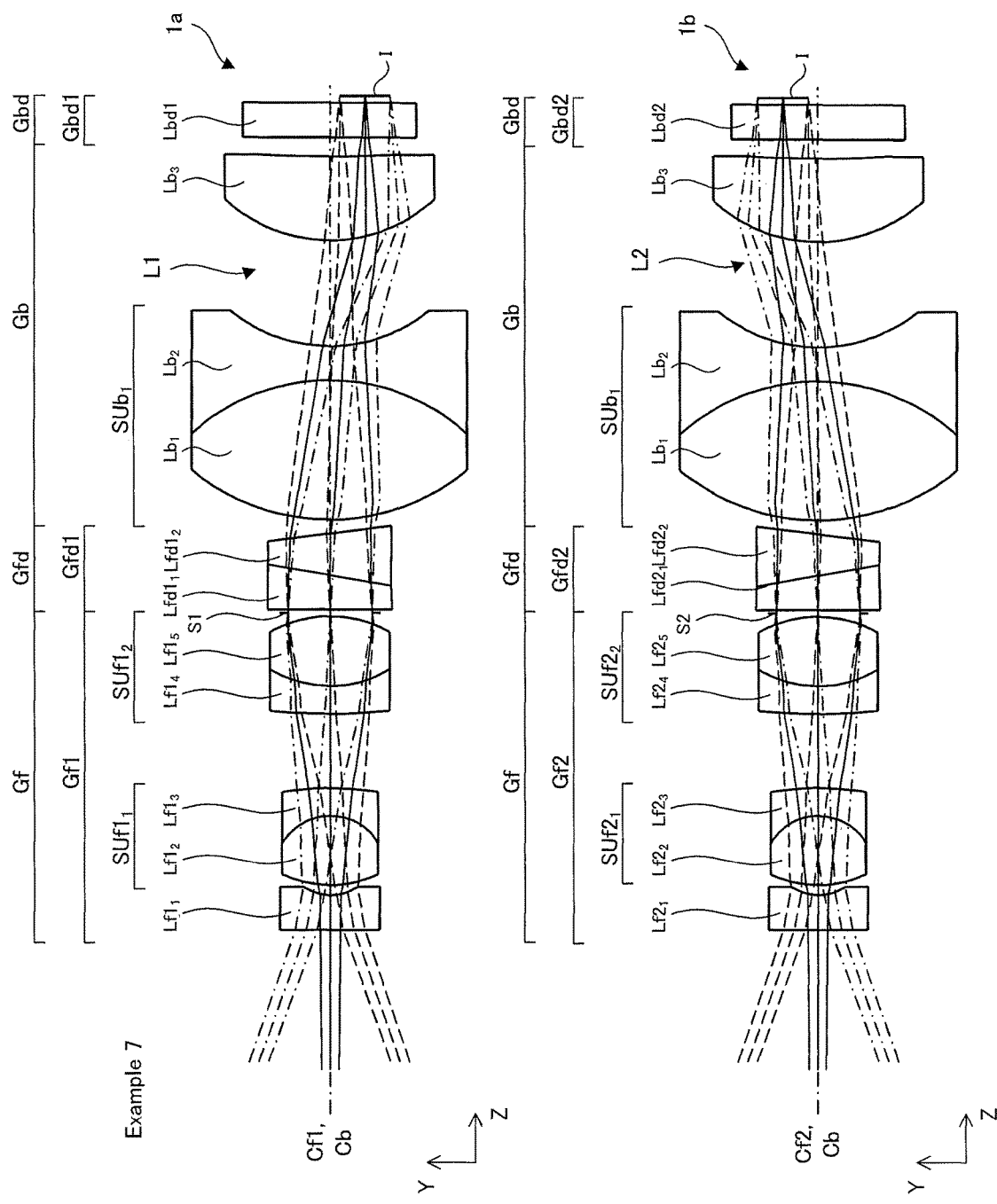
FIGS. 34A and 34B are sectional views of the stereoscopic imaging optical system according to one embodiment of the invention as viewed from a direction orthogonal to FIG. 33.

As depicted in FIGS. 33 and 34, the stereoscopic imaging optical system 1 according to Example 7 includes, in order from its object side to its image side, a front group Gf including a first front group Gf1 with its center axis Cf1 as an optical axis and a second front group Gf2 with its center axis Cf2 arranged parallel with the center axis Cf1 of the first front group as an optical axis, a front deflection group Gfd including a first front deflection group Gfd1 which the center axis Cf1 of the first front group intersects and a second front deflection group Gfd2 which the center axis Cf2 of the second front group intersects, a rear group Gb having a single center axis Cb, and a rear deflection group Gbd that is located between the rear group Gb and the image plane I and includes the first and second deflection groups Gbd1 and Gbd2 that are located in different positions and in different directions in a section that is orthogonal to a plane including the center axes Cf1 and Cf2 of the first and second front groups.

Parallel arrangement of the first and second front groups Gf1 and Gf2 makes stereoscopic viewing possible.

Preferably, the first front group Gf1 includes a plano-concave lens $Lf1_1$ planar on the object side, a cemented lens $SUf1_1$ consisting of a double-convex positive lens $Lf1_2$ and a negative meniscus lens $Lf1_3$ convex on the image plane side, a cemented lens $SUf1_2$ consisting of a negative meniscus lens $Lf1_4$ convex on the object side and a double-convex positive lens $Lf1_5$, and a first stop S1.

The first front deflection group Gfd1 includes optical elements $Lfd1_1$ and $Lfd1_2$ each in a wedge prism form. The optical elements $Lfd1_1$ and $Lfd1_2$, each in a wedge prism form, have different Abbe constants and are capable of achromatization.

Preferably, the second front group Gf2 includes a plano-concave lens $Lf2_1$ planar on the object side, a cemented lens $SUf2_1$ consisting of a double-convex positive lens $Lf2_2$ and a negative meniscus lens $Lf2_3$ convex on the image plane side, a cemented lens $SUf2_2$ consisting of a negative meniscus lens $Lf2_4$ convex on the object side and a double-convex positive lens $Lf2_5$, and a second stop S2.

The second front deflection group Gfd2 includes optical elements $Lfd2_1$ and $Lfd2_2$ each in a wedge prism form. The optical elements $Lfd2_1$ and $Lfd2_2$, each in a wedge prism form, have different Abbe constants and are capable of achromatization.

The rear group Gb includes a cemented lens $SUb_1$ consisting of a double-convex positive lens Lb, and a double-concave negative lens Lb, and a double-convex positive lens $Lb_3$.

The first rear deflection group Gbd1 includes a diffractive optical element Lbd1 formed of a flat plate that has a saw-toothed shape on the object plane side.

The second rear deflection group Gbd2 includes a diffractive optical element Lbd2 formed of a flat plate that has a saw-toothed shape on the object plane side.

The optical elements Lbd1 and Lbd2, each in a wedge prism form, may be formed as an integral element rather than separate element.

A first light beam L1 incident from the first object plane on the first front group Gf1 passes through the plano-concave lens $Lf1_1$, cemented lens $SUf1_1$, cemented lens $SUf1_2$ and first stop S1, and then emits out of the first front group Gf1, after which it enters the rear group Gb via the first front deflection group Gfd1.

A second light beam L2 incident from the second object plane on the second front group Gf2 passes through the plano-concave lens $Lf2_1$, cemented lens $SUf2_1$, cemented lens $SUf2_2$ and second stop S2, and then emits out of the second front group Gf2, after which it enters the rear group Gb via the second front deflection group Gfd2.

The first and second light beams L1 and L2 incident on the rear group Gb each pass through the cemented lens $SUb_1$ and double-convex positive lens $Lb_3$, after which they enter the rear deflection group Gbd.

The first and second light beams L1 and L2 incident on the rear deflection group Gbd each pass through the diffractive optical element Lbd1 in the first rear deflection group Gbd1 and the diffractive optical element Lbd2 in the second rear deflection group Gbd2, after which they enter the image plane I.

Upon projection of the first and second light beams L1 and L2 onto a section that is orthogonal to a plane including the center axes Cf1 and Cf2 of the first and second front groups and includes the center axis Cb of the rear group, the front deflection group Gfd in the stereoscopic imaging optical system 1 according to Example 7 deflects them in symmetrical directions while spacing away from the center axis Cb of the rear group.

The rear deflection group Gbd in the stereoscopic imaging optical system 1 according to Example 7 deflects the first and second light beams L1 and L2 after passing through the rear group Gb symmetrically with respect to the center axis Cb of the rear group such that the angles of incidence of the first and second light beams L1 and L2 on the image plane I come close to the perpendicular.

It is here to be noted that any desired spherical surface, aspheric surface, anamorphic surface, free-form surface or the like may be used for any surface in the front and rear deflection groups Gfd and Gbd. The application of such surfaces to the front and rear deflection groups Gfd and Gbd makes it possible to provide effective correction for aberrations.

Set out below are the constituting parameters in such Examples 1-4, 6 and 7 as described above, and the constituting parameters in Examples 1-4, 6 and 7 stand for the optical path taken by the first light beam.

In the case where, of the optical surfaces forming the optical system in each example, a specific surface and the subsequent surface form together a coaxial optical system, surface separations are given to them. In addition, radii of curvatures of surfaces, refractive indices of media and Abbe constants are given as usual.

Given to each decentered surface are the amount of decentration of the coordinate system—on which that surface is defined—from the origin O (X, Y and Z in the X-, Y- and Z-axis directions) and the angles ($\alpha$, $\beta$, $\gamma$ (°)) of tilt of the coordinate system for defining each surface with the X-, Y- and Z-axes of the coordinate system defined on the origin as center. Then, the positive $\alpha$ and $\beta$ mean counterclockwise rotation with respect to the positive directions of the respective axes, and the positive $\gamma$ means clockwise rotation with respect to the positive direction of the Z-axis. Referring here to the $\alpha$, $\beta$, $\gamma$ rotation of the center axis of a certain surface, the coordinate system for defining each surface is first $\alpha$ rotated counterclockwise about the X-axis of the coordinate system defined on the origin of an optical system. Then, the center axis of the rotated surface is $\beta$ rotated counterclockwise about the Y-axis of a new coordinate system. Finally, the center axis is $\gamma$ rotated clockwise about the Z-axis of a rotated new coordinate system.

Refractive indices and Abbe constants on d-line (wavelength: 587.56 nm) basis are given, and length is given in mm. The decentration of each surface is expressed by the amount of decentration from the reference surface as described above. The symbol "∞" affixed to the radius of curvature stands for infinity.

Aspheric data include data about aspheric lens surfaces. Aspheric surface shape or configuration may be represented by $$z = (y^2/r) / \left[ 1 + \{1 - (1+K) \cdot (y/r)^2\}^{1/2} \right] + A4y^4 + A6y^6 + A8y^8 + A10y^{10} \ldots$$

with the proviso that z is indicative of an optical axis where the direction of travel of light is positive and y is indicative of a direction orthogonal to the optical axis.

In the formula, r is a paraxial radius of curvature, K is the conic coefficient, and A4, A6 and A8 are the $4^{th}$, $6^{th}$ and $8^{th}$ order aspheric coefficients, respectively. Note here that the symbol "e" indicates that the subsequent numerical value is a power exponent having 10 as a base. For instance, "1.0e–5" means "$1.0 \times 10^{-5}$".

EXAMPLE 1

| Surface No. | Radius of curvature | Surface separation | Decentration | Refractive index | Abbe constant |
|---|---|---|---|---|---|
| Object plane | ∞ | 100.000 | | | |
| 1 | Aspheric surface [1] | 0.600 | | 1.8830 | 40.7 |
| 2 | Aspheric surface [2] | 1.066 | | | |
| 3 | 26.845 | 1.000 | | 1.9229 | 18.9 |
| 4 | −1.428 | 0.400 | | 1.8830 | 40.7 |
| 5 | −7.449 | 0.966 | | | |
| 6 | −12.279 | 0.300 | | 1.9229 | 18.9 |
| 7 | 3.471 | 0.800 | | 1.4875 | 70.2 |
| 8 | −1.709 | 0.075 | | | |
| 9 | Stop plane | 0.000 | | | |
| 10 | ∞ | 0.500 | | 1.4875 | 70.2 |
| 11 | ∞ | 0.300 | Decentration (1) | | |
| 12 | ∞ | 0.000 | Decentration (2) | | |
| 13 | 6.487 | 1.200 | | 1.8830 | 40.7 |
| 14 | −29.393 | 0.421 | | | |
| 15 | −5.655 | 0.600 | | 1.9229 | 18.9 |
| 16 | 75.749 | 1.400 | | 1.8830 | 40.7 |
| 17 | −6.615 | 2.232 | | | |
| 18 | 3.235 | 1.400 | | 1.8903 | 33.4 |
| 19 | 11.056 | 0.611 | | | |
| 20 | ∞ | 0.750 | | 1.5163 | 64.1 |
| 21 | ∞ | 0.100 | | | |
| Image plane | ∞ | | Decentration (3) | | |

| Aspheric surface [1] | | | | | |
|---|---|---|---|---|---|
| r | 4.208 | | | | |
| k | −3.1711e+000 | | | | |

| Aspheric surface [2] | | | | | |
|---|---|---|---|---|---|
| r | 0.877 | | | | |
| k | −5.5206e−001 | | | | |

| Decentration [1] | | | | | |
|---|---|---|---|---|---|
| X | 0.000 | Y | 0.000 | Z | 0.000 |
| α | 12.000 | β | 0.000 | γ | 0.000 |

-continued

| | Decentration [2] | | | | |
|---|---|---|---|---|---|
| X | −1.500 | Y | 0.000 | Z | 0.000 |
| α | 0.000 | β | 0.000 | γ | 0.000 |
| | Decentration [3] | | | | |
| X | 0.000 | Y | −0.420 | Z | 0.000 |
| α | 0.000 | β | 0.000 | γ | 0.000 |

| Specifications | |
|---|---|
| Base length (entrance pupil separation) | 3 mm |
| Angle of view (diagonal) | 90° |
| Stop diameter | ϕ1.0 mm |
| Image size | ϕ2.17 mm (1.92 × 1.08) |
| Focal length | 1.29 |
| Effective Fno | 3.94 |

EXAMPLE 2

| Surface No. | Radius of curvature | Surface separation | Decentration | Refractive index | Abbe constant |
|---|---|---|---|---|---|
| Object plane | ∞ | 100.000 | | | |
| 1 | Aspheric surface [1] | 0.600 | | 1.8830 | 40.7 |
| 2 | Aspheric surface [2] | 0.904 | | | |
| 3 | 519.737 | 1.000 | | 1.9229 | 18.9 |
| 4 | −1.493 | 0.400 | | 1.8830 | 40.7 |
| 5 | −8.396 | 1.236 | | | |
| 6 | Stop plane | 0.100 | | | |
| 7 | −18.475 | 0.300 | | 1.9229 | 18.9 |
| 8 | 4.639 | 0.800 | | 1.4875 | 70.2 |
| 9 | −1.890 | 0.100 | | | |
| 10 | ∞ | 0.500 | | 1.4875 | 70.2 |
| 11 | ∞ | 0.300 | Decentration (1) | | |
| 12 | ∞ | 0.000 | Decentration (2) | | |
| 13 | 6.088 | 1.200 | | 1.8830 | 40.7 |
| 14 | −60.708 | 0.561 | | | |
| 15 | −6.409 | 0.600 | | 1.9229 | 18.9 |
| 16 | 20.191 | 1.400 | | 1.8830 | 40.7 |
| 17 | −7.575 | 2.100 | | | |
| 18 | 3.091 | 1.600 | | 1.8921 | 32.0 |
| 19 | 10.903 | 0.448 | | | |
| 20 | ∞ | 0.750 | | 1.5163 | 64.1 |
| 21 | ∞ | 0.100 | | | |
| Image plane | ∞ | | Decentration (3) | | |

| Aspheric surface [1] | |
|---|---|
| r | 4.038 |
| k | −2.2135e+000 |

| Aspheric surface [2] | |
|---|---|
| r | 0.920 |
| k | −5.3147e−001 |

| | Decentration [1] | | | | |
|---|---|---|---|---|---|
| X | 0.000 | Y | 0.000 | Z | 0.000 |
| α | 12.070 | β | 0.000 | γ | 0.000 |
| | Decentration [2] | | | | |
| X | −1.500 | Y | 0.000 | Z | 0.000 |
| α | 0.000 | β | 0.000 | γ | 0.000 |
| | Decentration [3] | | | | |
| X | 0.000 | Y | −0.420 | Z | 0.000 |
| α | 0.000 | β | 0.000 | γ | 0.000 |

| | Specifications | |
|---|---|---|
| Base length (entrance pupil separation) | 3 mm | |
| Angle of view (diagonal) | 90° | |
| Stop diameter | φ1.0 mm | |
| Image size | φ2.17 mm (1.92 × 1.08) | |
| Focal length | 1.29 | |
| Effective Fno | 3.33 | |

EXAMPLE 3

| Surface No. | Radius of curvature | Surface separation | Decentration | Refractive index | Abbe constant |
|---|---|---|---|---|---|
| Object plane | ∞ | 100.000 | | | |
| 1 | Aspheric surface [1] | 0.600 | | 1.8830 | 40.7 |
| 2 | Aspheric surface [2] | 0.974 | | | |
| 3 | −486.159 | 1.000 | | 1.9229 | 18.9 |
| 4 | −1.281 | 0.400 | | 1.8830 | 40.7 |
| 5 | −5.917 | 0.942 | | | |
| 6 | −12.817 | 0.300 | | 1.9229 | 18.9 |
| 7 | 3.314 | 0.800 | | 1.4875 | 70.2 |
| 8 | −1.675 | 0.100 | | | |
| 9 | ∞ | 0.500 | | 1.4875 | 70.2 |
| 10 | ∞ | 0.300 | Decentration (1) | | |
| 11 | Stop plane | 0.000 | | | |
| 12 | ∞ | 0.000 | Decentration (2) | | |
| 13 | 6.676 | 1.200 | | 1.8830 | 40.7 |
| 14 | −33.664 | 0.668 | | | |
| 15 | −5.594 | 0.600 | | 1.9229 | 18.9 |
| 16 | 30.538 | 1.400 | | 1.8830 | 40.7 |
| 17 | −6.542 | 2.282 | | | |
| 18 | 3.236 | 1.600 | | 1.8943 | 30.4 |
| 19 | 12.049 | 0.483 | | | |
| 20 | ∞ | 0.750 | | 1.5163 | 64.1 |
| 21 | ∞ | 0.100 | | | |
| Image plane | ∞ | | Decentration (3) | | |

| Aspheric surface [1] | | | | | |
|---|---|---|---|---|---|
| r | 4.175 | | | | |
| k | −3.2958e+000 | | | | |

| Aspheric surface [2] | | | | | |
|---|---|---|---|---|---|
| r | 0.837 | | | | |
| k | −5.3767e−001 | | | | |

| Decentration [1] | | | | | |
|---|---|---|---|---|---|
| X | 0.00 | Y | 0.00 | Z | 0.00 |
| α | 11.68 | β | 0.00 | γ | 0.00 |

| Decentration [2] | | | | | |
|---|---|---|---|---|---|
| X | −1.50 | Y | 0.00 | Z | 0.00 |
| α | 0.00 | β | 0.00 | γ | 0.00 |

| Decentration [3] | | | | | |
|---|---|---|---|---|---|
| X | 0.00 | Y | −0.42 | Z | 0.00 |
| α | 0.00 | β | 0.00 | γ | 0.00 |

| | Specifications | |
|---|---|---|
| Base length (entrance pupil separation) | 3 mm | |
| Angle of view (diagonal) | 90° | |
| Stop diameter | φ1.0 mm | |

-continued

| | |
|---|---|
| Image size | φ2.17 mm (1.92 × 1.08) |
| Focal length | 1.29 |
| Effective Fno | 3.85 |

EXAMPLE 4

| Surface No. | Radius of curvature | Surface separation | Decentration | Refractive index | Abbe constant |
|---|---|---|---|---|---|
| Object plane | ∞ | 100.000 | | | |
| 1 | Aspheric surface [1] | 0.600 | | 1.8830 | 40.7 |
| 2 | Aspheric surface [2] | 1.066 | | | |
| 3 | 26.845 | 1.000 | | 1.9229 | 18.9 |
| 4 | −1.428 | 0.400 | | 1.8830 | 40.7 |
| 5 | −7.449 | 0.966 | | | |
| 6 | −12.279 | 0.300 | | 1.9229 | 18.9 |
| 7 | 3.471 | 0.800 | | 1.4875 | 70.2 |
| 8 | −1.709 | 0.075 | | | |
| 9 | Stop plane | 0.000 | | | |
| 10 | ∞ | 0.500 | | 1.4875 | 70.2 |
| 11 | ∞ | 0.300 | Decentration (1) | | |
| 12 | ∞ | 0.000 | Decentration (2) | | |
| 13 | 6.487 | 1.200 | | 1.8830 | 40.7 |
| 14 | −29.393 | 0.421 | | | |
| 15 | −5.655 | 0.600 | | 1.9229 | 18.9 |
| 16 | 75.749 | 1.400 | | 1.8830 | 40.7 |
| 17 | −6.615 | 2.232 | | | |
| 18 | 3.235 | 1.400 | | 1.8903 | 33.4 |
| 19 | 11.056 | 0.611 | | | |
| 20 | ∞ | 0.750 | | 1.5163 | 64.1 |
| 21 | ∞ | 0.100 | | | |
| Image plane | ∞ | | Decentration (3) | | |

Aspheric surface [1]

| | |
|---|---|
| r | 4.208 |
| k | −3.1711e+000 |

Aspheric surface [2]

| | |
|---|---|
| r | 0.877 |
| k | −5.5206e−001 |

Optical path taken by the first light beam
Decentration [1]

| X | 0.000 | Y | 0.000 | Z | 0.000 |
|---|---|---|---|---|---|
| α | 0.000 | β | 0.000 | γ | 0.000 |

Optical path taken by the second light beam
Decentration [1]

| X | 0.000 | Y | 0.000 | Z | 0.000 |
|---|---|---|---|---|---|
| α | 22.400 | β | 0.000 | γ | 0.000 |

Decentration [2]

| X | −1.500 | Y | 0.000 | Z | 0.000 |
|---|---|---|---|---|---|
| α | 0.000 | β | 0.000 | γ | 0.000 |

Optical path taken by the first light beam
Decentration [3]

| X | 0.000 | Y | 0.000 | Z | 0.000 |
|---|---|---|---|---|---|
| α | 0.000 | β | 0.000 | γ | 0.000 |

Optical path taken by the second light beam
Decentration [1]

| X | 0.000 | Y | −0.830 | Z | 0.000 |
|---|---|---|---|---|---|
| α | 0.000 | β | 0.000 | γ | 0.000 |

Specifications

| | |
|---|---|
| Base length (entrance pupil separation) | 3 mm |

| | | |
|---|---|---|
| Angle of view (diagonal) | 90° | |
| Stop diameter | ɸ1.0 mm | |
| Image size | ɸ2.17 mm (1.92 × 1.08) | |
| Focal length | 1.29 | |
| Effective Fno | 3.94 | |

EXAMPLE 6

| Surface No. | Radius of curvature | Surface separation | Decentration | Refractive index | Abbe constant |
|---|---|---|---|---|---|
| Object plane | ∞ | 15.000 | | | |
| 1 | ∞ | 0.500 | | 1.8830 | 40.7 |
| 2 | Aspheric surface [1] | 0.146 | | | |
| 3 | 1.578 | 1.000 | | 1.6923 | 26.0 |
| 4 | −0.701 | 0.400 | | 1.8830 | 40.7 |
| 5 | 48.345 | 1.066 | | | |
| 6 | 5.635 | 0.400 | | 1.8911 | 32.8 |
| 7 | 1.442 | 1.000 | | 1.6682 | 52.9 |
| 8 | −1.759 | 0.050 | | | |
| 9 | Stop plane | 0.050 | | | |
| 10 | ∞ | 0.500 | | 1.7172 | 24.7 |
| 11 | ∞ | 0.600 | Decentration (1) | 1.8303 | 42.8 |
| 12 | ∞ | 0.200 | Decentration (2) | | |
| 13 | ∞ | 0.000 | Decentration (3) | | |
| 14 | 2.608 | 2.000 | | 1.8214 | 43.2 |
| 15 | −3.428 | 0.500 | | 1.9018 | 26.2 |
| 16 | 1.541 | 1.188 | | | |
| 17 | 3.009 | 1.200 | | 1.8830 | 40.7 |
| 18 | −7.744 | 0.600 | | | |
| 19 | ∞ | 0.500 | Decentration (4) | 1.8830 | 40.7 |
| 20 | ∞ | 0.100 | | | |
| Image plane | ∞ | | Decentration(5) | | |

| Aspheric surface [1] | | | | | |
|---|---|---|---|---|---|
| Radius of curvature | 0.650 | | | | |
| k | −1.0275e+000 | | | | |

| Decentration [1] | | | | | |
|---|---|---|---|---|---|
| X | 0.000 | Y | 0.000 | Z | 0.000 |
| α | −10.000 | β | 0.000 | γ | 0.000 |

| Decentration [2] | | | | | |
|---|---|---|---|---|---|
| X | 0.000 | Y | 0.000 | Z | 0.000 |
| α | 6.259 | β | 6.391 | γ | 0.000 |

| Decentration [3] | | | | | |
|---|---|---|---|---|---|
| X | −1.100 | Y | 0.000 | Z | 0.000 |
| α | 0.000 | β | 0.000 | γ | 0.000 |

| Decentration [4] | | | | | |
|---|---|---|---|---|---|
| X | 0.000 | Y | 0.000 | Z | 0.000 |
| α | 0.000 | β | 10.417 | γ | 0.000 |

| Decentration [5] | | | | | |
|---|---|---|---|---|---|
| X | 0.000 | Y | −0.500 | Z | 0.000 |
| α | 0.000 | β | 0.000 | γ | 0.000 |

| Specifications | |
|---|---|
| Base length (entrance pupil separation) | 2.2 mm |
| Angle of view (diagonal) | 90° |
| Stop diameter | ɸ1.2 mm |
| Image size | ɸ1.47 mm (1.28 × 0.72) |
| Focal length | 1.07 |
| Effective Fno | 3.85 |

EXAMPLE 7

| Surface No. | Radius of curvature | Surface separation | Decentration | Refractive index | Abbe constant |
|---|---|---|---|---|---|
| Object plane | ∞ | 15.000 | | | |
| 1 | ∞ | 0.500 | | 1.8830 | 40.7 |
| 2 | Aspheric surface [1] | 0.146 | | | |
| 3 | 1.594 | 1.000 | | 1.6592 | 28.1 |
| 4 | −0.793 | 0.400 | | 1.8830 | 40.7 |
| 5 | −4.141 | 1.066 | | | |
| 6 | 7.965 | 0.400 | | 1.8830 | 40.7 |
| 7 | 1.641 | 1.000 | | 1.6229 | 43.5 |
| 8 | −1.734 | 0.050 | | | |
| 9 | Stop plane | 0.050 | | | |
| 10 | ∞ | 0.500 | | 1.7172 | 24.7 |
| 11 | ∞ | 0.600 | Decentration (1) | 1.8303 | 42.8 |
| 12 | ∞ | 0.200 | Decentration (2) | | |
| 13 | ∞ | 0.000 | Decentration (3) | | |
| 14 | 3.097 | 2.000 | | 1.8830 | 40.7 |
| 15 | −2.923 | 0.500 | | 1.9229 | 18.9 |
| 16 | 2.243 | 1.515 | | | |
| 17 | 2.202 | 1.200 | | 1.9105 | 22.5 |
| 18 | 17.968 | 0.273 | | | |
| 19 | Diffractive surface [1] | 0.500 | | 1.8830 | 40.7 |
| 20 | ∞ | 0.100 | | | |
| Image plane | ∞ | | Decentration(4) | | |

Aspheric surface [1]

| Radius of curvature | 0.620 |
| k | −9.8312e−001 |

Decentration [1]

| X | 0.000 | Y | 0.000 | Z | 0.000 |
|---|---|---|---|---|---|
| α | −10.000 | β | 0.000 | γ | 0.000 |

Decentration [2]

| X | 0.000 | Y | 0.000 | Z | 0.000 |
|---|---|---|---|---|---|
| α | 7.301 | β | 6.367 | γ | 0.000 |

Decentration [3]

| X | −1.100 | Y | 0.000 | Z | 0.000 |
|---|---|---|---|---|---|
| α | 0.000 | β | 0.000 | γ | 0.000 |

Decentration [4]

| X | 0.000 | Y | −0.500 | Z | 0.000 |
|---|---|---|---|---|---|
| α | 0.000 | β | 0.000 | γ | 0.000 |

Diffractive surface [1]

| Order of diffraction | 1 |
| Pitch | 0.003003 |

The values of elements and Condition (1) in such Examples 1-4, 6 and 7 as described above are set out below. For reference purposes, the separations Dep between the center axes Cf1 and Cf2 of the first and second front groups are tabulated together with the maximum effective diameter Db of the rear group.

| | Example 1 | Example 2 | Example 3 |
|---|---|---|---|
| d | 1.250 | 1.250 | 0.600 |
| f | 0.809 | 0.828 | 1.070 |
| (1) d/f | 1.545 | 1.510 | 0.561 |
| Dep | 3.00 | 3.00 | 3.00 |
| Db | φ5.06 | φ6.00 | φ4.66 |

| | Example 4 | Example 6 | Example 7 |
|---|---|---|---|
| d | 0.600 | 1.15 | 1.15 |
| f | 1.037 | 1.07 | 1.04 |
| (1) d/f | 0.579 | 1.07 | 1.11 |
| Dep | 3.00 | 2.20 | 2.20 |
| Db | φ5.29 | φ3.52 | φ3.58 |

Thus, the respective examples of the stereoscopic imaging optical system 1 according to the invention satisfy the following condition (1).

$$0 \leq d/f < 5 \quad (1)$$

where d is a distance from the front deflection group to the stop, and f is a focal length of the whole optical system.

In the respective examples of the stereoscopic imaging optical system 1 according to the invention, the separation between the center axis Cf1 of the first front group and the center axis Cf2 of the second front group is wider than the separation between the center of the first light beam L1 on the image plane I and the center of the second light beam L2 on the image plane I.

Further in the respective examples of the stereoscopic imaging optical system 1 according to the invention, the rear deflection group Gbd may further include at least one of an optical element in a wedge prism form, a diffractive optical element, and an optical element having a curved surface. In the rear deflection group Gbd, the first rear deflection group Gbd1 may be integral with the second rear deflection group Gbd2.

Still further in the respective examples of the stereoscopic imaging optical system 1 according to the invention, the front deflection group Gfd may include a front deflection member capable of achromatization. The front deflection member may further include at least one of two optical elements having different Abbe constants, each in a wedge prism form, a single optical element in a wedge prism form, and a diffractive optical element. In the front deflection group Gbd, the first front deflection group Gfd1 may be integral with the second front deflection group Gfd2.

One example of application of the stereoscopic imaging optical system 1 according to the invention is now explained.

Figure 37A:
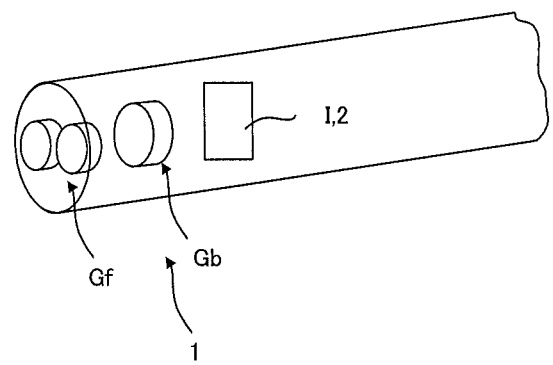
FIGS. 37A and 37B are illustrative of one example of the hard endoscope incorporating the stereoscopic imaging optical system according to one embodiment of the invention.
Figure 37B:
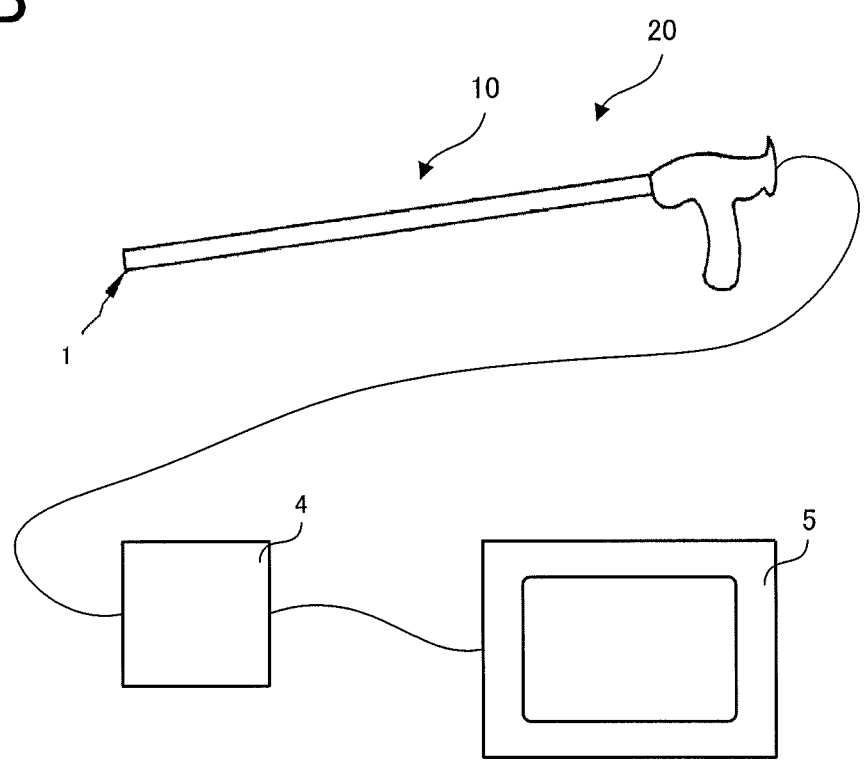
Figure 38:
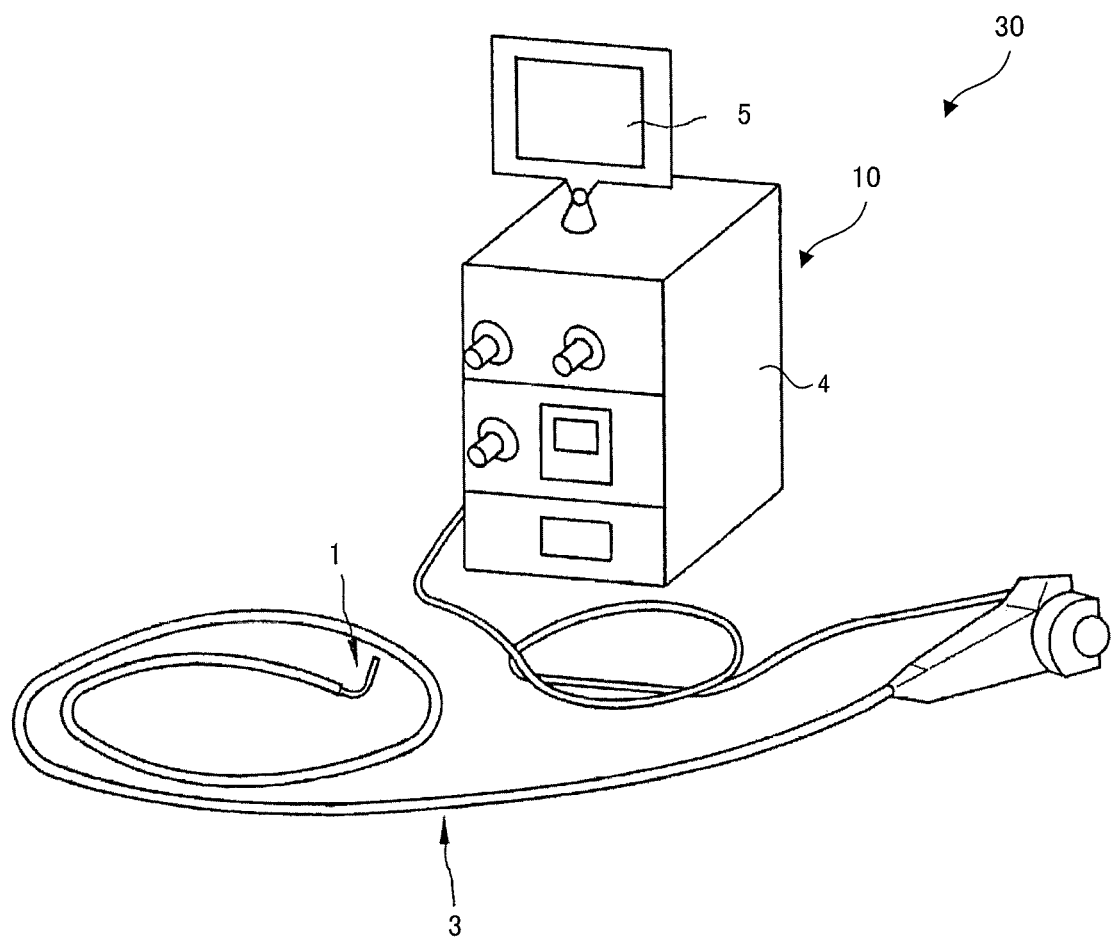
FIG. 38 is illustrative of one example of the flexible endoscope incorporating the stereoscopic imaging optical system according to one embodiment of the invention.

FIGS. 37A and 37B are illustrative of one example of the hard endoscope assembly using the stereoscopic imaging optical system according to the invention, and FIG. 38 is illustrative of one example of the flexible endoscope assembly 30 using the stereoscopic optical system according to the invention.

Specifically, FIG. 37A is illustrative in schematic of a stereoscopic imaging apparatus using the stereoscopic imaging optical system 1 according to the invention, and FIG. 37B is illustrative of one example of attaching the stereoscopic imaging optical system 1 according to the invention to the distal end of the hard endoscope assembly 20 for stereoscopic viewing of images.

Preferably, the stereoscopic imaging apparatus 10 described herein include a stereoscopic imaging optical system 1, and an imaging device 2 that is located on the image plane I and has a plurality of pixels.

With the stereoscopic imaging apparatus 10 here that is of smaller size and has higher resolution, it is possible to obtain stereoscopic images having a wide angle of view.

For the stereoscopic imaging apparatus 10 according to the invention, it is preferable that the imaging device 2 includes a single device.

By use of a single device for the imaging device 2, there may be a single wiring provided for producing imaging signals, thereby reducing the size of the stereoscopic imaging apparatus 10.

Preferably, the stereoscopic imaging apparatus 10 as described herein include an image processor 4 for electronic correction of chromatic aberrations produced at the deflection groups Gfd and Gbd as well as distortions produced at the optical system involved.

With the image processor 4 for electronic correction of chromatic aberrations produced at the deflection groups as well as distortions produced at the optical system, it is possible to provide stereoscopic presentation of high-resolution images on a display device 5.

It is here to be appreciated that the image processor 4 may also implement electronic correction of shadings produced when there is an increase in the angle of light rays incident on the imaging device 2.

For the hard or flexible endoscope assembly 20 or 30 here, it is preferable to use the stereoscopic imaging apparatus 10.

By use of the stereoscopic imaging apparatus 10 with the hard or flexible endoscope 20 or 30, that endoscope may be reduced in terms of size and allowed to have higher resolution and, hence, is less invasive.

It is here to be understood that the stereoscopic imaging apparatus may be installed on a motor vehicle. For instance, the optical system according to the invention is mounted as a part of the imaging apparatus on the front of the motor vehicle such that images taken via the respective optical units are simultaneously shown on an on-board display device after corrected for distortions by image processing. Alternatively, a plurality of optical systems according to the invention are attached as a part of the imaging apparatus to the corners of the motor vehicle or the top of a head portion such that images taken via the respective optical units are simultaneously shown on an on-board display device after corrected for distortions through image processing by the stereoscopic imaging apparatus 10.

While various embodiments of the invention have been explained, it is understood that the invention is not limited only thereto: changes or modifications made to the constructions of such embodiments or some combinations thereof are embraced in the invention as well.

REFERENCE SIGNS LIST

1: Stereoscopic imaging optical system
2: Imaging device
3: Wiring
4: Image processor
5: Display device
10: Stereoscopic imaging apparatus
20: Endoscope
Gf: Front group
Gb: Rear group
Gd: Deflection group
S: Stop
I: Image plane

The invention claimed is:

1. A stereoscopic imaging apparatus comprising, in order from an object side thereof to an image plane side thereof,
a front group including a first front group with a center axis thereof as center and a second front group with a center axis thereof arranged parallel with the center axis of the first front group as center,
a front deflection group located on an image plane side of at least one of the first and second front groups, and
a rear group that is located on the image plane side of the front group and the front deflection group and has a single center axis,
wherein:
a first light beam directed from an object passes through at least the first front group and the rear group for incidence on an image plane,
a second light beam directed from the object passes through at least the second front group and the rear group for incidence on the image plane,
at least one of the first light beam and the second light beam passes through the front deflection group, and
the front deflection group deflects the first and second light beams in different directions orthogonal to a plane that includes the center axis of the first front group, the center axis of the second front group, and the center axis of the rear group.

2. The stereoscopic imaging apparatus according to claim 1,
wherein:
the front deflection group includes a first front deflection group that is located on an image plane side of the first front group and a second front deflection group that is located on an image plane side of the second front group, the first light beam passes through at least the first front group, the first front deflection group, and the rear group, the second light beam passes through at least the second front group, the second front deflection group, and the rear group, and the front deflection group deflects the first and second light beams in directions spacing mutually away from the center axis of the rear group.

3. The stereoscopic imaging apparatus according to claim 2,
wherein the front deflection group deflects the first and second light beams in directions symmetrical with respect to the center axis of the rear group.

4. The stereoscopic imaging apparatus according to claim 1,
wherein
the first front group and the second front group include a first stop and a second stop, respectively, through which the first light beam and the second light beam pass, and
the front deflection group is located adjacent to at least one of the first stop and the second stop.

5. The stereoscopic imaging apparatus according to claim 4,
which satisfies the following condition (1):

$$0 \leq (d/f) < 5 \quad (1)$$

where d is a distance from the front deflection group to the stop, and
f is a focal length of the whole optical system.

6. The stereoscopic imaging apparatus according to claim 1,
wherein a separation between the center axis of the first front group and the center axis of the second front group is wider than a separation between a center of the first light beam on the image plane and a center of the second light beam on the image plane.

7. The stereoscopic imaging apparatus according to claim 1,
which further includes a rear deflection group that is interposed between the rear group and the image plane to deflect the first light beam and the second light beam,
wherein the rear deflection group deflects the first light beam and the second light beam after passing through the rear group symmetrically with respect to the center axis of the rear group, and deflects the first light beam and the second light beam such that angles of incidence of the first and second light beams on the image plane come close to the perpendicular.

8. The stereoscopic imaging apparatus according to claim 7,
wherein the rear deflection group includes a first rear deflection group for deflection of the first light beam, and a second rear deflection group for deflection of the second light beam.

9. The stereoscopic imaging apparatus according to claim 7,
wherein the rear deflection group includes an optical element in a wedge prism form.

10. The stereoscopic imaging apparatus according to claim 7,
wherein the rear deflection group includes a diffractive optical element.

11. The stereoscopic imaging apparatus according to claim 7,
wherein the rear deflection group includes an optical element having a curved surface.

12. The stereoscopic imaging apparatus according to claim 1,
wherein the front deflection group includes a front deflection member capable of achromatization.

13. The stereoscopic imaging apparatus according to claim 12,
wherein the front deflection member includes two optical elements that are each in a wedge prism form and have different Abbe constants.

14. The stereoscopic imaging apparatus according to claim 12,
wherein the front deflection member includes a single optical element in a wedge prism form, and a diffractive optical element.

15. A stereoscopic imaging apparatus, comprising,
the stereoscopic imaging optical system according to claim 1, and
an imaging device that is located on the image plane and includes a plurality of pixels.

16. The stereoscopic imaging apparatus according to claim 15,
wherein the imaging device comprises a single device.

17. The stereoscopic imaging apparatus according to claim 15,
which further includes an image processor for electronic correction of chromatic aberrations produced at the front deflection group.

18. An endoscope, comprising the stereoscopic imaging apparatus according to claim 15.

19. The stereoscopic imaging apparatus according to claim 1, wherein the front deflection group deflects the first and second light beams in equal and opposite directions orthogonal to the plane.

* * * * *